(12) United States Patent
Aron et al.

(10) Patent No.: US 9,327,281 B2
(45) Date of Patent: May 3, 2016

(54) CARBON-DIOXIDE COMPOUND AND CATALYST

(71) Applicants: Ioana Aron, Cambridge, MA (US); Christopher C. Cummins, Dorchester, MA (US)

(72) Inventors: Ioana Aron, Cambridge, MA (US); Christopher C. Cummins, Dorchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/575,516

(22) Filed: Dec. 18, 2014

(65) Prior Publication Data

US 2015/0306590 A1    Oct. 29, 2015

Related U.S. Application Data

(60) Provisional application No. 61/917,890, filed on Dec. 18, 2013.

(51) Int. Cl.
| | | |
|---|---|---|
| *B01J 23/28* | (2006.01) | |
| *B01J 31/34* | (2006.01) | |
| *C07F 11/00* | (2006.01) | |
| *B01J 31/24* | (2006.01) | |
| *B01J 27/232* | (2006.01) | |
| *B01J 31/16* | (2006.01) | |
| *B01J 31/22* | (2006.01) | |
| *C07F 9/50* | (2006.01) | |

(52) U.S. Cl.
CPC .............. *B01J 31/2495* (2013.01); *B01J 23/28* (2013.01); *B01J 27/232* (2013.01); *B01J 31/16* (2013.01); *B01J 31/22* (2013.01); *B01J 31/34* (2013.01); *C07F 9/5045* (2013.01); *C07F 11/005* (2013.01)

(58) Field of Classification Search
CPC ........... B01J 23/28; B01J 27/232; B01J 31/34
USPC .......................... 423/419.1, 438, 606; 556/17
See application file for complete search history.

(56) References Cited

U.S. PATENT DOCUMENTS

| | | | | |
|---|---|---|---|---|
| 4,079,116 A | * | 3/1978 | Ronzio | .................. C01G 39/00 23/297 |
| 6,207,609 B1 | * | 3/2001 | Gao | ......................... B01J 27/22 423/345 |
| 6,258,335 B1 | * | 7/2001 | Bhattacharya | ......... B01D 53/02 423/212 |
| 2004/0062710 A1 | | 4/2004 | Seegopaul et al. | |
| 2010/0034724 A1 | * | 2/2010 | Keith | ...................... B01D 53/62 423/438 |
| 2011/0030586 A1 | * | 2/2011 | Constantz | ............... C04B 7/364 106/640 |
| 2011/0179948 A1 | * | 7/2011 | Choi | ...................... B01D 53/02 95/114 |
| 2013/0078690 A1 | * | 3/2013 | Reed | ......................... C12P 7/54 435/140 |

OTHER PUBLICATIONS

International Search Report and Written Opinion mailed on Mar. 24, 2015 in PCT/US14/71135 (9 pages).

* cited by examiner

*Primary Examiner* — Porfirio Nazario Gonzalez
(74) *Attorney, Agent, or Firm* — Steptoe & Johnson LLP

(57) ABSTRACT

Tetrahedral $[MoO_4]^{2-}$ readily binds $CO_2$ to produce a robust $[MoO_3(\kappa^2\text{-}CO_3)]^{2-}$ that can affect the reduction of $CO_2$ to formate.

17 Claims, 41 Drawing Sheets

Table 1 Crystallographic details for [NEt$_4$]$_2$[MoO$_3$(κ$^2$-CO$_3$)] and [PPN]$_2$[MoO$_2$(κ$^2$-CO$_3$)$_2$]

| | [NEt$_4$]$_2$[MoO$_3$(κ$^2$-CO$_3$)] | [PPN]$_2$[MoO$_2$(κ$^2$-CO$_3$)$_2$] |
|---|---|---|
| Reciprocal Net code / CCDC no. | X8_13178 / TBD | X8_13097 / TBD |
| Empirical formula, FW (g/mol) | C$_{17}$H$_{40}$MoN$_2$O$_6$, 464.45 | C$_{74}$H$_{60}$MoN$_2$O$_8$P$_4$·4CH$_3$CN, 1489.344 |
| Color / Morphology | Colorless / Needle | Colorless / Block |
| Crystal size (mm$^3$) | 0.42 × 0.10 × 0.07 | 0.45 × 0.35 × 0.20 |
| Temperature (K) | 100(2) | 100(2) |
| Wavelength (Å) | 0.71073 | 0.71073 |
| Crystal system, Space group | Monoclinic, P2$_1$/n | Monoclinic, P2$_1$ |
| Unit cell dimensions (Å, °) | a = 14.997(3), α = 90 | a = 10.7577(11), α = 90 |
| | b = 8.3386(15), β = 99.979(3) | b = 13.0244(13), β = 90.884(2) |
| | c = 17.151(3), γ = 90 | c = 25.943(3), γ = 90 |
| Volume (Å$^3$) | 2112.4(7) | 3634.5(6) |
| Z | 4 | 2 |
| Density (calc, g/cm$^3$) | 1.460 | 1.361 |
| Absorption coefficient (mm$^{-1}$) | 0.654 | 0.330 |
| F(000) | 984 | 1544 |
| Theta range for data collection (°) | 1.667 to 30.508 | 1.570 to 30.51 |
| Index ranges | −21 ≤ h ≤ 21, −11 ≤ k ≤ 11, −24 ≤ l ≤ 24 | −15 ≤ h ≤ 15, −19 ≤ k ≤ 19, −38 ≤ l ≤ 38 |
| Reflections collected | 65759 | 203085 |
| Independent reflections, R$_{int}$ | 6441 (0.0290) | 24166 (0.0406) |
| Completeness to θ$_{max}$ (%) | 100.0 | 99.9 |
| Max. and min. transmission | 0.7462 and 0.6504 | 0.937 and 0.866 |
| Data / restraints / parameters | 6441 / 0 / 243 | 24166 / 1 / 913 |
| Goodness-of-fit[a] | 1.074 | 1.087 |
| Final R indices[b] [I > 2σ(I)] | R$_1$ = 0.0181, wR$_2$ = 0.0470 | R$_1$ = 0.0355, wR$_2$ = 0.0910 |
| R indices[b] (all data) | R$_1$ = 0.0198, wR$_2$ = 0.0479 | R$_1$ = 0.0373, wR$_2$ = 0.0918 |
| Largest diff. peak and hole (e·Å$^{-3}$) | 0.429 and −0.440 | 1.737 and −0.501 |

[a] GooF = $\left[\frac{\Sigma[w(F_o^2-F_c^2)^2]}{(n-p)}\right]^{\frac{1}{2}}$   [b] R$_1$ = $\frac{\Sigma||F_o|-|F_c||}{\Sigma|F_o|}$, wR$_2$ = $\left[\frac{\Sigma[w(F_o^2-F_c^2)^2]}{\Sigma[w(F_o^2)^2]}\right]^{\frac{1}{2}}$; w = $\frac{1}{\sigma^2(F_o^2)+(aP)^2+bP}$, P = $\frac{2F_c^2+\max(F_o^2,0)}{3}$

FIG. 38

CARBON-DIOXIDE COMPOUND AND CATALYST

PRIORITY CLAIM

This application claims priority to U.S. Provisional Patent Application No. 61/917,980, filed Dec. 18, 2013, which is incorporated by reference in its entirety.

FIELD OF THE INVENTION

The invention features compounds including carbon dioxide and catalysts for chemical transformations including carbon dioxide.

BACKGROUND

Although $CO_2$ chemical fixation cannot compete in scale with global emissions, carbon dioxide is an attractive, low-cost, nontoxic, abundant chemical feedstock. See, R. J. Andres, T. A. Boden, F. -M. Breon, P. Ciais, S. Davis, D. Erickson, J. S. Gregg, A. Jacobson, G. Marland, J. Miller, T. Oda, J. G. J. Olivier, M. R. Raupach, P. Rayner and K. Treanton, *Biogeosciences*, 2012, 9, 1845-1871, M. Mikkelsen, M. Jørgensen and F. C. Krebs, *Energy Environ. Sci.*, 2010, 3, 43-81., E. A. Quadrelli, G. Centi, J. -L. Duplan and S. Perathoner, *ChemSusChem*, 2011, 4, 1194-215, I. Omae, *Coord. Chem. Rev.*, 2012, 256, 1384-1405, A. Boddien, F. Gartner, C. Federsel, I. Piras, H. Junge, R. Jackstell and M. Beller, *Organic Chemistry—Breakthroughs and Perspectives*, Wiley-VCH Verlag GmbH & Co. KGaA, Weinheim, Germany, 1st edn, 2012, ch. 18, pp. 685-724, and M. Holscher, C. Gurtler, W. Keim, T. E. Muller, M. Peters and W. Leitner, Z. Naturforsch, B: Chem. Sci., 2012, 67b, 961-975, each of which is incorporated by reference in its entirety. Metal oxides are among the most explored compounds for $CO_2$ capture and fixation, but are challenging to study as they are of part of heterogeneous systems. See, B. Feng, H. An and E. Tan, Energy Fuels, 2007, 21, 426-434, S. Choi, J. H. Drese and C. W. Jones, *ChemSusChem*, 2009, 2, 796-854, S. Wang, K. Murata, T. Hayakawa. S. Hamakawa and K. Suzuki, *Appl. Catal., A*, 2000, 196, 1-8, B. M. Bhanage, S. -I. Fujita, Y. Ikushima and M. Arai, *Appl. Catal., A*, 2001, 219, 259-266, and M. Matsuoka and M. Anpo, *J. Photochem. Photobio., C*, 2003, 3, 225-252, each of which is incorporated by reference in its entirety,

SUMMARY

In one aspect, an isolated compound can include a molybdate complex of carbon dioxide.

In certain embodiments, the molybdate complex can include a single molybdenum atom. The molybdate complex can include a single carbonate group. The molybdate complex can include $[MoO_3(\kappa^2\text{-}CO_3)]^{2-}$. The molybdate complex can include two carbonate groups. The molybdate complex can include $[MoO_2(\kappa^2\text{-}CO_3)_2]^{2-}$.

In certain embodiments, the isolated compound can include a non-coordinating cation. The non-coordinating cation can include bis(triphenylphosphine)iminium, an ammonium or a phosphonium.

In another aspect, a method of making an isolated molybdate complex of carbon dioxide can include exposing a molybdate to carbon dioxide, and isolating the molybdate complex of carbon dioxide.

In certain embodiments, the molybdate can be exposed to greater than one atmosphere of carbon dioxide. The molybdate complex can have a formula of $[MoO_3(\kappa^2\text{-}CO_3)]^{2-}$. The molybdate complex can have a formula of $[MoO_2(\kappa^2\text{-}CO_3)_2]^{2-}$.

In another aspect, a method for carbon dioxide fixation can include exposing carbon dioxide to a molybdate in the presence of a mild nucleophile to produce a carbon dioxide-transformed product.

In another aspect, a method of sequestering carbon dioxide can include exposing carbon dioxide to a molybdate in the presence of a mild nucleophile to produce a carbon dioxide-transformed product.

In certain embodiments, the mild nucleophile can include a mild hydride source. The mild hydride source can include a silane or borane. The mild nucleophile can be an electron-rich alkene or alkyne. The mild nucleophile can be a metal hydride or metal alkyl. The mild nucleophile can be an amine.

Other aspects, embodiments, and features will be apparent from the following description, the drawings, and the claims.

BRIEF DESCRIPTION OF THE DRAWINGS

FIG. 38 is a table containing x-ray crystallographic data for [NEt$_4$]$_2$[MoO$_3$(k$^2$-CO$_3$)] and [PPN]$_2$[MoO$_2$(k$^2$-CO$_3$)$_2$].

DETAILED DESCRIPTION

Figure 1:
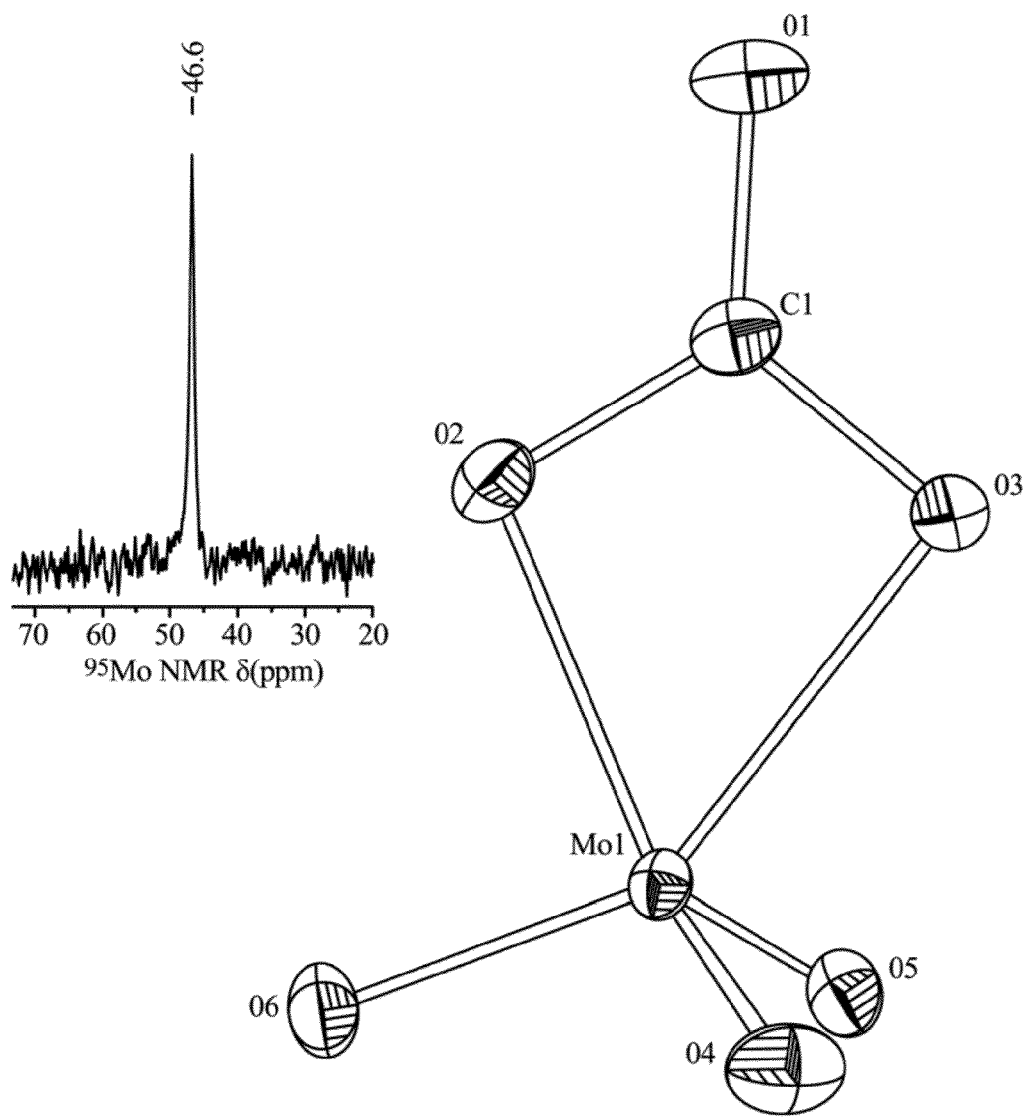
FIG. 1 is a $^{95}$Mo NMR resonance spectrum and solid-state structure of $[NEt_4]_2[MoO_3(\kappa^2\text{-}CO_3)]$ (ellipsoids at the 50% probability level, cations omitted for clarity). Representative interatomic distances [Angstroms] and angles [°]: C1-O1 1.2258(13), C1-O2 1.3357(14), C1-O3 1.3048(13), Mo1-O2 2.0674(9), Mo1-O3 2.2191(9), Mo1-O4 1.7351(8), Mo1-O5 1.7390(8), Mo1-O6 1.7436(8); C1-O2-Mo1 97.75(6), C1-O3-Mo1 91.74(7).

Terminal metal oxo species can form stable carbon dioxide complexes. Specifically, an isolated compound can include a molybdate complex of carbon dioxide or a tungstate complex of carbon dioxide. The molybdate complex can include a single molybdenum atom, derived, for example, from [MoO$_4$]$^{2-}$. When exposed to carbon dioxide under conditions where an excess of carbon dioxide is present, for example, two to three equivalents of carbon dioxide or more a complex forms that can be isolated. The isolated complex can include a single carbonate group, for example, bonded to the complex through interaction with a terminal oxo group to form a (κ$^2$-CO$_3$)$^{2-}$ group bound to the molybdenum. The molybdenum remains in a d$^0$ state, or 6+ oxidation state.

Tetrahedral [MoO$_4$]$^{2-}$ readily binds CO$_2$ to produce a robust [MoO$_3$(κ$^2$-CO$_3$)]$^{2-}$ that can affect the reduction of CO$_2$ to formate in the presence of Et$_3$SiH. Under excess CO$_2$, a second molecule of CO$_2$ binds to afford [MoO$_2$(κ$^2$CO$_3$)$_2$]$^{2-}$, the first structurally characterized transition metal dicarbonate complex derived from CO$_2$.

Under certain circumstances, for example, when exposed to excess free carbon dioxide, a second carbon dioxide adduct can form, leading to two (κ$^2$-CO$_3$)$^{2-}$ groups bound to the molybdenum. Any excess free carbon dioxide in solution will form the bis-carbonate. The evidence for the presence of the bis-carbonate in solution at room temperature under little excess carbon dioxide is the broad $^{13}$C NMR signal for the monocarbonate, which is exchanging $^{13}$C with the free carbon dioxide via the bis-carbonate. The broadening of the signal is not explained by exchange happening via the dissociation of the carbon dioxide from the molybdate, as this process is unobserved even under heating at 56° C. Under certain conditions, such as temperature of −40° C. and 1 atmosphere of CO$_2$, the bis-carbon dioxide complex can be isolated.

The compound includes a non-coordinating cation. For example, the non-coordinating cation can be bis(triphenylphosphine)iminium, ammonium or phosphonium. The ammonium can be a monoalkyl, dialkyl, triakyl, tetraalkyl or aryl ammonium. The phosphonium can be monoalkyl, dialkyl, triakyl, tetraalkyl or aryl phosphonium. In each case, the alkyl, independently, can be a C1-C16 alkyl group, preferably, a C1-C8 alkyl group, which can be optionally substituted. The aryl can be phenyl or substitued phenyl. For example, the cation can be triphenylmethylphosphonium. The non-coordinating cation can be a lightly coordinating cation. Another example of a suitable cation can be an alkali metal ion sequestered with a crown ether (for example, an 18-crown-6 potassium). The isolated compound can be formed by exposing a molybdate to carbon dioxide; and isolating the molybdate complex of carbon dioxide. The molybdate can be a salt including [MoO$_4$]$^{2-}$ dissolved in a suitable solvent. The carbon dioxide can be exposed as stoichiometric amount or higher of carbon dioxide gas. Alternatively, the molybdate in the solid state can react with carbon dioxide to form the complex.

The molybdate, [MoO$_4$]$^{2-}$, can be used to sequester carbon dioxide and store it as the isolated compound. Alternatively, the molybdate, [MoO$_4$]$^{2-}$, in the presence of carbon dioxide or the isolated carbon dioxide complex itself, can be used to activate the carbon dioxide for reduction with a mild nucleophile. For example, the mild nucleophile can be a mild hydride source, such as, a silane, for example, trimethyl silane, triethyl silane, a borane, for example, pinacolborane, or other mild hydride source. This reaction can produce formate from carbon dioxide. In another example, the mild nucleophile can be an electron-rich alkene or alkyne, such as, for example, a silyl enol ether, a metal hydride, a metal alkyl or an amine, such as an aromatic amine or diamine, for example, phenyl amine or ortho-phenylenediamine. This transformation and activity can be useful in deoxygenation of carbon dioxide. See, for example, Berkefield et al., J. Am. Chem. Soc. 2010, 132, 10660-10661, which is incorporated by reference in its entirety. The molybdate can be used to provide carbon dioxide to any process in need of a carbon dioxide source. The sequestering of carbon dioxide and subsequent reaction to form a carbon dioxide-transformed product can be direct or indirect. For example, the carbon dioxide sequestering can take place in the same vessel as a second chemical process for direct transformation. In another example, the molybdate can bind carbon dioxide and that complex can later be used in a second chemical process for indirect transformation. Advancing the understanding of $CO_2$ binding and reactivity is essential for developing new uptake technologies. Metal oxides are among the most explored compounds for $CO_2$ capture and fixation, but are challenging to study as they are oftentimes part of heterogeneous systems. Having molecular models to study the reactivity of metal oxides with $CO_2$ in solution is highly desirable. Disclosed herein is a simple metal oxo platform inspired by $CO_2$ binding using a titanium oxo anion. See, J. S. Silvia and C. C. Cummins, *Chem. Sci.*, 2011, 2, 1474-1479, which is incorporated by reference in its entirety. The molybdate dianion was a top candidate due to its simple structure, high nucleophilicity, ease of access and low cost. See, J. R. Briggs, A. M. Harrison and J. H. Robson, *Polyhedron*, 1986, 5, 281-287, J. E. Hamlin and M. J. Lawrenson, *Process for the production of either an alkylene carbonate, a glycol ether ester or a glycol ether*, GB2187454A, 1987, B. Wikjord and L. D. Byers, *J. Am. Chem. Soc.*, 1992, 114, 5553-5554, B. R. Wikjord and L. D. Byers, *J. Org. Chem.*, 1992, 57, 6814-6817, C. Polydore, D. Roundhill and H.-Q. Liu, *J. Mol. Catal. A: Chem.*, 2002, 186, 65-68, and D. V. Partyka and R. H. Holm, *Inorg. Chem.*, 2004, 43, 8609-8616, each of which is incorporated by reference in its entirety. Selective $CO_2$ uptake has been reported for a metal-organic material containing $[MoO_4]^{2-}$ pillars, a zirconium $\kappa^2$-carbonate was prepared from a zirconium oxo complex and $CO_2$, and the tungstate dianion was shown to be an efficient catalyst for carbon dioxide fixation with challenging organic substrates such as aromatic diamines or 2-aminobenzonitriles. See, M. H. Mohamed, S. K. Elsaidi, L. Wojtas, T. Pham, K. a. Forrest, B. Tudor, B. Space and M. J. Zaworotko, *J. Am. Chem. Soc.*, 2012, 134, 19556-19559, J. P. Krogman, M. W. Bezpalko, B. M. Foxman and C. M. Thomas, *Inorg. Chem.*, 2013, 52, 3022-3031, T. Kimura, K. Kamata and N. Mizuno, *Angew. Chem. Int. Ed.*, 2012, 51, 6700-6703, and T. Kimura, H. Sunaba, K. Kamata and N. Mizuno, *Inorg. Chem.*, 2012, 51, 13001-13008, each of which is incorporated by reference in its entirety.

Here, a procedure for preparing $[PPN]_2[MoO_4]$ ($PPN^+ = (Ph_3P)_2N^+$) in one step from $Ag_2MoO_4$ and PPNCl is disclosed that overcomes the limitation of the commercially available sodium molybdate that is practically insoluble in most organic solvents and does not react with $CO_2$ under aqueous conditions. A new species quickly formed upon addition of $CO_2$ to a solution of $[PPN]_2[MoO_4]$ at room temperature. $^{95}$Mo NMR spectrum of the product mixture reveals a new resonance at +46.7 ppm, no more starting material (+13.2 ppm), but also a small amount of $[Mo_2O_7]^{2-}$ by-product at −3.8 ppm. A new characteristic carbonyl stretch at 1638 cm$^{-1}$ could also be observed by IR. See G. Busca and V. Lorenzelli, *Mater. Chem.*, 1982, 7, 89-126.

A preliminary X-ray crystal structure of the $CO_2$-addition product revealed a $\kappa^2$-bound carbonate moiety and enabled formulation of the major product obtained as $[PPN]_2[MoO_3(\kappa^2\text{-}CO_3)]$. Unfortunately, crystals obtained with the PPN counterion were low quality. Since $[NEt_4]_2[MoO_4]$ had been previously reported in the literature and used to prepare a few crystallographically characterized molybdenum complexes, this starting material was used to obtain the $[MoO_3(\kappa^2\text{-}CO_3)]^{2-}$ dianion as its tetraethylammonium salt.

X-ray diffraction quality crystals were grown by slow vapor diffusion of $Et_2O$ into a $CH_3CN$ solution of $[NEt_4]_2[MoO_3(\kappa^2\text{-}CO_3)]$, and the resulting structure is shown in FIG. 1. The C—O distances are elongated from 1.162 Angstroms in free $CO_2$ to 1.2258(13) Angstroms, 1.3048(13) Angstroms, and 1.3357(14) Angstroms in the carbonate unit. The average Mo—O distance is 1.739 Angstroms for the three molybdenum oxo bonds, shorter than the average Mo—O distance of 1.776 Angstroms in tetrahedral $[MoO_4]^{2-}$. The carbonate ligand has more elongated Mo—O bonds of 2.0674(9) and 2.2191(9) Angstroms. The slight asymmetry of the carbonate induced by the trans influence of one of the molybdenum oxo ligands is reflected in the C—O bond lengths that differ by approximately 0.031 Angstroms, but also in the different Mo—O—C angles of 97.75(6) and 91.74(7)°. This $\kappa^2$ binding mode is not surprising given the lack of steric bulk around the molybdenum center, in contrast to $[O_2COTiX_3]^-$ (X=N[$^t$Bu](3,5-Me$_2$C$_6$H$_3$))for which a combination of ancillary ligand steric bulk and external carbonate complexation by an alkali-metal counter-ion promotes $\kappa^1$-binding of $CO_3^{2-}$ to the titanium center.

Solid $[PPN]_2[MoO_3(\kappa^2\text{-}CO_3)]$ is moderately stable in air, and does not lose $CO_2$ even after being heated at 70° C. under vacuum for 1 h. In solution, $[PPN]_2[MoO_3(\kappa2\text{-}^{13}CO_3)]$ was heated to 56° C. without any observable loss of $^{13}CO_2$ as confirmed by $^{13}C$ NMR spectroscopy. However, this compound is moisture sensitive, as it converts to $[PPN]_2[MoO_4]$ when even a few equivalents of water is added to a solution of $[PPN]_2[MoO_3(\kappa^2\text{-}CO_3)]$. On the other hand, solid $[NEt_4]_2[MoO_3(\kappa^2\text{-}CO_3)]$ is hygroscopic and undergoes decomposition in ca. 15 minutes by absorbing moisture from the ambient atmosphere.

$[PPN]_2[MoO_3(\kappa^2\text{-}^{13}CO_3)]$ prepared and isolated using $^{13}CO_2$ displays a sharp carbonate resonance at 165.7 ppm by $^{13}C$ NMR spectroscopy, a region characteristic for carbonates. See, J. S. Silvia and C. C. Cummins, *Chem. Sci.*, 2011, 2, 1474-1479, J. P. Krogman, M. W. Bezpalko, B. M. Foxman and C. M. Thomas, *Inorg. Chem.*, 2013, 52, 3022-3031, and D. J. Darensbourg, K. M. Sanchez and A. L. Rheingoldib, *J. Am. Chem. Soc.*, 1987, 109, 290-292, each of which is incorporated by reference in its entirety. In its IR spectrum, an isotope-shifted carbonyl stretch is present at 1599 cm$^{-1}$, very close to the theoretical 1602 cm$^{-1}$ predicted based on the stretch of $[PPN]_2[MoO_3(\kappa^2\text{-}CO_3)]$ at 1638 cm$^{-1}$. A small peak at 158.9 ppm could also be observed by $^{13}C$ NMR, correlated with the trace dimolybdate by-product detected by $^{95}$Mo NMR spectroscopy. Adding $[PPN][HCO_3]$ to a mixture of $[PPN]_2[MoO_3(\kappa^2\text{-}^{13}CO_3)]$ and this unknown species yielded an increase in the unknown peak and no additional resonances, allowing us to identify $[HCO_3]^-$ as the by-product. See, M. L. Meckfessel Jones, *PhD thesis*, Texas A&M University, 1994, which is incorporated by reference in its entirety. It is likely that during the synthesis of $[PPN]_2[MoO_3(\kappa^2\text{-}CO_3)]^{2-}$, a small amount of unreacted $[MoO_4]^{2-}$ can attack a $[MoO_3(\kappa^2\text{-}CO_3)]^{2-}$ molecule to yield $[Mo_2O_7]^{2-}$ and free $[CO_3]^{2-}$, the latter then picking up a proton from adventitious water to become $[HCO_3]^-$.

Under 1 atmosphere of $^{13}CO_2$, the room temperature $^{13}C$ NMR spectrum of a $[PPN]_2[MoO_4]$ solution reveals 2 broad signals: one for the free $^{13}CO_2$ at 125.8 ppm, and one for the molybdenum carbonate at 165.3 ppm, indicating that a fast chemical exchange is occurring. A new major resonance appeared at 162.8 ppm when acquiring the spectrum at −19° C., but disappeared after degassing the sample. The ratio of the unknown species at 162.8 ppm to $[MoO_3(\kappa^2\text{-}^{13}CO_3)]^{2-}$ increases at higher pressure of $^{13}CO_2$ (3 atmospheres), and at lower temperatures (−31° C.). These data are indicative of additional reversible binding of the $^{13}CO_2$ to the $[MoO_3(\kappa^2\text{-}^{13}CO_3)]^{2-}$.

The existence of a $[PPN]_2[MoO_2(\kappa^2\text{-}CO_3)_2]$ species was confirmed by X-ray crystallography (FIG. 2), as diffraction quality crystals were grown by slowly cooling a $CH_3CN$ solution of [PPN]$_2$[MoO$_4$] under an atmosphere of CO$_2$. In the solid state, both carbonates are bound κ$^2$, with Mo—O distances of 2.198(2) and 2.024(2), 2.175(2) and 2.0145(19) Å for the two carbonate ligands, respectively. The molybdenum oxo distances are 1.695(2) and 1.705(3) Å, shorter than in [MoO$_3$(κ$^2$-CO$_3$)]$^{2-}$ as the Mo—O π character is shared over fewer centers. The carbonates exhibit the same type of asymmetry as in [MoO$_3$(κ$^2$-CO$_3$)]$^{2-}$ due to the trans influence of the oxo ligands. Several examples of κ$^2$-bound molybdenum carbonates are reported in the Cambridge Structural Database (see, J. Chatt, M. Kubota, G. J. Leigh, F. C. March, R. Mason and D. J. Yarrow, *J. Chem. Soc., Chem. Commun.*, 1974, 1033-1034, E. Carmona, F. Gonzalez, M. L. Poveda, J. M. Marin, J. L. Atwood and R. D. Rogers, *J. Am. Chem. Soc.*, 1983, 105, 3365-3366, D. M. Curtis and K. R. Han, *Inorg. Chem.*, 1985, 24, 378-382, K. A. Belmore, R. A. Vanderpool, J. -C. Tsai, M. A. Khan and K. M. Nicholas, *J. Am. Chem. Soc.*, 1988, 110, 2004-2005, and L. Contreras, M. Paneque, M. Sellin, E. Carmona, P. J. Perez, E. Gutierrez-Puebla, A. Monge and C. Ruiz, *New J. Chem.*, 2005, 29, 109-115, each of which is incorporated by reference in its entirety), this is the first example of a molybdenum complex with two κ$^2$-carbonates. [PPN]$_2$[MoO$_2$(κ$^2$-CO$_3$)$_2$] is also the first transition metal dicarbonate complex obtained directly from CO$_2$. See, S. V. Krivovichev and P. C. Burns, *Radiochemistry*, 2004, 46, 12-15. 33 Y. Do, E. D. Simhon and R. H. Holm, *Inorg. Chem.*, 1985, 24, 1831-1838, which is incorporated by reference in its entirety.

To see whether molybdenum carbonate can act as a source of activated CO$_2$, molybdenum carbonate was subjected to a mild hydride source such as triethylsilane, which exhibits no background reactivity with CO$_2$. A test reaction revealed a new resonance at 8.73 ppm by $^1$H NMR spectroscopy, a region characteristic for formyl protons, and also a new species by $^{95}$Mo NMR spectroscopy at −23.7 ppm, a shift essentially identical to that reported for the [MoO$_3$(OSiMe$_3$)]$^{31}$ anion. See, Y. Do, E. D. Simhon and R. H. Holm, Inorg. Chem., 1985, 24, 1831-1838, which is incorporated by reference in its entirety. The conversion to the formate improves dramatically if the reaction is run under an atmosphere of CO$_2$, which raises the question whether the active species that enables CO$_2$ reduction is [MoO$_3$(κ$^2$-CO$_3$)]$^{2-}$ or [MoO$_2$(κ$^2$-CO$_3$)$_2$]$^{2-}$. After a brief optimization, clean conversion to [PPN][OCHO] and [PPN][MoO$_4$SiEt$_3$] as the sole products can be obtained after 22 h at 85° C., as evidenced by the $^1$H NMR spectrum of the crude reaction. From this reaction mixture, we were able to isolate [PPN][OCHO] in 69% yield, along with [PPN][MoO$_4$SiEt$_3$] in 50% yield based on their different solubilities in THF.

In summary, two molybdenum oxo carbonate species obtained from the uptake of CO$_2$ by the molybdate dianion were structurally characterized and their reactivity was explored in the context of CO$_2$ reduction to formate. $^{13}$C-labeling experiments suggest that the first binding event to form [MoO$_3$(κ$^2$-CO$_3$)]$^{2-}$ is irreversible, while the second CO$_2$ molecule binds reversibly.

General Method

All manipulations were performed using standard Schlenk techniques or in a nitrogen atmosphere glovebox, unless otherwise stated. All reagents were purchased from Aldrich or Alfa Aesar. Ag$_2$MoO$_4$ was prepared from Na$_2$MoO$_4$·2 H$_2$O following a literature procedure. See, C. Rosner and G. Lagaly, *J. Solid State Chem.*, 1984, 53, 92-100, which is incorporated by reference in its entirety. [PPN][HCO$_3$] was also prepared using a reported synthesis. See, M. L. Meckfessel Jones, *Ph.D. thesis*, Texas A&M University, 1994, which is incorporated by reference in its entirety. [NEt$_4$]$_2$[MoO$_4$] was synthesized from commercially available [NEt$_4$]OH and H$_2$MoO$_4$ following a literature procedure for a similar compound. [NnBu$_4$]$_2$[WO$_4$]. See, T. M. Che, V. W. Day, L. C. Francesconi, M. F. Fredrich, W. G. Klemperer and W. Shum, *Inorg. Chem.*, 1985, 24, 4055-4062, which is incorporated by reference in its entirety. Solvents (EMD Chemicals) were either used as received or purified on a Glass Contour Solvent Purification System built by SG Water USA, LLC. IR spectra were recorded on a Bruker Tensor 37 Fourier transform IR (FTIR) spectrometer. Elemental analyses were performed by Robertson Microlit Laboratories, Inc. Low-temperature X-ray diffraction data were collected on a Broker X8 Kappa DUO four-circle diffractometer coupled to a Bruker Smart APEX2 charged coupled device (CCD) detector. The structures were solved by direct methods using SHELXS-97 or intrinsic phasing using SHELXT and refined against F$^2$ all data by full-matrix least squares with SHELXL-2012 using established methods. All non-hydrogen atoms were refined anisotropically. NMR solvents were obtained from Cambridge Isotope Laboratories, and NMR spectra were obtained on a Bruker 400 MHz spectrometer. For low temperature experiments, all reported temperatures have been calibrated using a methanol standard. $^1$H NMR and $^{13}$C{$^1$H} NMR are referenced to residual protio-solvent signals, $^{95}$Mo NMR spectra are referenced to a 2 M Na$_2$MoO$_4$ in D$_2$O external standard, and $^{31}$P NMR spectra are referenced to a 85% H$_3$PO$_4$ external standard.

Synthesis of [PPN]$_2$[MoO$_4$]

Outside the glovebox, Ag$_2$MoO$_4$ (9.93 g, 26.4 mmol, 1.1 equiv) and PPNCl (27.56 g, 48 mmol, 2 equiv) were weighed and transferred to a 2 L round bottom flask. 900 mL of 2:1 CH$_3$CN:H$_2$O (pH 8) solvent mixture was added to the solids, the flask was sealed with a septum, and shielded from light with aluminum foil. The slurry was stirred vigorously at room temperature for 24 h. After 24 h, the slurry was filtered through a pad of Celite, then the filtrate was concentrated to 200 mL using a rotary evaporator. Most of the remaining water was removed under vacuum on the Schlenk line. The thick slurry (ca. 80 mL water left) was filtered on a medium porosity frit and washed with 2×40 mL of cold water (pH 8). The white solid was briefly dried on the frit, then transferred to a flask and dried under vacuum overnight, after which it was slurried for 30 minutes in 130 mL of dry Et$_2$O, filtered, and dried on the frit. The resulting powder was transferred to a 500 mL round bottom flask and dried under vacuum overnight. The solid was split into smaller batches dried under vacuum at room temperature over P$_2$O$_5$. 23.31 g of material were obtained (79% yield).

Characterization of [PPN]$_2$[MoO$_4$] (FIGS. 3-7)

$^1$H NMR (CD$_3$CN, 25° C., 400.1 MHz) δ: 7.67 (1 H, m), 7.57 (2 H, m), 7.48 (2 H, m) ppm. $^{13}$C{$^1$H} NMR (CD$_3$CN, 25° C., 100.6 MHz) δ: 134.6 (s), 133.2 (m), 130.4 (m), 128.2 (d, $^1$JPC−108 Hz) ppm.

$^{95}$Mo NMR (CD$_3$CN, 25° C., 26.1 MHz) δ: 13.2 ppm.

$^{31}$P{$^1$H} NMR (CD$_3$CN, 25° C., 162.0 MHz) δ: 21.96 ppm. ATR-IR: 3045, 1639, 1586, 1481, 1436, 1282, 1241, 1184, 1110, 1026, 996, 811, 788, 753, 721, 690, 615 cm$^{-1}$.

Elemental analysis [%] found (calculated for C$_{72}$H$_{60}$MoN$_2$O$_4$P$_4$): C, 69.72 (69.90); H, 4.71 (4.89); N, 2.09 (2.26).

Synthesis of [PPN]$_2$[MoO$_3$(κ$^2$-CO$_3$)]

[PPN]$_2$[MoO4] (1.24 g, 1 mmol, 1 equiv) was dissolved in 25 mL of CH$_3$CN and transferred to a round bottom flask that was then capped with a septum. The flask was taken outside the glovebox where 60 mL (2.5 mmol, 2.5 equiv) of CO$_2$ were bubbled through the solution. After 5 min, the solvent was removed under vacuum, after which the flask was brought back inside the glovebox and the white solid triturated with 3×5 mL of Et2O. 1.15 g of white solid were obtained (93% yield). The product obtained through this method is a 18:1 mixture (assessed by $^{95}$Mo NMR) of [PPN]$_2$[MoO$_3$($\kappa^2$CO$_3$)] and [PPN]$_2$[Mo$_2$O$_7$]. We were unable to separate the two compounds because of their very similar solubility properties.

Characterization of [PPN]$_2$[MoO$_3$($\kappa^2$-CO$_3$)] (FIGS. 8-12)

$^1$H NMR (CD$_3$CN, 25° C., 400.1 MHz) δ: 7.66 (1 H, m), 7.57 (2 H, m), 7.48 (2 H, m) ppm.

$^{13}$C{$^1$} NMR (CD$_3$CN, 25° C., 100.6 MHz) δ: 134.6 (s), 133.2 (m), 130.4 (m), 128.2 (d, $^1$JPC=108 Hz) ppm.

$^{95}$Mo NMR (CD$_3$CN, 25° C., 26.1 MHz) δ: 46.7 ([MoO$_3$($\kappa^2$-CO$_3$)]$^{2-}$), −3.8 ([Mo$_2$O$_7$]$^{2-}$) ppm. $^{31}$P{$^1$H} NMR (CD$_3$CN, 25° C., 162.0 MHz) δ: 21.93 ppm.

ATR-IR: 3050, 1676, 1638 (s), 1586, 1481, 1436, 1247, 1180, 1163, 1109, 1022, 997, 903, 836, 800, 760, 750, 721, 689, 615 cm$^{-1}$

Elemental analysis [%] found (calculated for C$_{73}$H$_{60}$MoN$_2$O$_6$P$_4$): C, 68.71 (68.44); H, 4.70 (4.72); N, 1.98 (2.19).

Synthesis of [NEt$_4$]$_2$[MoO$_3$($\kappa_2$-CO$_3$)]

[NEt$_4$]$_2$[MoO$_4$] (840 mg, 2 mmol, 1 equiv) was dissolved in 40 mL of CH$_3$CN and transferred to a Schlenk flask that was then capped with a septum. The flask was taken outside the glovebox where 120 mL (5 mmol, 2.5 equiv) of CO$_2$ were bubbled through the solution. After 10 min, the solvent was removed under vacuum, after which the flask was brought back inside the glovebox. 800 mg of white solid were obtained (86% yield).

Characterization of [NEt$_4$]$_2$[MoO$_3$($\kappa_2$-CO$_3$)] (FIGS. 13-16)

$^1$H NMR (CD$_3$CN, 25° C., 400.1 MHz) δ: 3.26 (2 H, q, $^3$J$_{HH}$=7.3 Hz), 1.22 (3 H, tt, $^3$J$_{HH}$=7.3 Hz, $^2$J$_{HH}$=1.8 Hz) ppm.

$^{13}$C{$^1$H} NMR (CD$_3$CN, 25° C., 100.6 MHz) δ: 165.6, 53.1, 7.9 ppm.

$^{95}$Mo NMR (CD$_3$CN, 25° C., 26.1 MHz) δ: 46.4 ppm.

ATR-IR: 2984, 1628 (s), 1453, 1394, 1265, 1185, 1019, 1005, 901, 839, 807, 757, 676, 626 cm$^{-1}$

Elemental analysis [%] found (calculated for C$_{17}$H$_{40}$MoN$_2$O$_6$): C, 43.71 (43.96); H, 8.93 (8.68); N, 6.27 (6.03).

Reaction of [PPN]$_2$[MoO$_3$($\kappa^2$-CO$_3$)] with Et$_3$SiH

[PPN]$_2$[MoO$_3$($\kappa^2$-CO$_3$)] (513 mg, 0.4 mmol, 1 equiv) was dissolved in 6 mL of CH$_3$CN and transferred to a Schlenk tube, followed by triethylsilane (140 mg, 1.2 mmol, 3 equiv) dissolved in 4 mL of CH3CN. The Schlenk tube was sealed and taken outside the glovebox, where it was connected to the Schlenk line and degassed using 4 freeze-pump-thaw cycles. The tube was then refilled with CO$_2$ (1 atmosphere) from the manifold, closed, and heated in 85° C. overnight (22 h). The solvent was removed under vacuum and the flask was brought back into the glovebox. The crude residue was triturated with Et$_2$O (5×8 mL) to remove traces of CH$_3$CN and obtain an off-white powder. This crude solid was placed on a frit and washed with 3×3 mL THF. The THF insoluble white solid collected was analyzed by NMR and IR and confirmed to be [PPN][OCHO] (162 mg, 69% yield). The THF filtrate was concentrated and triturated with ether (3×3 mL). 284 mg of product were collected, and confirmed to be [PPN][MoO$_4$SiEt$_3$] with a small amount of [PPN][OCHO] contamination. The product was crystallized by slow cooling of a 3:1 THF:Et2O solution, filtered, and washed with 3×1 mL Et2O to give 161 mg [PPN][MoO$_4$SiEt$_3$] (50% yield).

Figure 16:
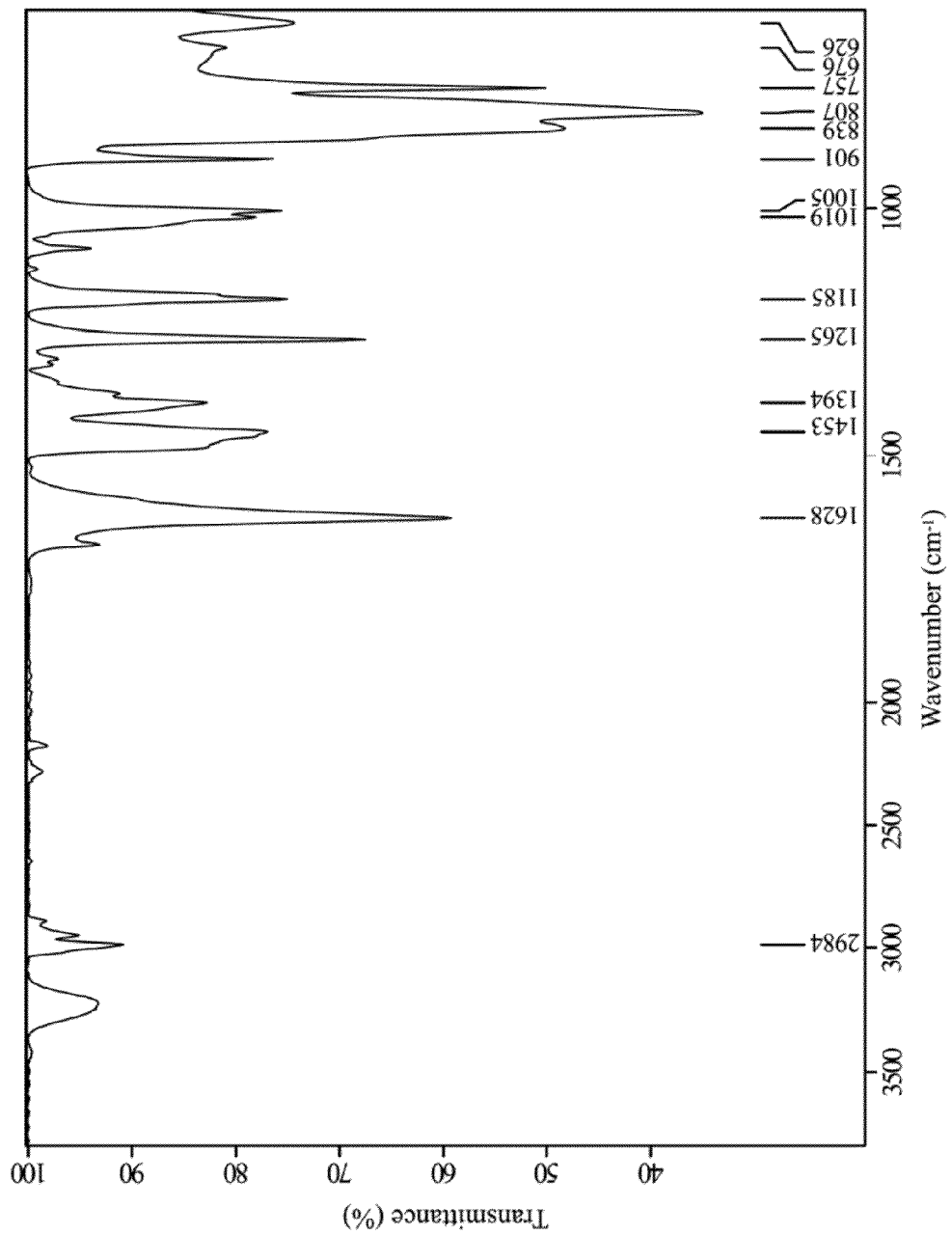
FIG. 16 is an ATR-IR spectrum of $[NEt_4]_2[MoO_3(k^2\text{-}CO_3)]$ in $CD_3CN$ at 25° C.
Figure 17:
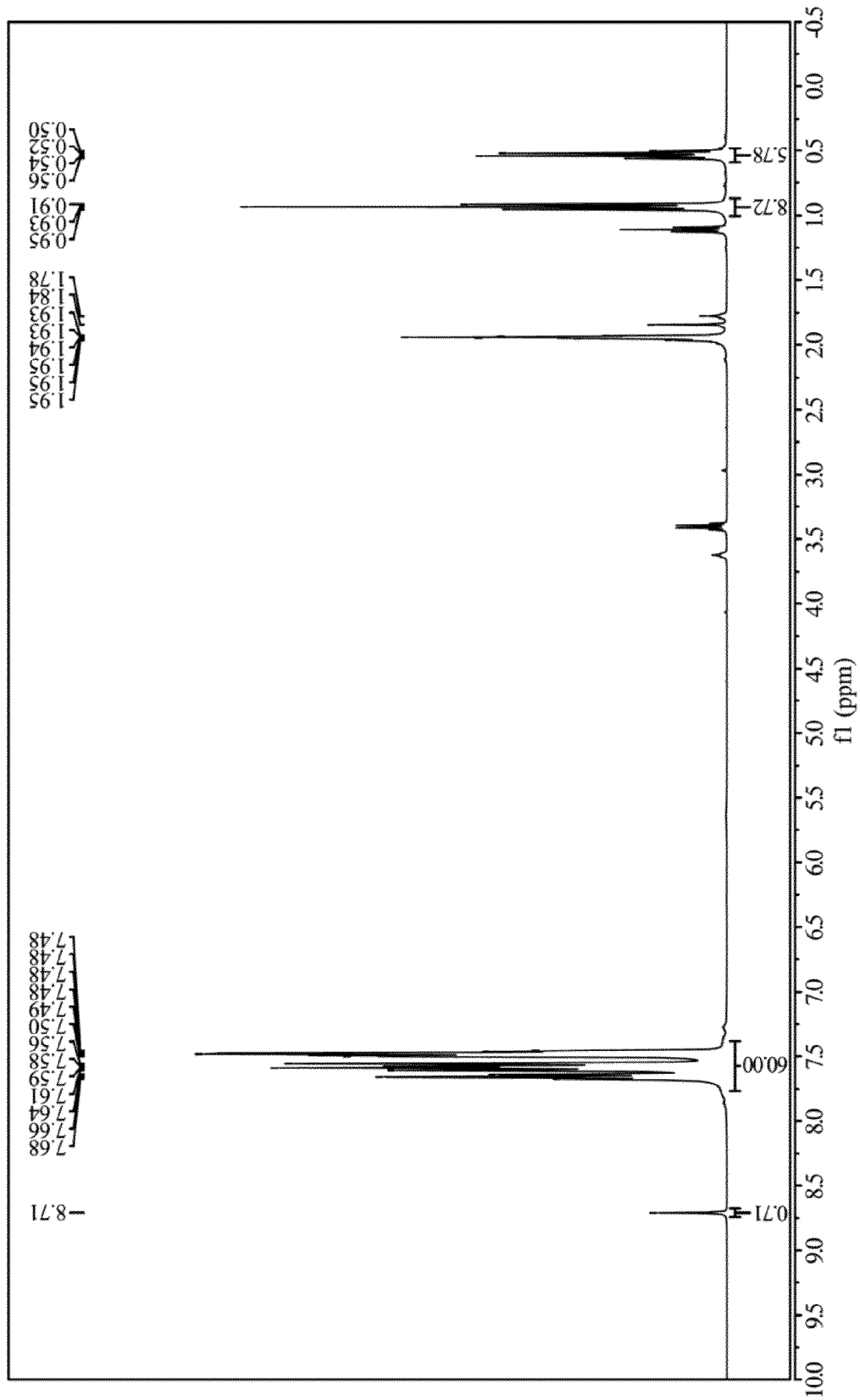
FIG. 17 is a $^1$H NMR spectrum of the crude reaction mixture containing [PPN][OCHO] and [PPN][MoO$_4$SiEt$_3$] in CD$_3$CN at 25° C.
Figure 18:
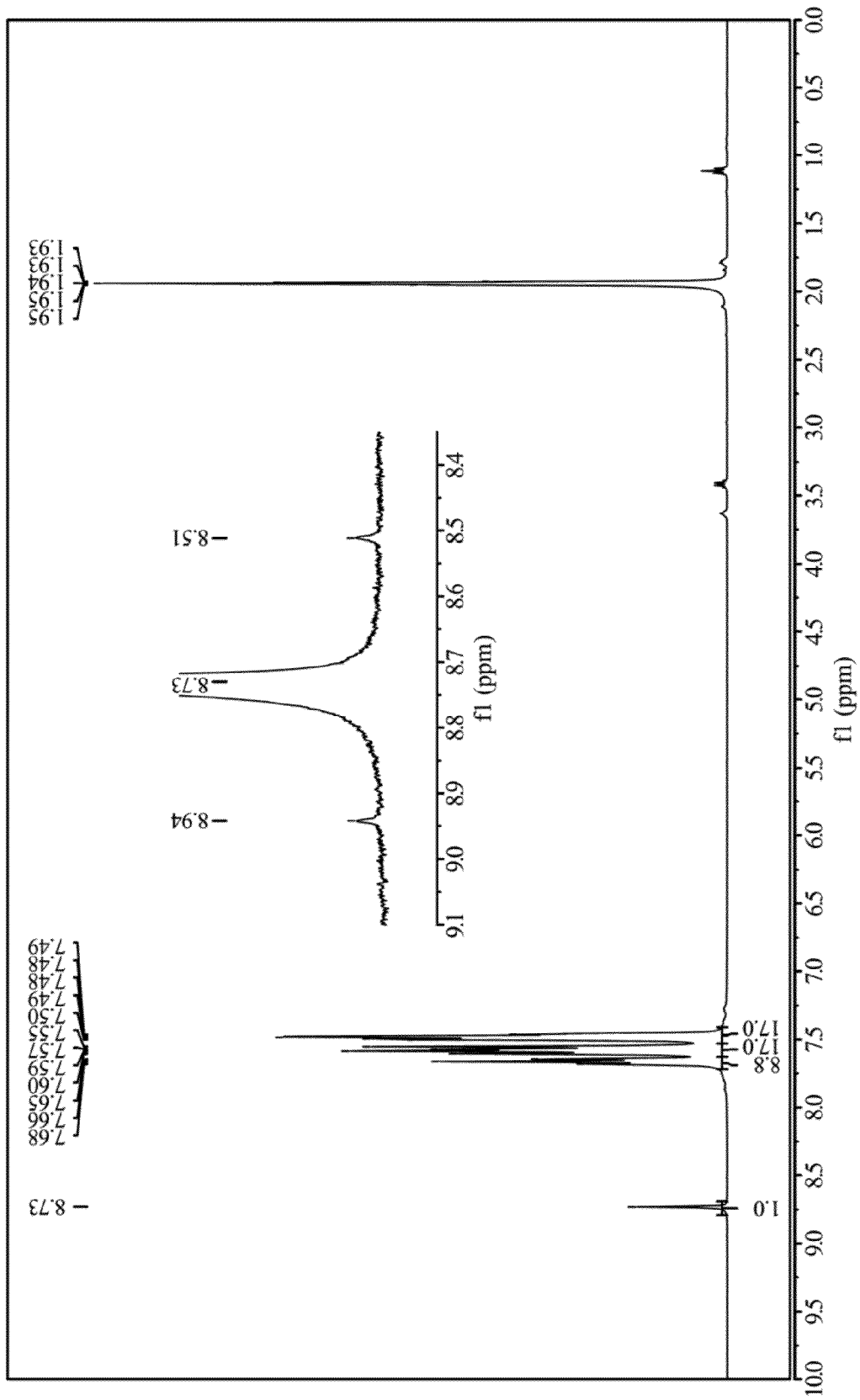
FIG. 18 is a $^1$H NMR spectrum of [PPN][OCHO] in CD$_3$CN at 25° C.
Figure 19:
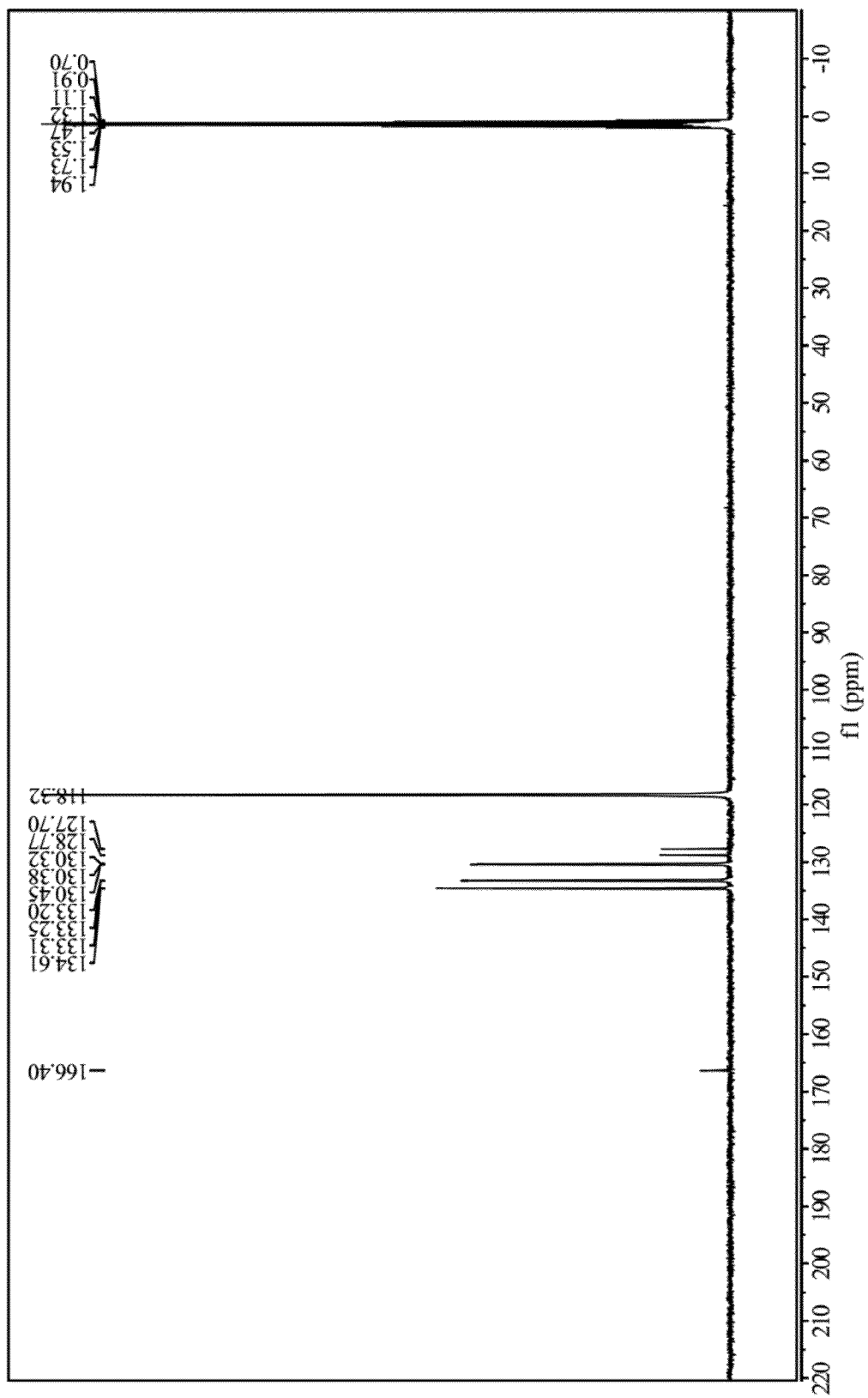
FIG. 19 is a $^{13}$C NMR spectrum of [PPN][OCHO] in CD$_3$CN at 25° C.
Figure 20:
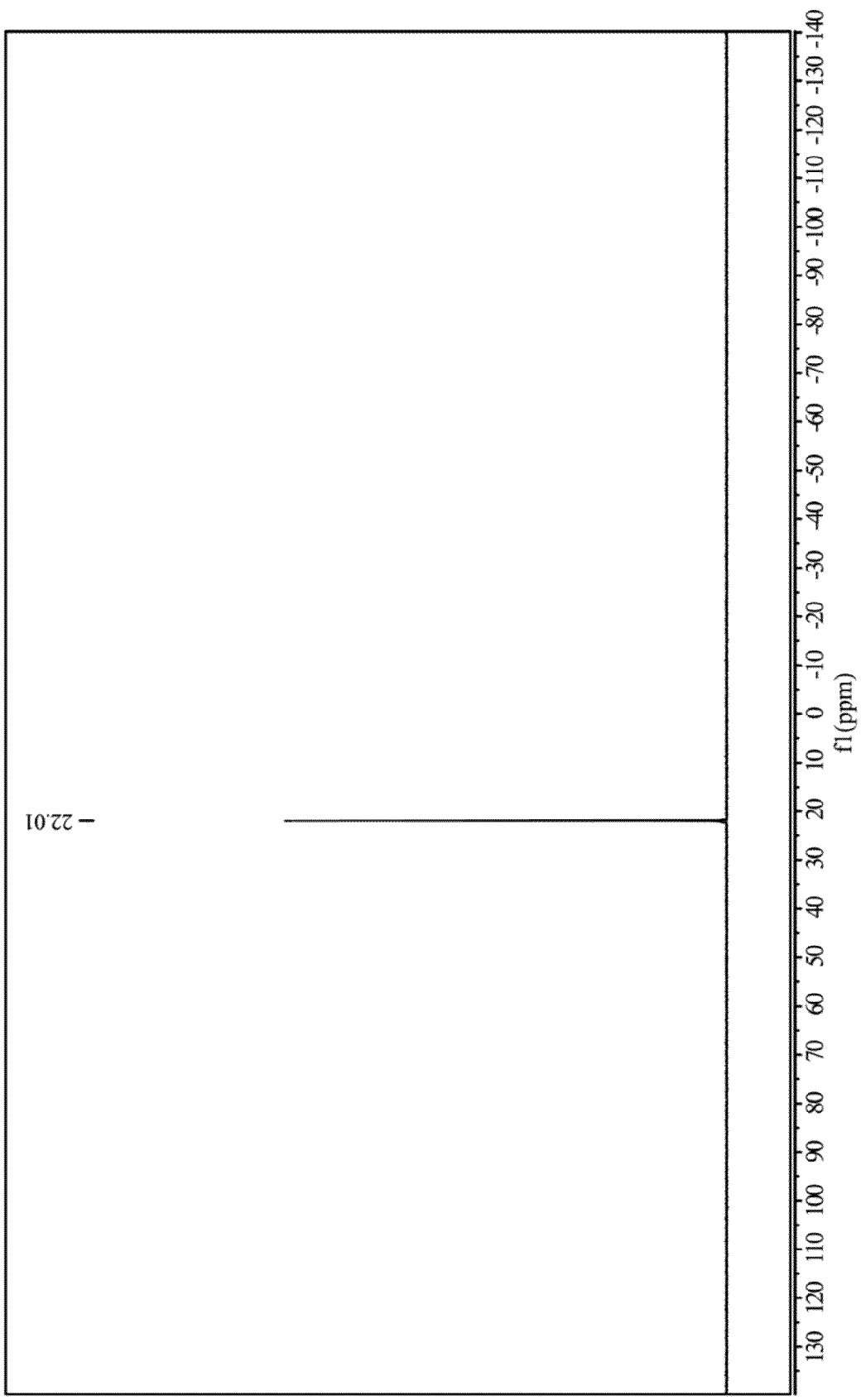
FIG. 20 is a $^{31}$P NMR spectrum of [PPN][OCHO] in CD$_3$CN at 25° C.
Figure 21:
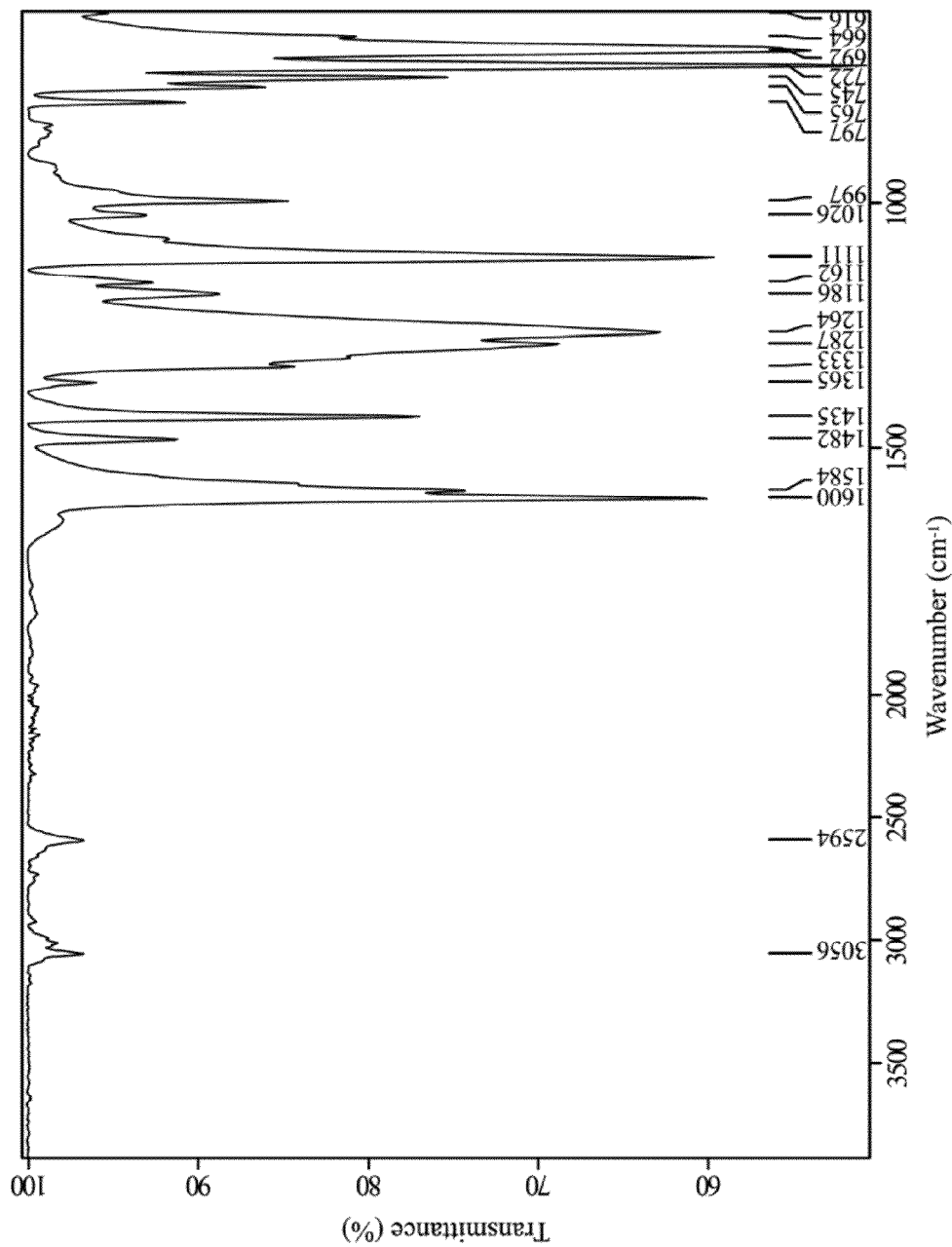
FIG. 21 is an ATR-IR spectrum of [PPN][OCHO].
Figure 22:
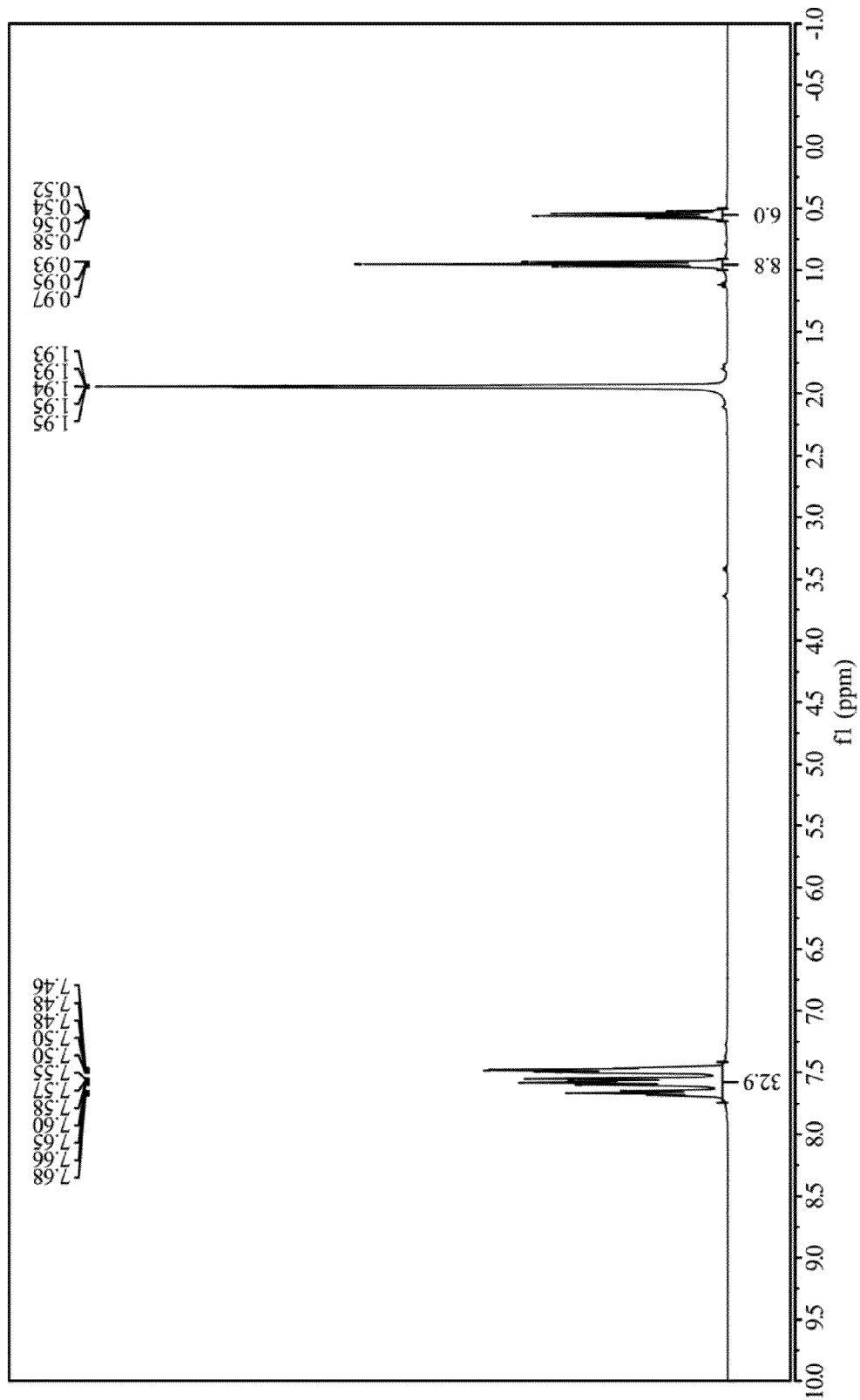
FIG. 22 is a $^1$H NMR spectrum of [PPN][MoO$_4$SiEt$_3$] in CD$_3$CN at 25° C.
Figure 23:
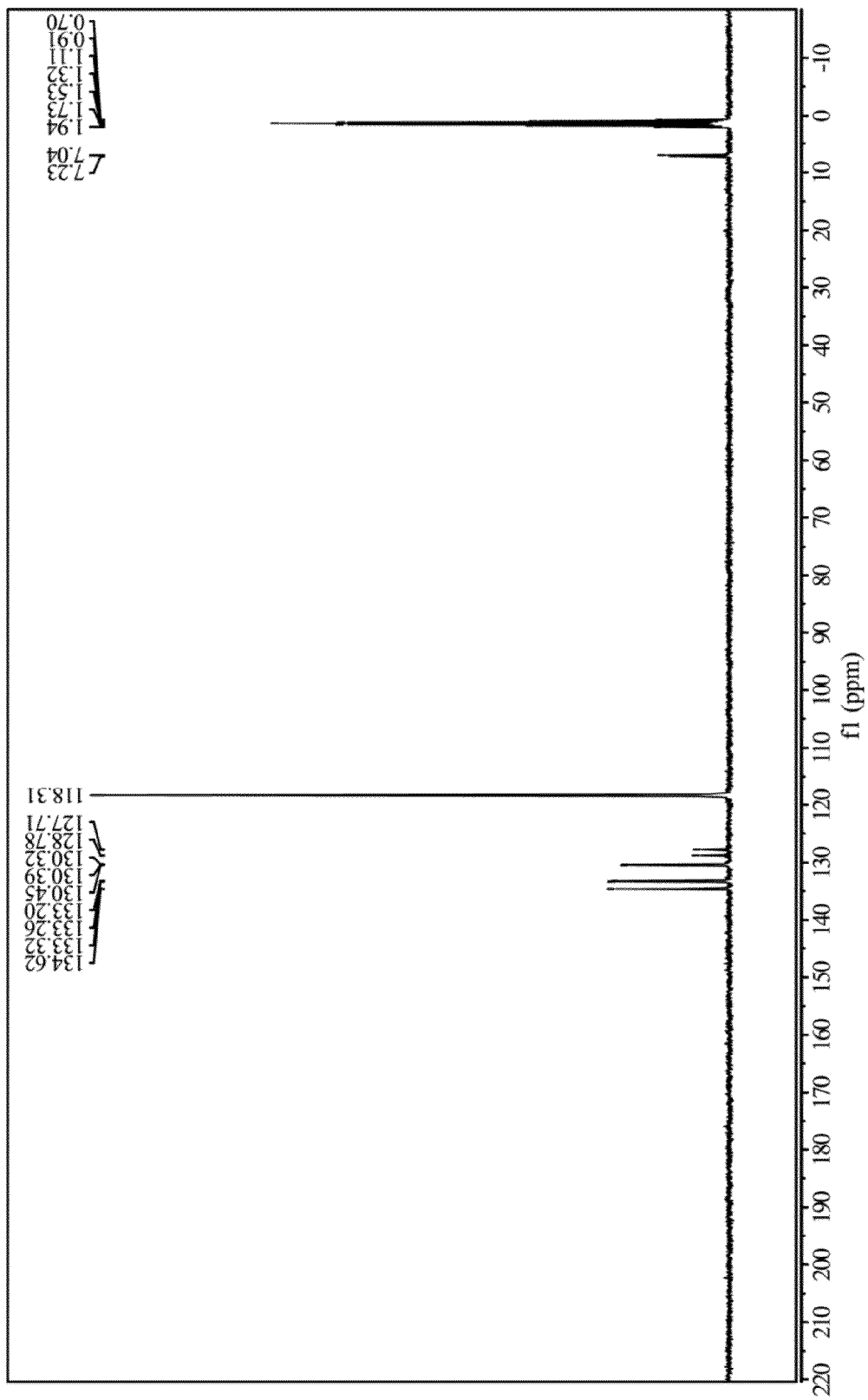
FIG. 23 is a $^{13}$C NMR spectrum of [PPN][MoO$_4$SiEt$_3$] in CD$_3$CN at 25° C.
Figure 24:
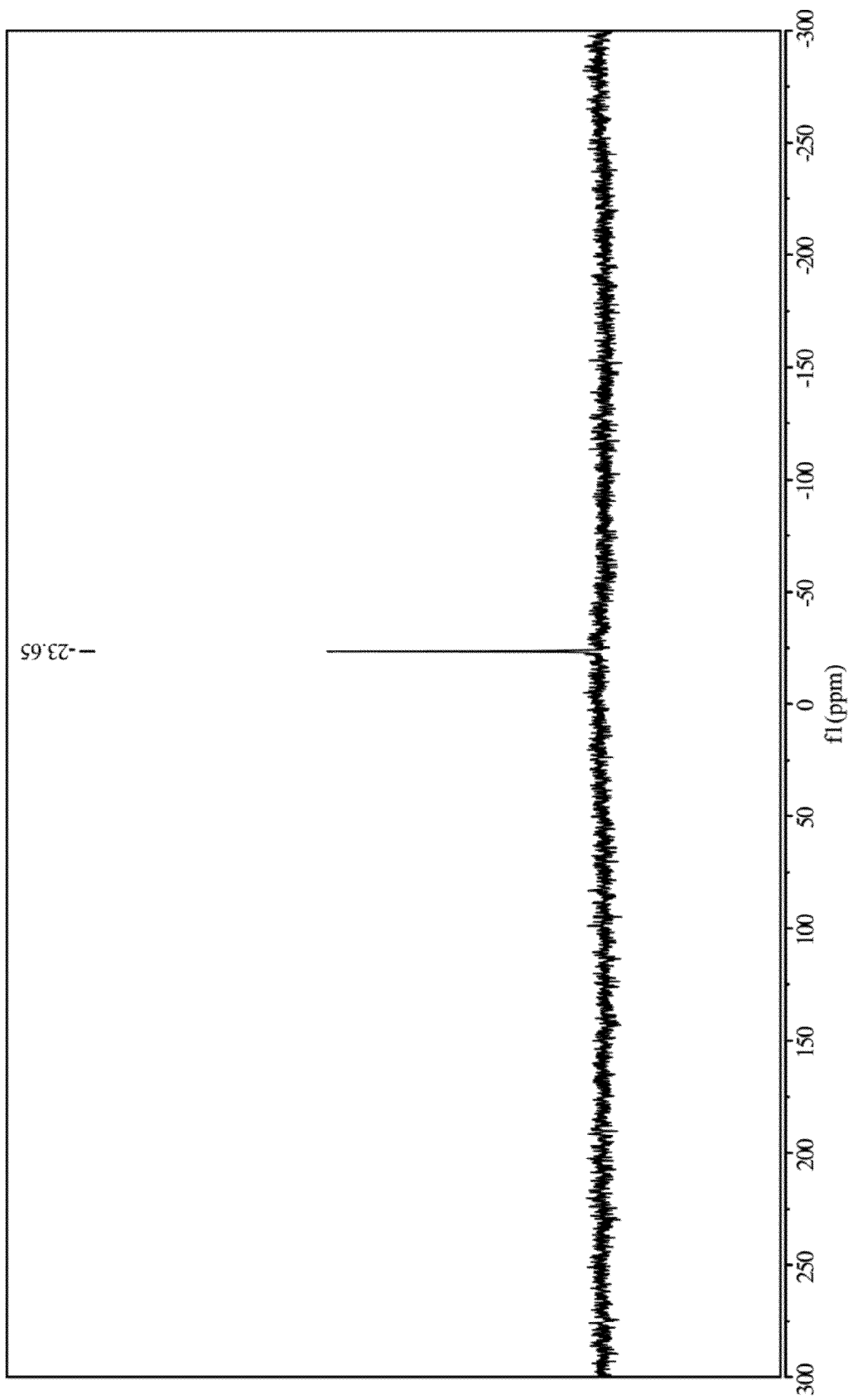
FIG. 24 is a $^{95}$Mo NMR spectrum of [PPN][MoO$_4$SiEt$_3$] in CD$_3$CN at 25° C.
Figure 25:
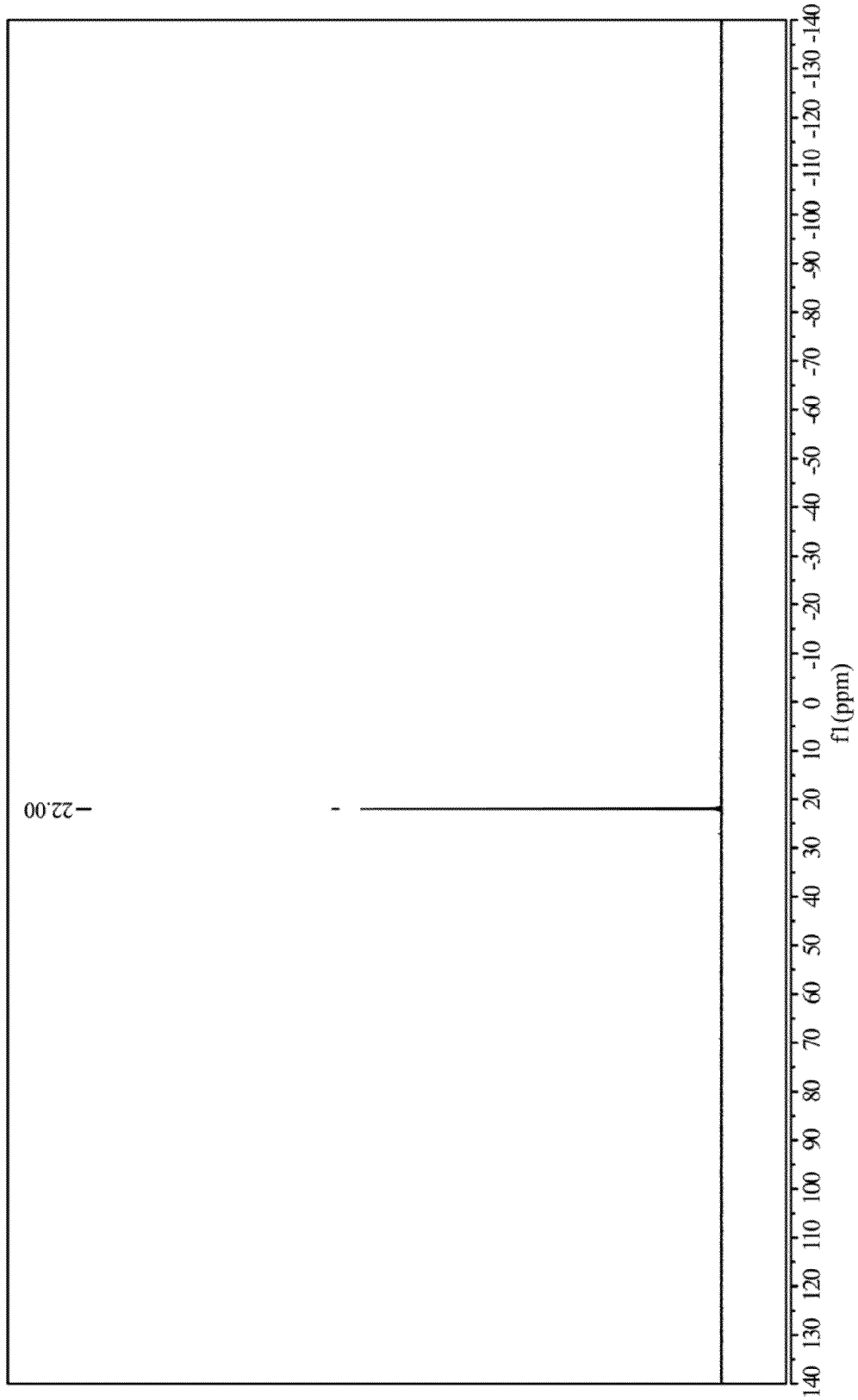
FIG. 25 is a $^{31}$P NMR spectrum of [PPN][MoO$_4$SiEt$_3$] in CD$_3$CN at 25° C.
Figure 26:
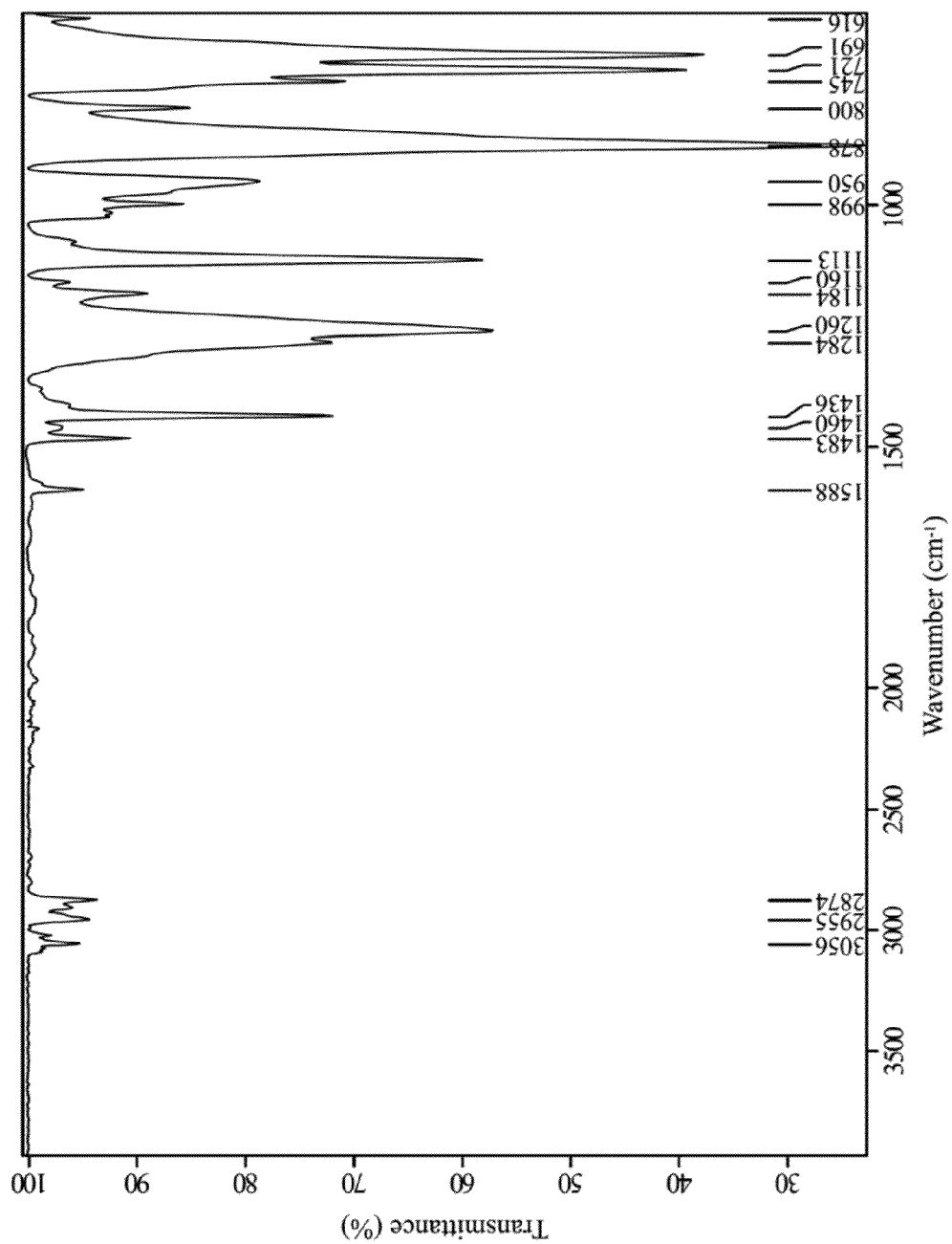
FIG. 26 is an ATR-IR spectrum of [PPN][MoO$_4$SiEt$_3$].

FIG. 16 shows $^1$H NMR of the crude reaction mixture containing [PPN][OCHO] and [PPN][MoO$_4$SiEt$_3$] in CD$_3$CN at 25° C.

Characterization of [PPN][OCHO] (FIGS. 17-21)

$^1$H NMR (CD$_3$CN, 25° C., 400.1 MHz) δ: 8.73 (s, 1 H, $^1$J$_{CH}$=86.1 Hz), 7.66 (6 H, m), 7.57 (12 H, m), 7.48 (12 H, m) ppm.

$^{13}$C{$^1$H} NMR (CD$_3$CN, 25° C., 100.6 MHz) δ: 166.4 (s), 134.6 (s), 133.2 (m), 130.4 (m), 128.2 ($^1$JPC=108 Hz) ppm.

$^{31}$P{$^1$H} NMR (CD$_3$CN, 25° C., 162.0 MHz) δ: 22.01 ppm.

ATR-IR: 3056, 2594, 1600 (vs), 1584, 1482, 1435, 1365, 1333, 1287, 1264, 1186, 1162, 1111, 1026, 997, 797, 765, 745, 722, 692, 664, 616 cm$^{-1}$

Elemental analysis [%] found (calculated for C$_{37}$H$_{31}$NO$_2$P$_2$): C, 73.43 (76.15); H, 4.96 (5.35); N, 2.28 (2.40).

Characterization of [PPN][MoO$_4$SiEt$_3$] (FIGS. 22-26)

$^1$H NMR (CD$_3$CN, 25° C., 400.1 MHz) δ: 7.66 (6 H, m), 7.58 (12 H, m), 7.48 (12 H, m), 0.95 (9 H,t, $^3$J$_{HH}$=7.9 Hz), 0.55 (6 H, q, $^3$J$_{HH}$=7.9 Hz) ppm.

$^{13}$C{$^1$H} NMR (CD$_3$CN, 25° C., 100.6 MHz) δ: 134.6 (s), 133.2 (m), 130.4 (m), 128.2 (d, $^1$JPC=108 Hz), 7.23 (s), 7.04 (s) ppm.

$^{95}$Mo NMR (CD$_3$CN, 25° C., 26.1 MHz) δ: −23.65 ppm.

$^{31}$P{$^1$H} NMR (CD$_3$CN, 25° C., 162.0 MHz) δ: 22.00 ppm.

ATR-IR: 3056, 2955, 2874, 1588, 1483, 1460, 1436, 1284, 1260, 1184, 1160, 1113, 998, 950, 878 (vs), 800, 745, 721, 691, 616 cm$^{-1}$

Elemental analysis [%] found (calculated for C$_{42}$H$_{45}$MoNO$_4$P$_2$Si): C, 61.94 (61.99); H, 5.30 (5.57); N, 1.64 (1.72).

Stability Studies on [PPN]$_2$[MoO$_3$($\kappa^2$-CO$_3$)]

Thermal Stability of [PPN]$_2$[MoO$_3$($\kappa^2$-CO$_3$)]

In the solid state: A small amount (ca. 30 mg) of [PPN]$_2$[MoO$_3$($\kappa^2$-CO$_3$)] were placed in a Schlenk flask and brought outside the glovebox. The flask was heated under dynamic vacuum in an oil bath at 70° C. for 1 hour. The resulting solid was analyzed by ATR-IR, showing an identical trace to the initial material with no decomposition or decrease in the carbonyl band.

Figure 27:
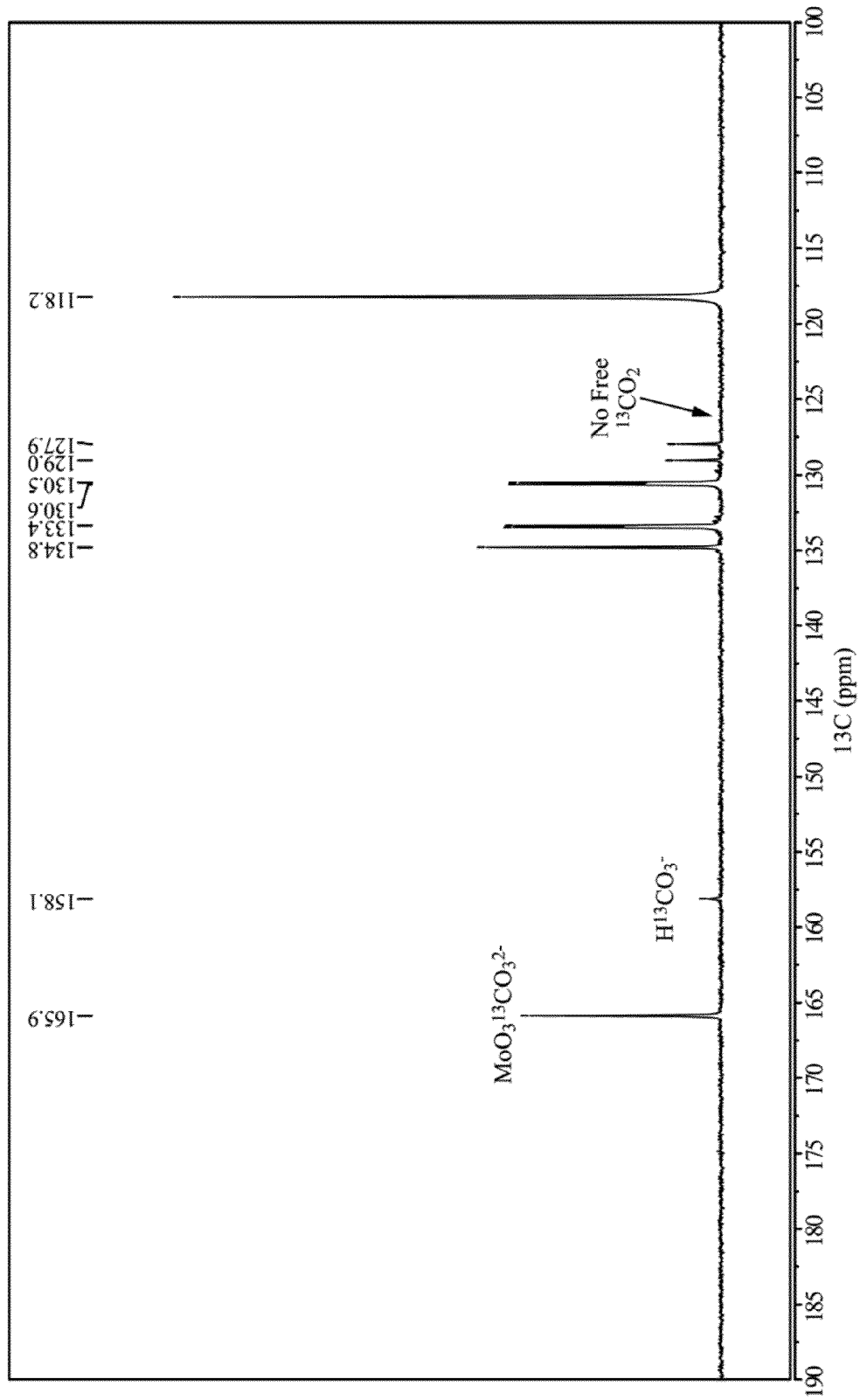
FIG. 27 is a $^{13}$C NMR spectrum of [PPN]$_2$[MoO$_3$(κ$^2$-$^{13}$CO$_3$)] in CD$_3$CN at 56° C.

In solution: 30 mg of [PPN]$_2$[MoO$_3$($\kappa^2$-$^{13}$CO$_3$)] were dissolved in ca. 0.6 mL of CD$_3$CN and transferred to an NMR tube glass blown onto a 14/20 female adapter. A vacuum adapter was added, and the sealed system was brought outside the box. The solution was frozen in liquid nitrogen, the system was evacuated, then the tube was flame sealed. $^{13}$C NMR spectra (e.g., FIG. 27) were taken at room temperature, 38° C. and 56° C. No free $^{13}$CO$_2$ was observed in solution. In contrast to the broad signal observed in the presence of excess $^{13}$CO$_2$, the signal of [MoO$_3$($\kappa^2$-$^{13}$CO$_3$)]$^{2-}$ remained sharp, indicating that no chemical exchange was occurring.

Addition of Water to [PPN]$_2$[MoO$_3$($\kappa^2$-$^{13}$CO$_3$)] Monitored by $^{13}$C NMR

Figure 28:
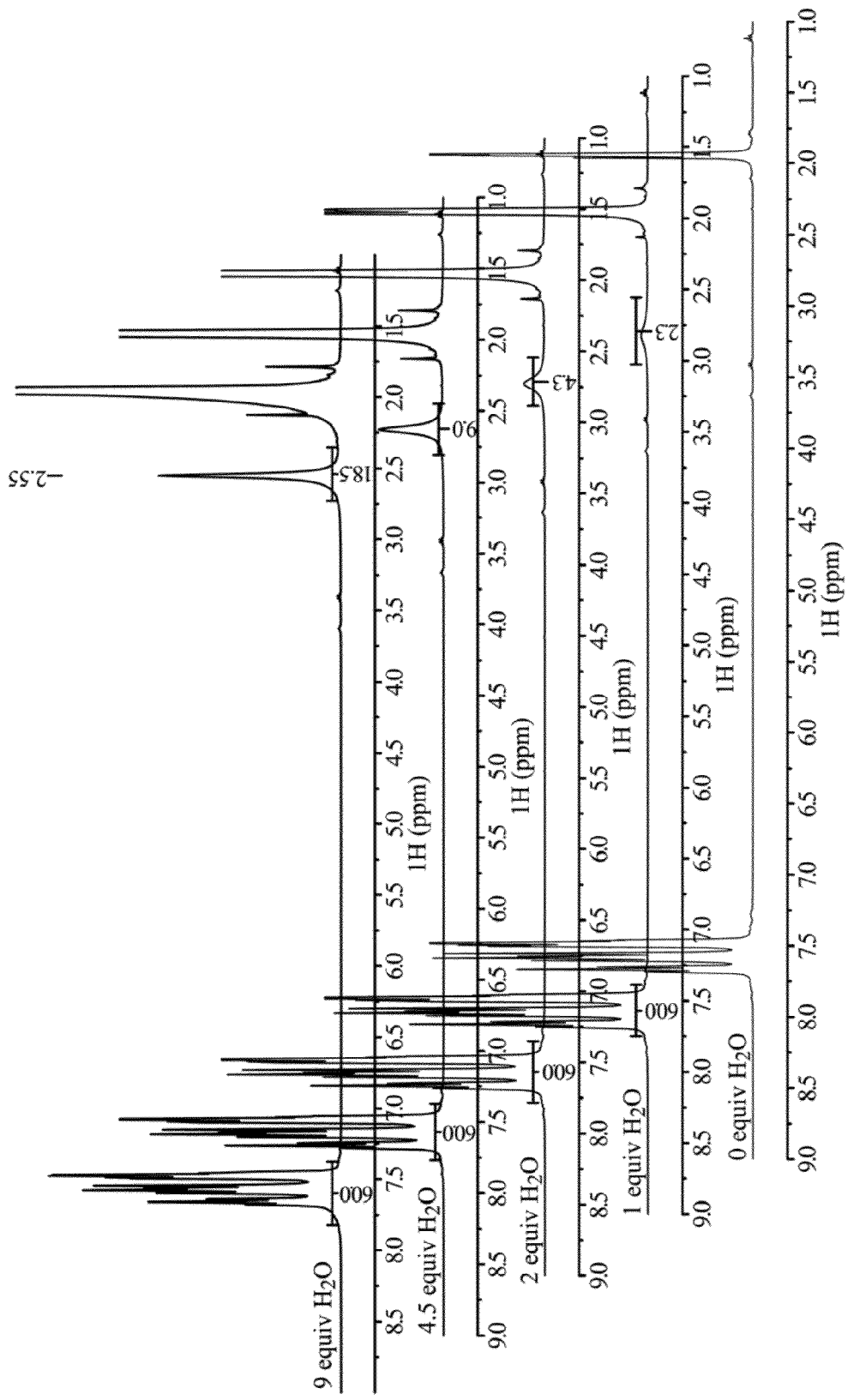
FIG. 28 is a series of $^1$H NMR spectra of the [PPN]$_2$[MoO$_3$(κ$^2$-$^{13}$CO$_3$)] solution with increasing water content.
Figure 29:
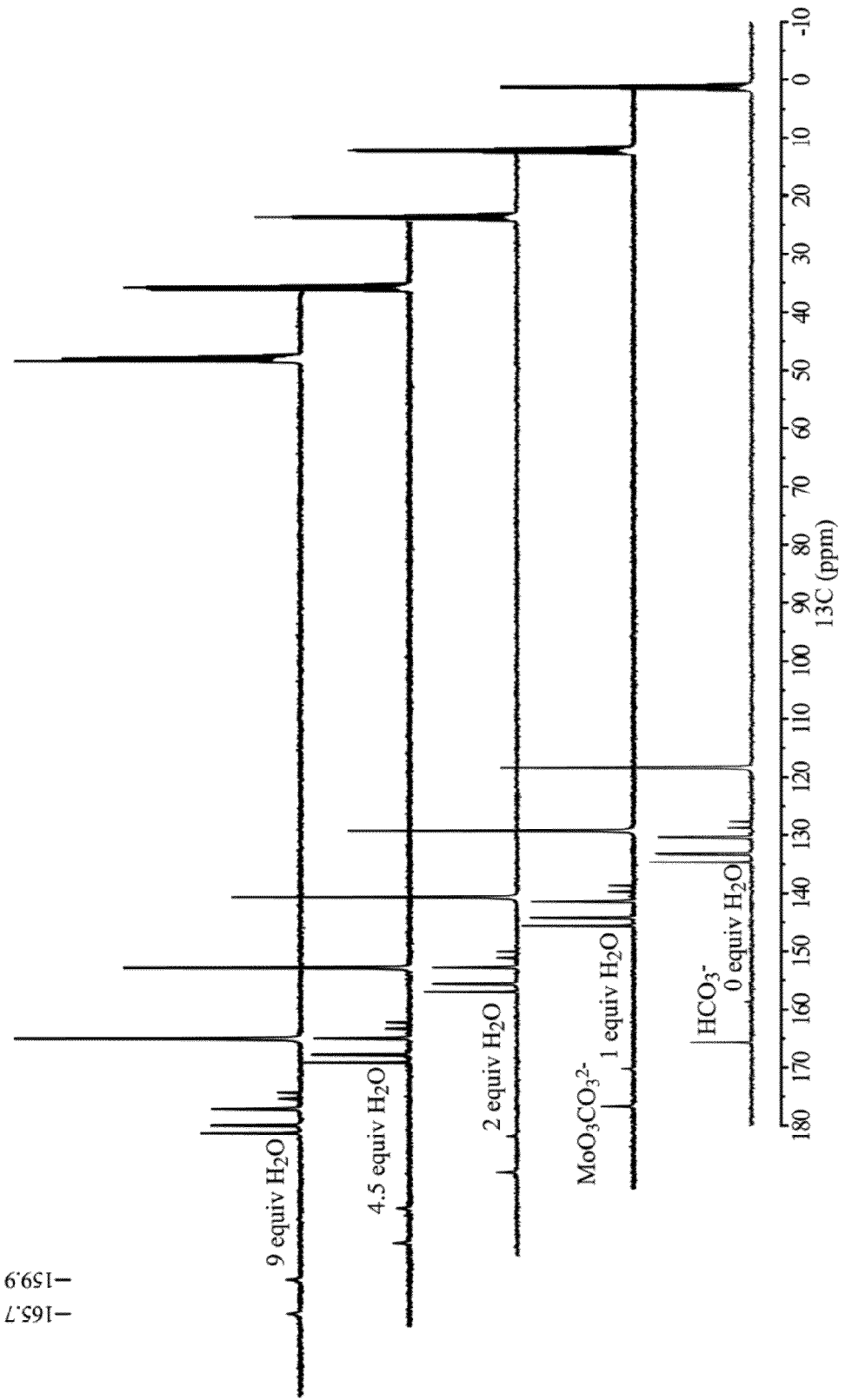
FIG. 29 is a series of $^{13}$C NMR spectra of the [PPN]$_2$[MoO$_3$(κ$^2$-$^{13}$CO$_3$)] solution with increasing water content.

[PPN]$_2$[MoO$_3$($\kappa^2$-$^{13}$CO$_3$)] (26 mg, 0.02 mmol, 1 equiv) was dissolved in ca. 0.6 mL of CD$_3$CN, transferred to an NMR tube, and capped with a septum. A stock solution of H$_2$O in CH$_3$CN was prepared by adding 36 μL H$_2$O to ca. 0.97 mL CH$_3$CN. 1H NMR and $^{13}$C NMR spectra of the initial sample were taken. Stoichiometric amounts of water were added via microsyringe from the stock solution in 100 μL increments. Each 100 μL of the stock solution contain 0.02 mmol (1 equiv) H$_2$O. $^1$H NMR and $^{13}$C NMR spectra were collected after the addition of 1, 2, 4.5 and 9 equiv of water. The $^1$H NMR spectra were used to confirm the stoichiometry (FIG. 28). The $^{13}$C NMR spectra were diagnostic for the stability of the [PPN]$_2$[MoO$_3$($\kappa^2$-$^{13}$CO$_3$)] (FIG. 29).

Although in a decreased amount, $[PPN]_2[MoO_3(\kappa^2\text{-}^{13}CO_3)]$ is present in solution even after the addition of 9 equivalents of water.

Addition of Water to $[PPN]_2[MoO_3(\kappa^2\text{-}CO_3)]$ monitored by ATR-IR

Figure 30:
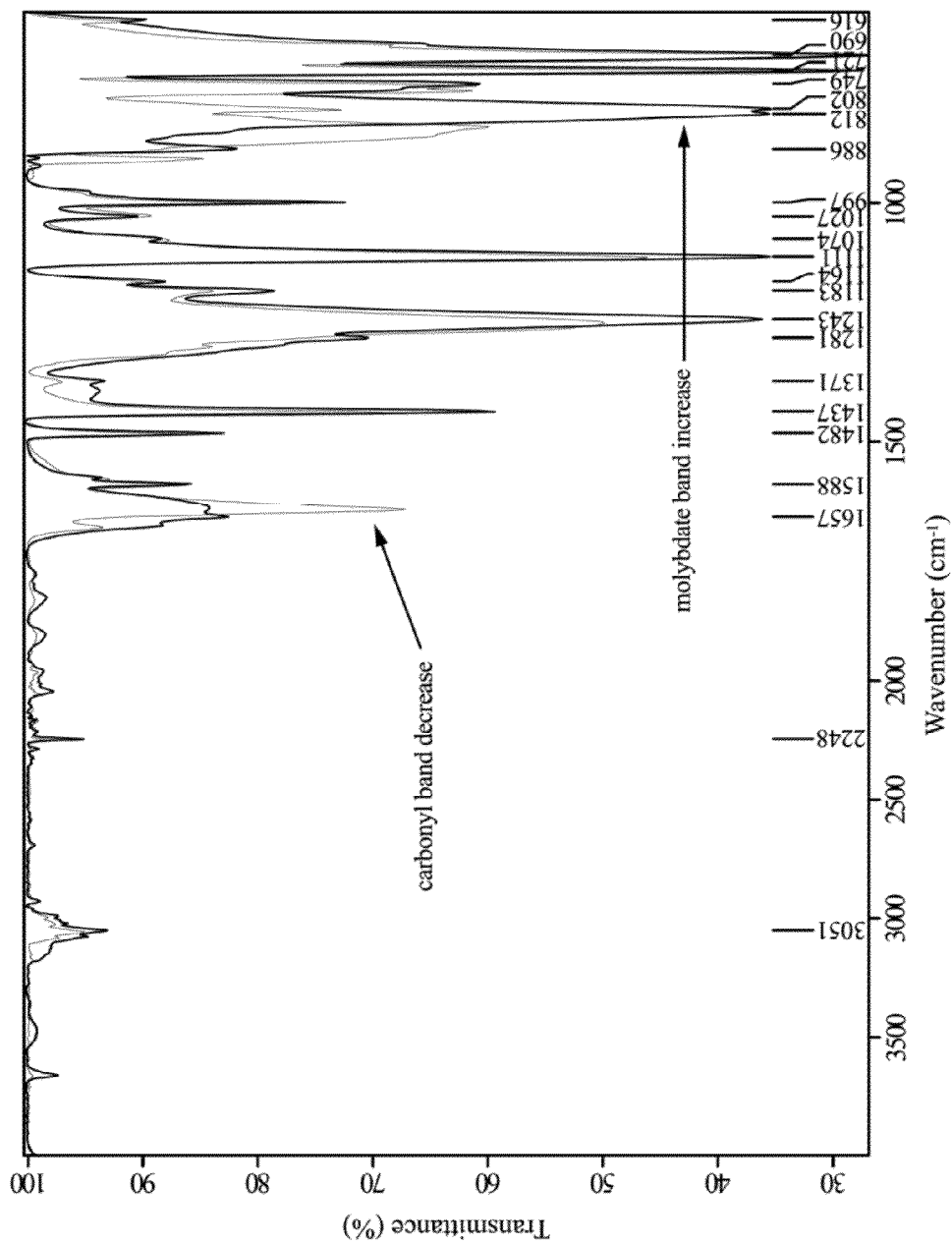
FIG. 30 is ATR-IR spectrum of [PPN]$_2$[MoO$_3$(k$^2$-CO$_3$)] before and after treatment with water showing a carbonyl ban decrease and a molybdate band increase.

A small amount of $[PPN]_2[MoO_3(\kappa^2\text{-}CO_3)]$ (20 mg, 0.0156 mmol) was dissolved in 1 mL $CH_3CN$ in a vial that was then capped with a septum. The vial was taken outside the glovebox where 10 μL (10 mg, 0.555 mmol) of water were injected using a microsyringe. The solution was stirred for ca. 10 min, the volatiles were removed, and the residue analyzed b ATR-IR. FIG. 30 shows ATR-IR of $[PPN]_2[MoO_3(\kappa^2\text{-}CO_3)]$ before and after treatment with water showing a carbonyl ban decrease and a molybdate band increase.

Hygroscopy of $[NEt_4]_2[MoO_3(\kappa^2\text{-}CO_3)]$ Monitored by ATR-IR

Figure 31:
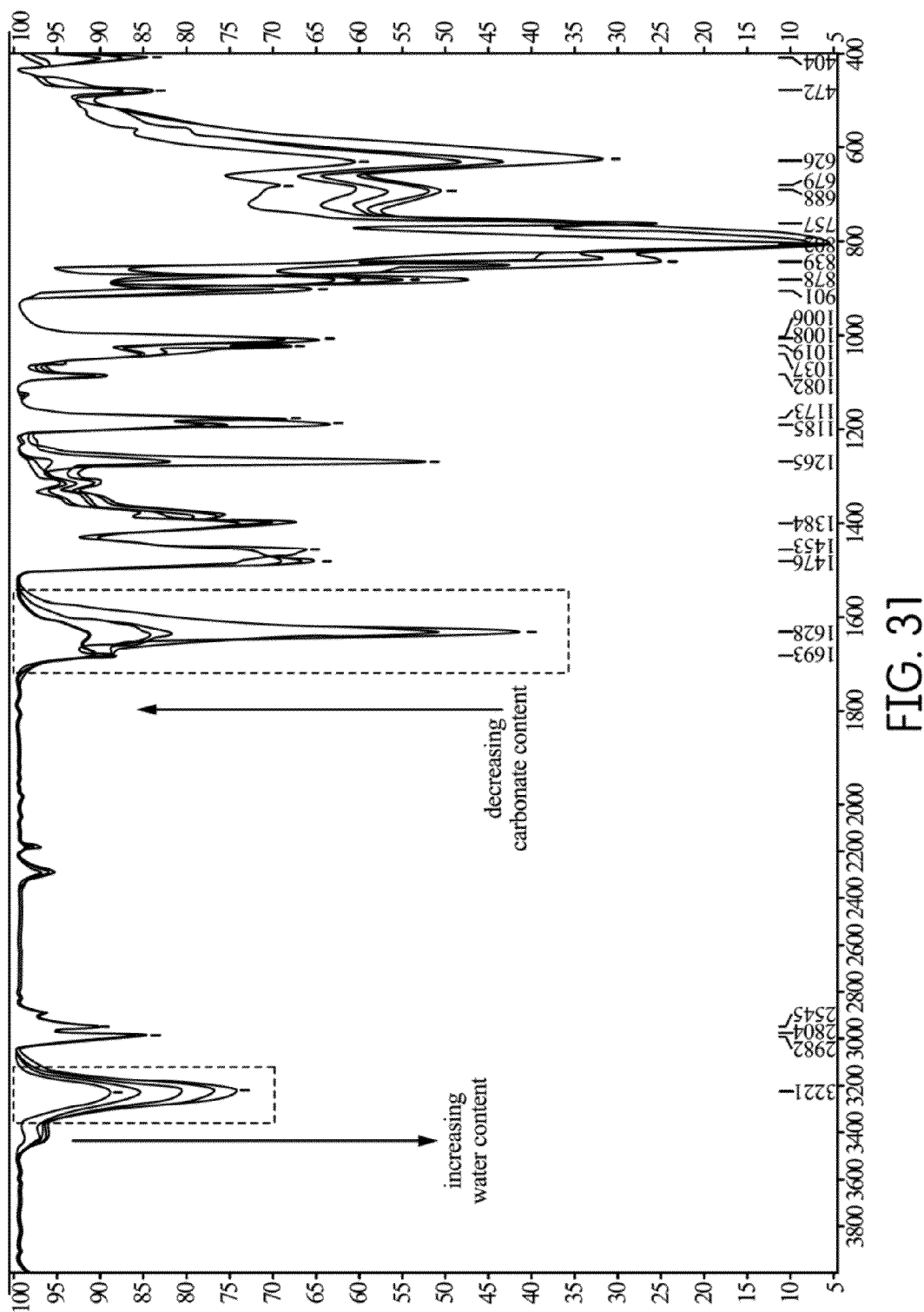
FIG. 31 depicts an evolution of the ATR-IR spectrum of [NEt4]2[MoO3(k2-CO3)] over the course of 15 minutes in air.

A small amount (ca. 5 mg) of $[NEt_4]_2[MoO_3(\kappa^2\text{-}CO_3)]$ was placed on the ATR plate and the IR spectrum of this sample was recorded. Additional spectra of the same sample were recorded every 2-3 minutes for a total of 15 minutes, time during which the sample remained in air on the ATR plate and was absorbing atmospheric moisture. The overlay below shows the correlation between the disappearance of the carbonate band and the growth of the broad water OH band. The end product displays bands in the metal oxo region of the spectrum corresponding to molybdate and dimolybdate. See FIG. 31.

Figure 32:
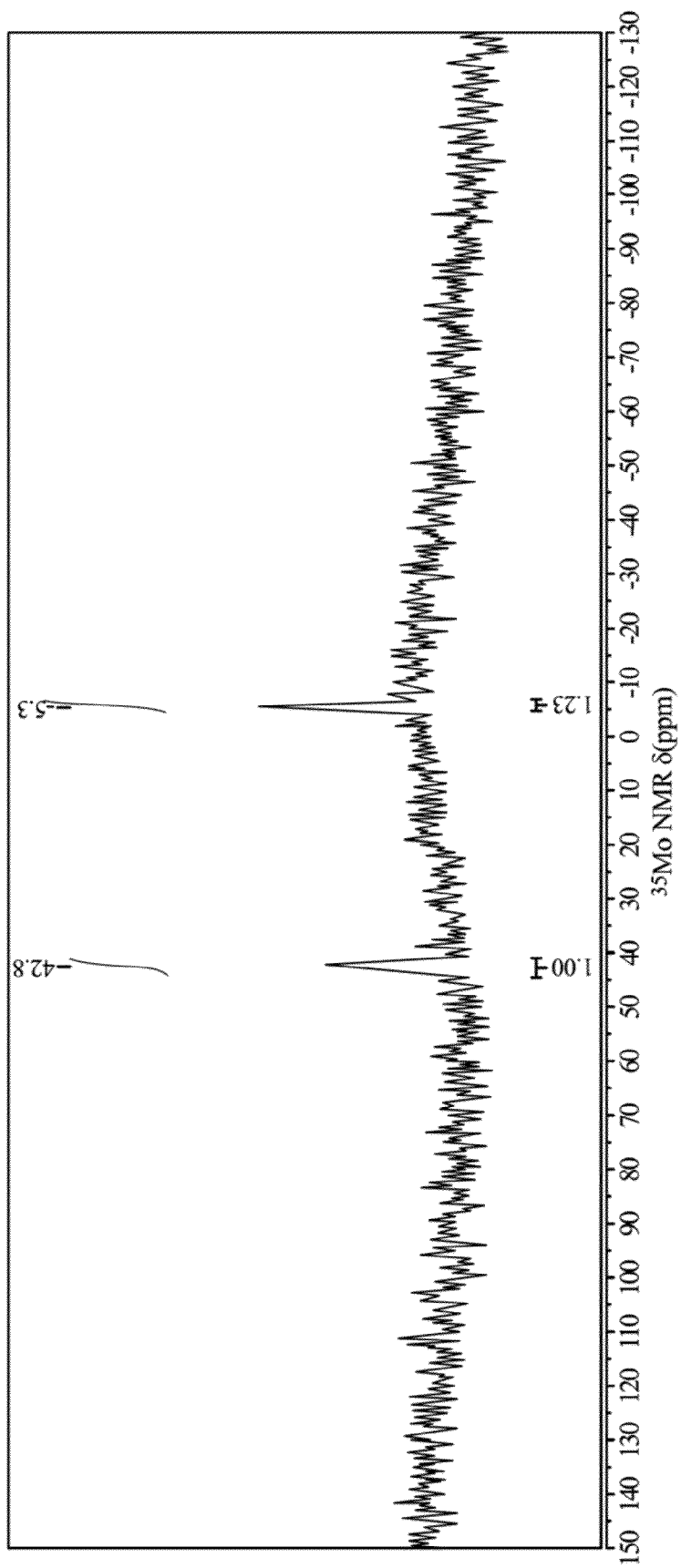
FIG. 32 is a $^{95}$Mo NMR spectrum of the crude reaction mixture at 25 C

Formation of $[PPN]_2[MoO_3(\kappa^2\text{-}CO_3)]$ in Wet Aerobic Conditions $[PPN]_2[MoO_4]$ (100 mg, 0.08 mmol, 1 equiv) was dissolved in non-degassed ACS grade acetonitrile (2 mL) under air. Carbon dioxide (40 mL, 1.64 mmol, 20 equiv) was bubbled through the stirring molybdate solution. The reaction was allowed to stir open to air for 10 minutes, after which an aliquot was taken for NMR analysis. The $^{95}Mo$ NMR spectrum of the crude reaction mixture indicates formation of $[PPN]_2[MoO_3(\kappa^2\text{-}CO_3)]$ and $[PPN]_2[Mo_2O_7]$ in a 1.6:1 ratio. See FIG. 32.

$^{13}C$-Labeling Experiments

Figure 33:
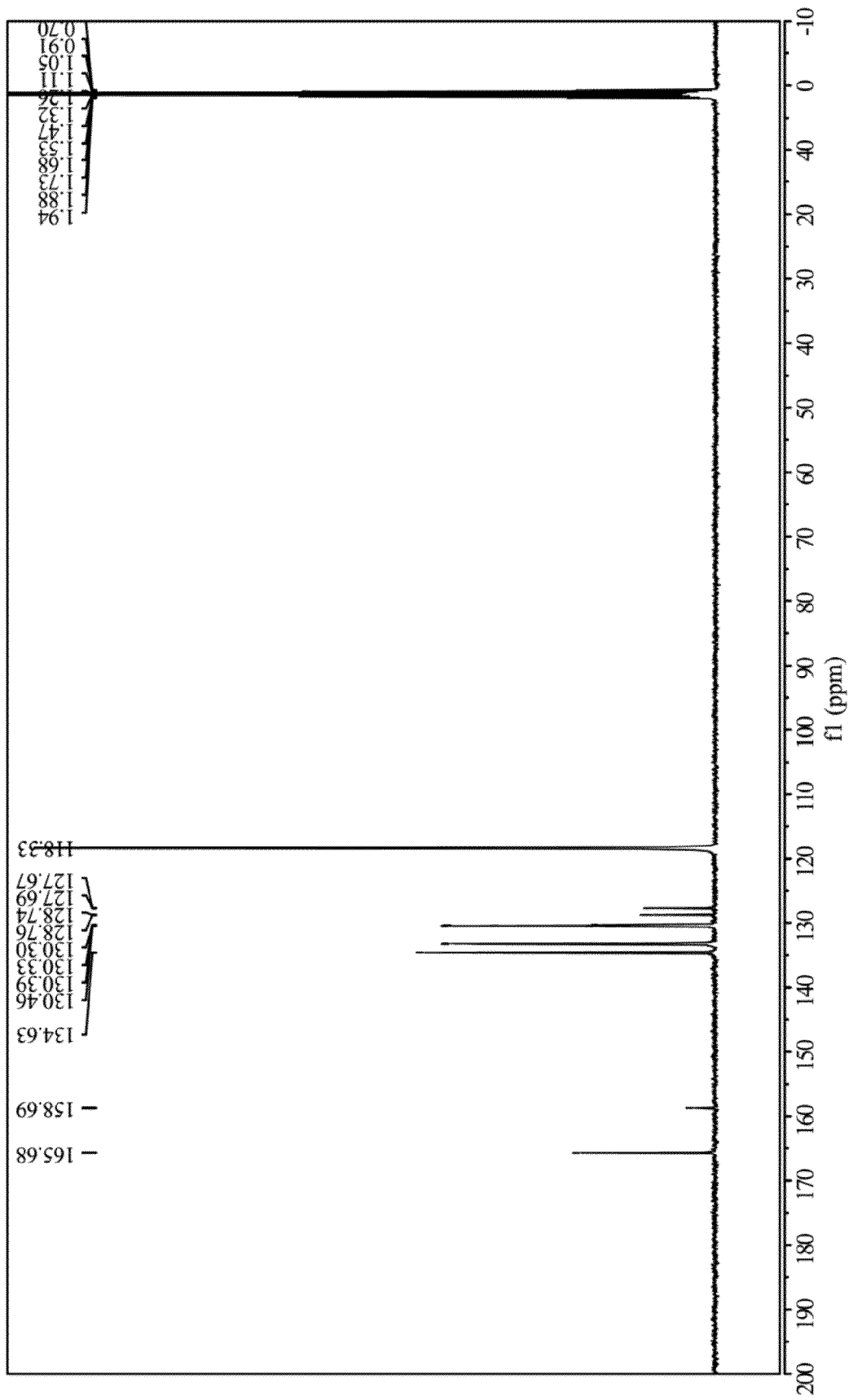
FIG. 33 is a $^{13}$C NMR spectrum of the initial reaction mixture.
Figure 34:
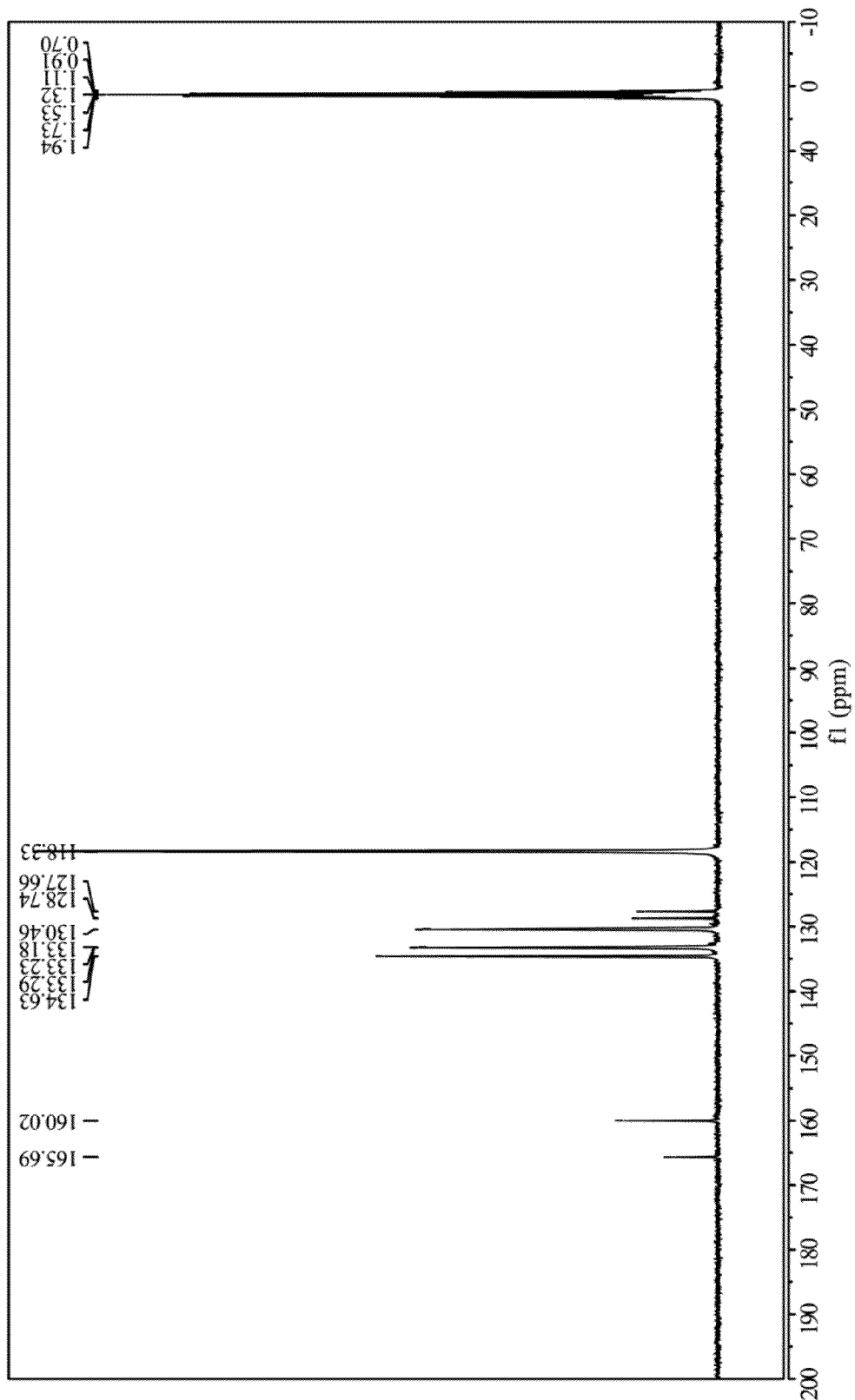
FIG. 34 is a $^{13}$C NMR spectrum of the initial reaction mixture after [PPN][HCO$_3$] was added.

Identifying $HCO_3^-$ in the $^{13}C$ NMR of $[PPN]_2[MoO_3(\kappa^2\text{-}^{13}CO_3)]$ (FIGS. 33-34)

$[PPN]_2[MoO_4]$ (30.4 mg, 0.025 mmol, 1 equiv) was dissolved in ca. 0.6 mL of $CD_3CN$, transferred to an NMR tube, and capped with a septum. The tube was taken outside the glovebox and the solution submitted to 3 freeze-pump-thaw cycles. $^{13}CO_2$ (0.6 mL, 0.025 mmol, 1 equiv) was added by syringe, after which the tube was shaken vigorously. $^{13}C$ NMR of the reaction mixture was taken, then the tube was brought back into the glovebox where a small amount of $[PPN][HCO_3]$ was added to the solution. $^{13}C$ NMR of this mixture was taken, confirming the identity of the upheld carbonate peak.

Figure 35:
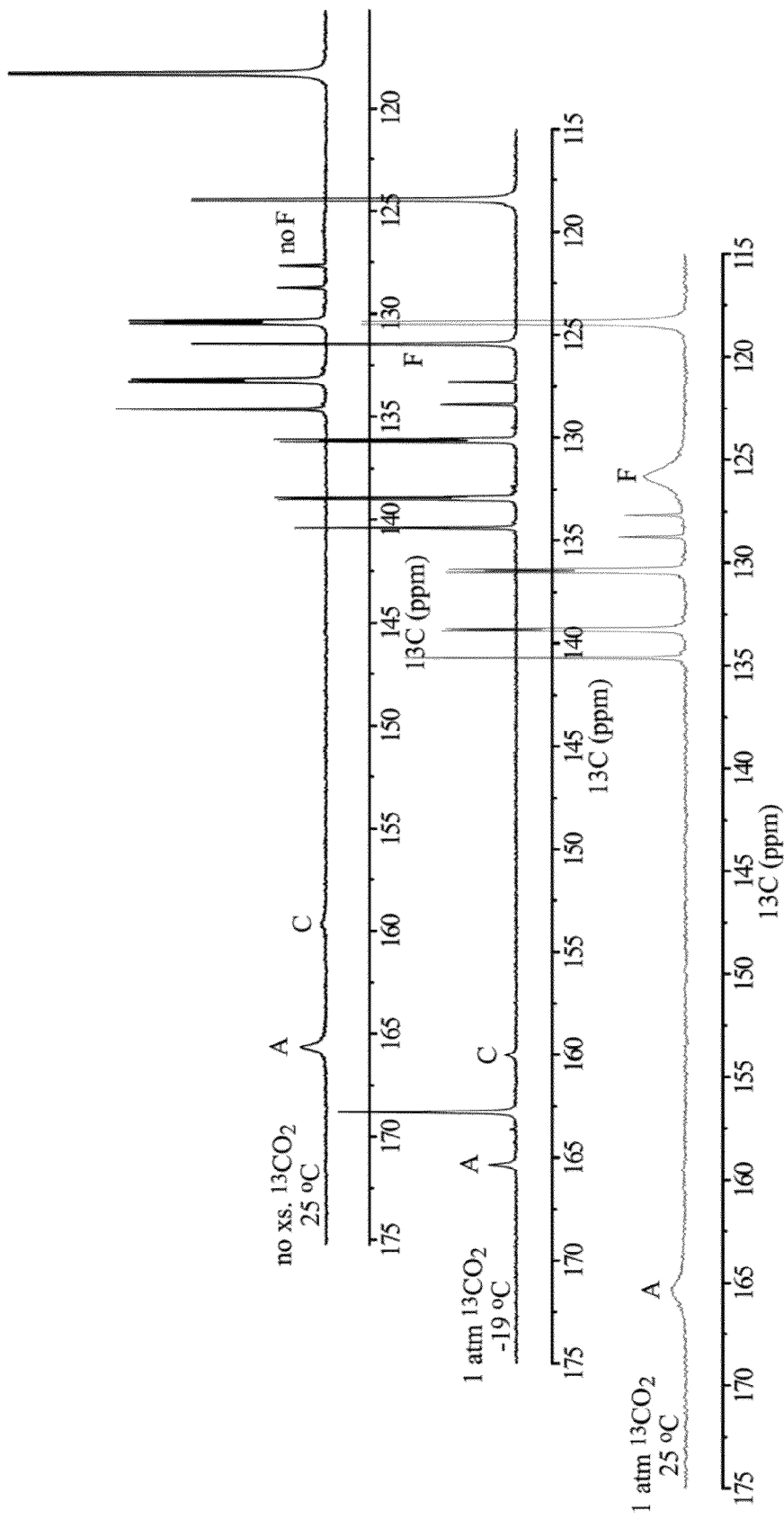
FIG. 35 is a $^{13}$C NMR spectrum of [PPN]$_2$[MoO$_4$] under 1 atmosphere of $^{13}$CO$_2$ and after removing the $^{13}$CO$_2$.

Product Distribution Under 1 Atmosphere of $^{13}CO_2$ $[PPN]_2[MoO_4]$ (30.4 mg, 0.025 mmol) was dissolved in ca. 0.6 mL of $CD_3CN$, and transferred to a J-Young NMR tube. The tube was brought outside the glovebox, and the solution was submitted to 3 freeze-pump-thaw cycles. After the sample warmed up to room temperature, $^{13}CO_2$ was introduced with a syringe. Only the amount of gas pulled in by the vacuum was introduced, and the solution was left to equilibrate for 1 minute while gently shaking the tube, after which the J-Young was sealed. $^{13}C$ NMR of this sample under 1 atmosphere of $^{13}CO_2$ is shown in FIG. 35, at room temperature and −19° C. (A: $[PPN]_2[MoO_3(\kappa^2\text{-}^{13}CO_3)]$, B: $[PPN]_2[MoO_2(\kappa^2\text{-}^{13}CO_3)_2]$, C: $[PPN][HCO_3]$, and F: free $^{13}CO_2$). The sample was then submitted to 3 freeze-pump-thaw cycles in order to remove the excess $^{13}CO_2$.

Product Distribution Under 3 Atmospheres of $^{13}CO_2$

Figure 36:
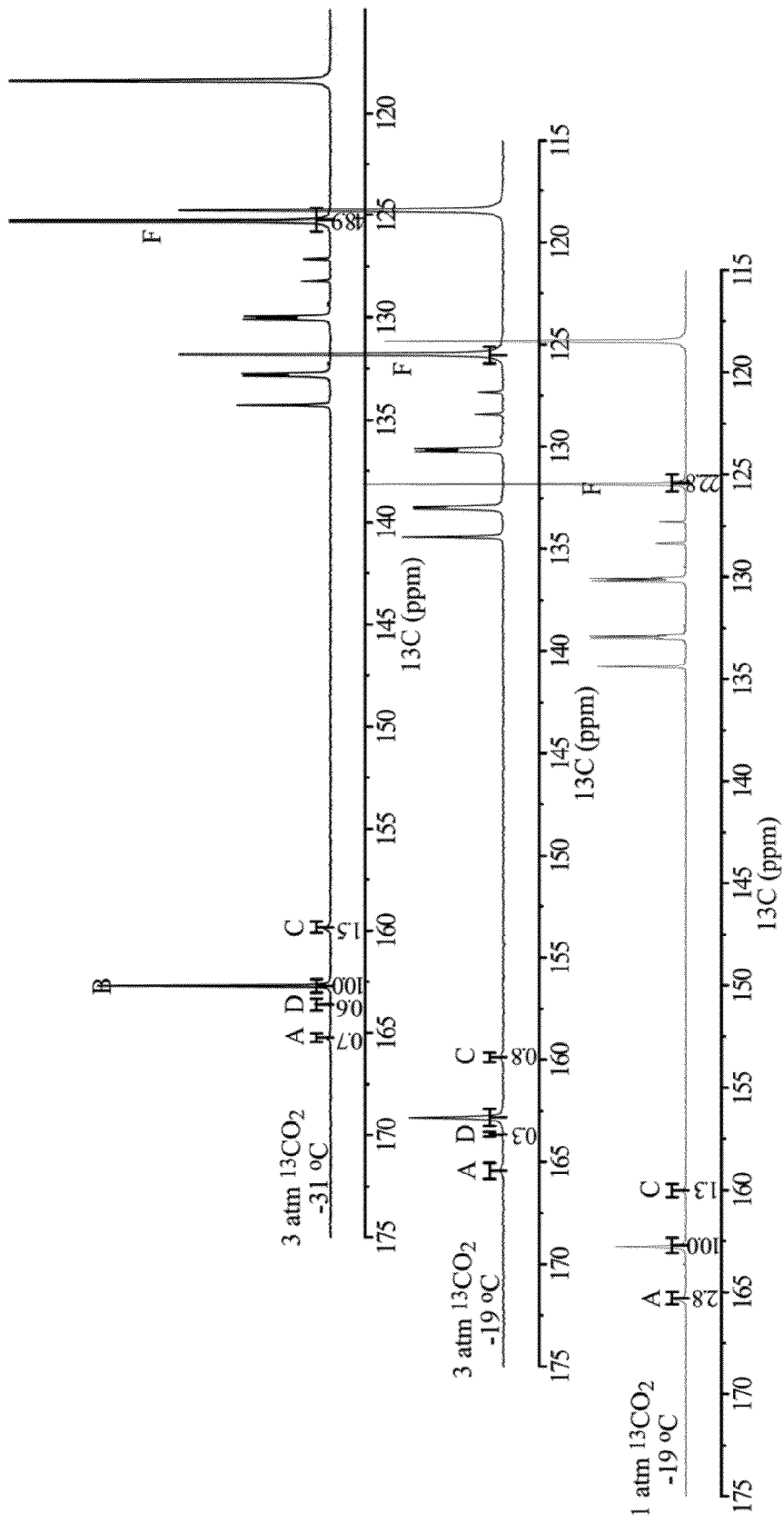
FIG. 36 is a series of $^{13}$C NMR spectra of [PPN]$_2$[MoO$_4$] under 1 atmosphere and 3 atmospheres of $^{13}$CO$_2$ at low temperature.
Figure 37:
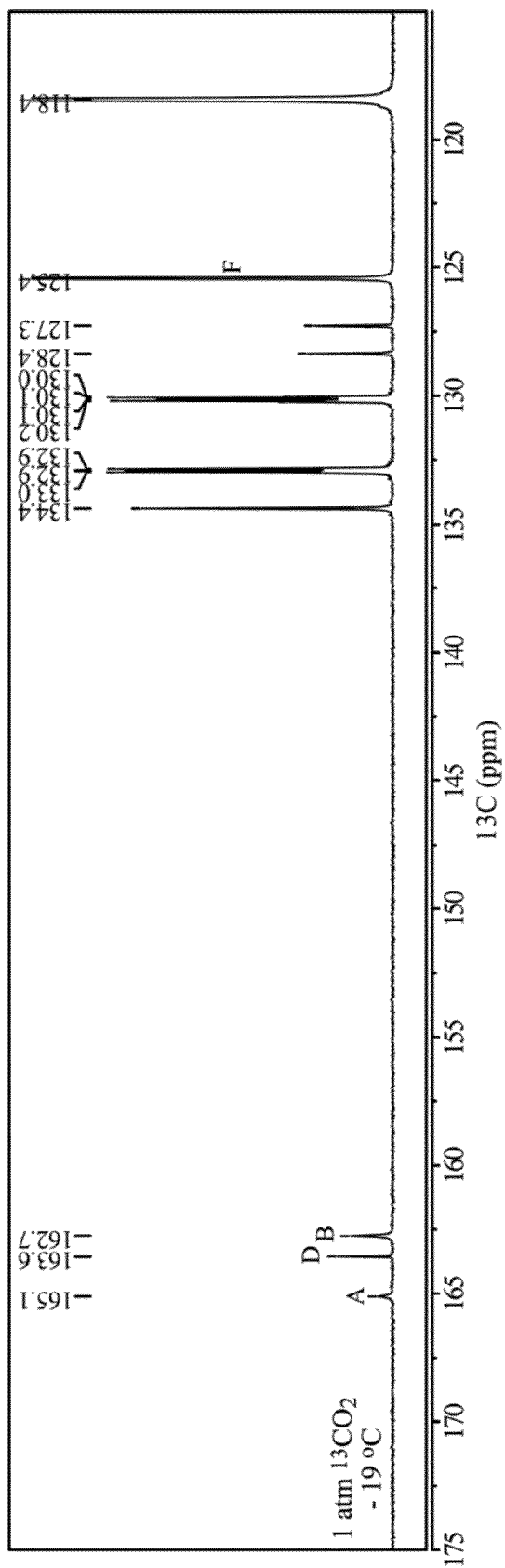
FIG. 37 is a $^{13}$C NMR spectrum of [PPN]$_2$[MoO$_7$] under 1 atmosphere of $^{13}$CO$_2$ at low temperature.

Inside the glovebox, $[PPN]_2[MoO_4]$ (35 mg, 0.028 mmol) was dissolved in ca. 0.6 mL of $CD_3CN$, and transferred to an NMR tube glass blown onto a 14/20 female adapter. A vacuum adapter was added, and the sealed system was brought outside the box. The solution was degassed using 5 freeze-pump-thaw cycles. The system was refilled with $^{13}CO2$ via syringe, then closed. The NMR tube was placed in liquid nitrogen and flame sealed. The pressure (3 atmospheres) was calculated based on the relative integration of the free $^{13}CO_2$ and the solvent at room temperature, as compared with the corresponding ratio of the sample prepared under 1 atmosphere as in the previous section. FIG. 36 shows $^{13}C$ NMR of $[PPN]_2[MoO_4]$ under 1 atmosphere and 3 atmospheres of $^{13}CO_2$ at low temperature (A: $[PPN]_2[MoO_3(\kappa^2\text{-}^{13}CO_3)]$, B: $[PPN]_2[MoO_2(\kappa^2\text{-}^{13}CO_3)_2]$, C: $[PPN][HCO_3]$ D: species likely due to binding of $^{13}CO_2$ to $[PPN]_2[Mo_2O_7]$ at low temperature under excess $^{13}CO_2$, as evidenced by the spectrum in FIG. 35, and F: free $^{13}CO_2$).

X-Ray Crystallographic Data

Figure 2:
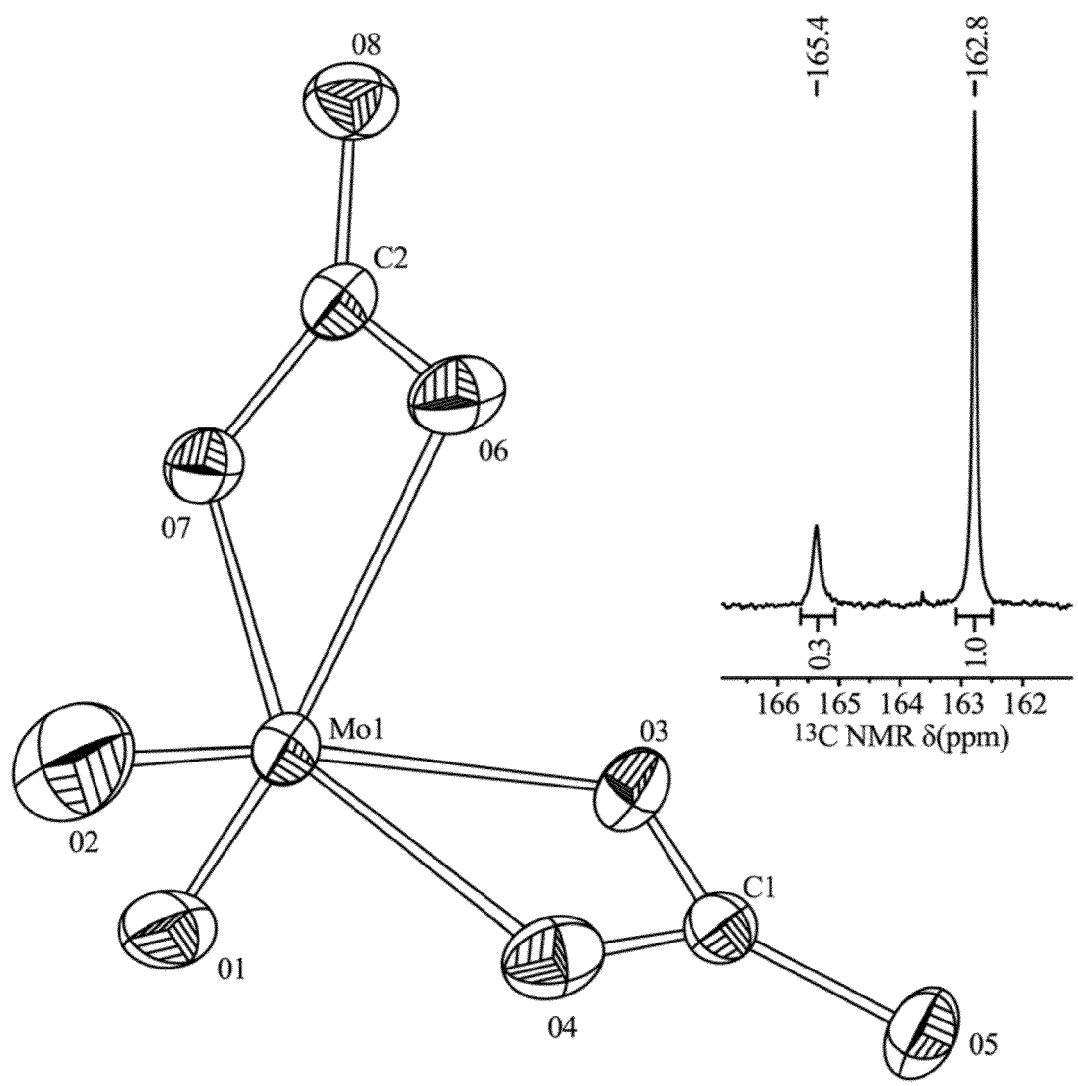
FIG. 2 is a $^{13}$C NMR spectrum showing the distribution of $[MoO_3(\kappa^2\text{-}CO_3)]^{2-}$ and $[MoO_2(\kappa^2\text{-}CO_3)_2]^{2-}$ at −19° C. under 1 atmosphere of $^{13}CO_2$ and a solid-state structure of $[PPN]_2[MoO_2(\kappa^2\text{-}CO_3)_2]$. (ellipsoids at the 50% probability level, cations and solvent molecules omitted for clarity). Representative interatomic distances [Angstroms] and angles [°]:C1-O3 1.302(4), C1-O4 1.352(4), C1-O5 1.228(4), C2-O6 1.303(3), C2-O7 1.358(3), C2-O8 1.223(3), Mo1-O1 1.695(2), Mo1-O2 1.705(3), Mo1-O3 2.198(2), Mo1-O4 2.024(2), Mo1-O6 2.175(2), Mo1-O7 2.0145(19); O3-C1-O4 110.4(2), O6-C2-O7 109.9(2).
Figure 3:
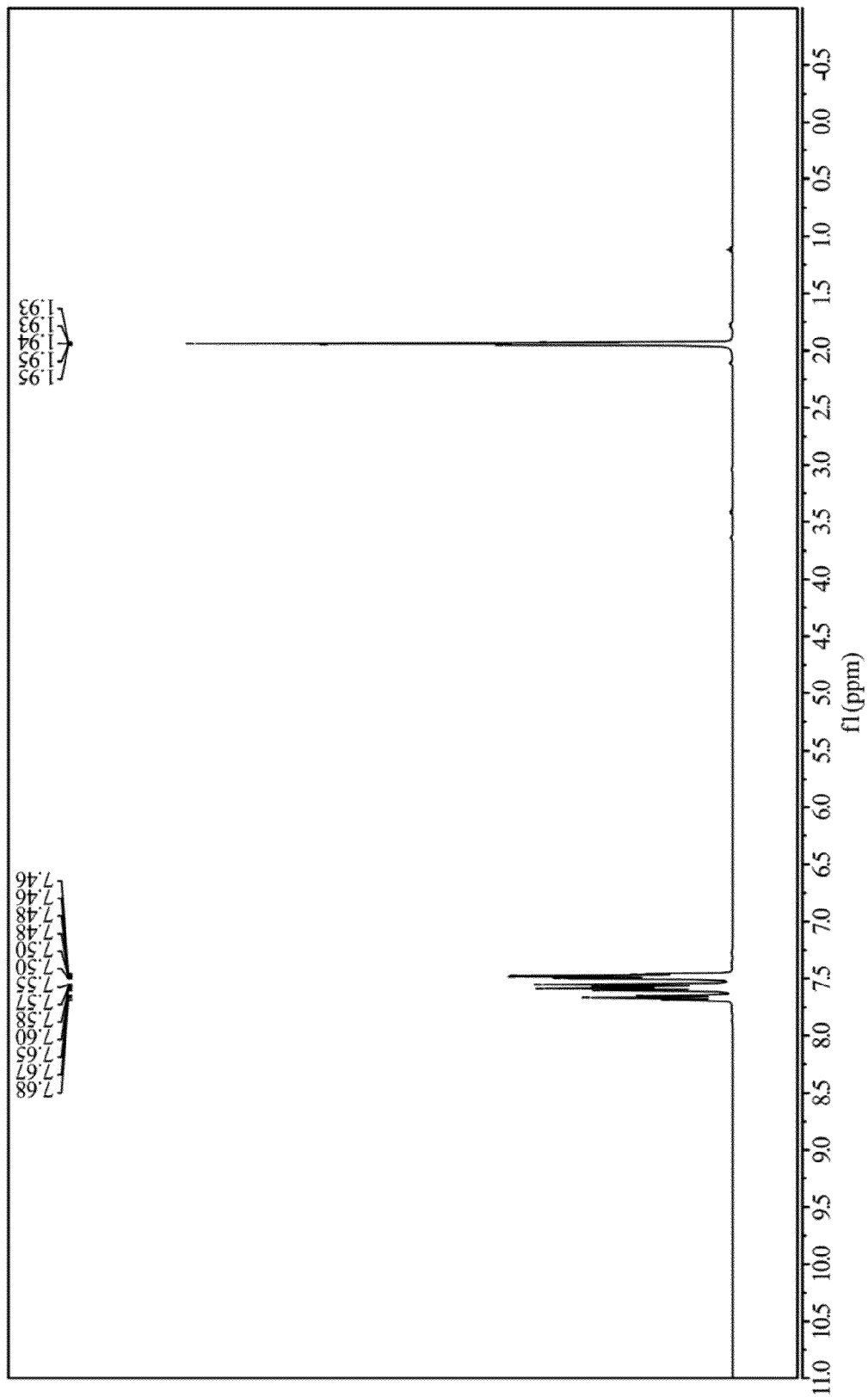
FIG. 3 is a $^1$H NMR spectrum of $[PPN]_2[MoO_4]$ in $CD_3CN$ at 25° C.
Figure 4:
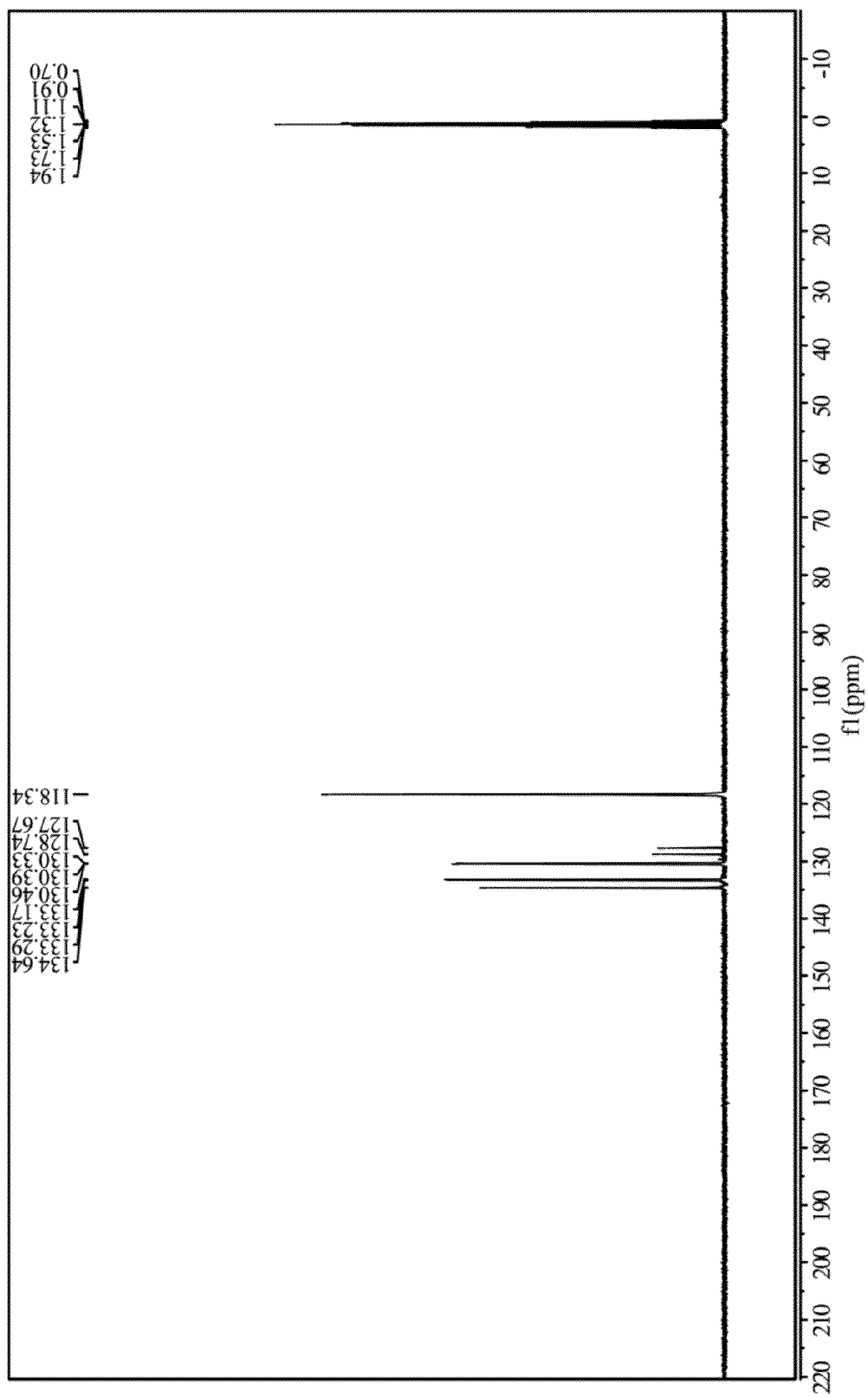
FIG. 4 is a $^{13}$C NMR spectrum of $[PPN]_2[MoO_4]$ in $CD_3CN$ at 25° C.
Figure 5:
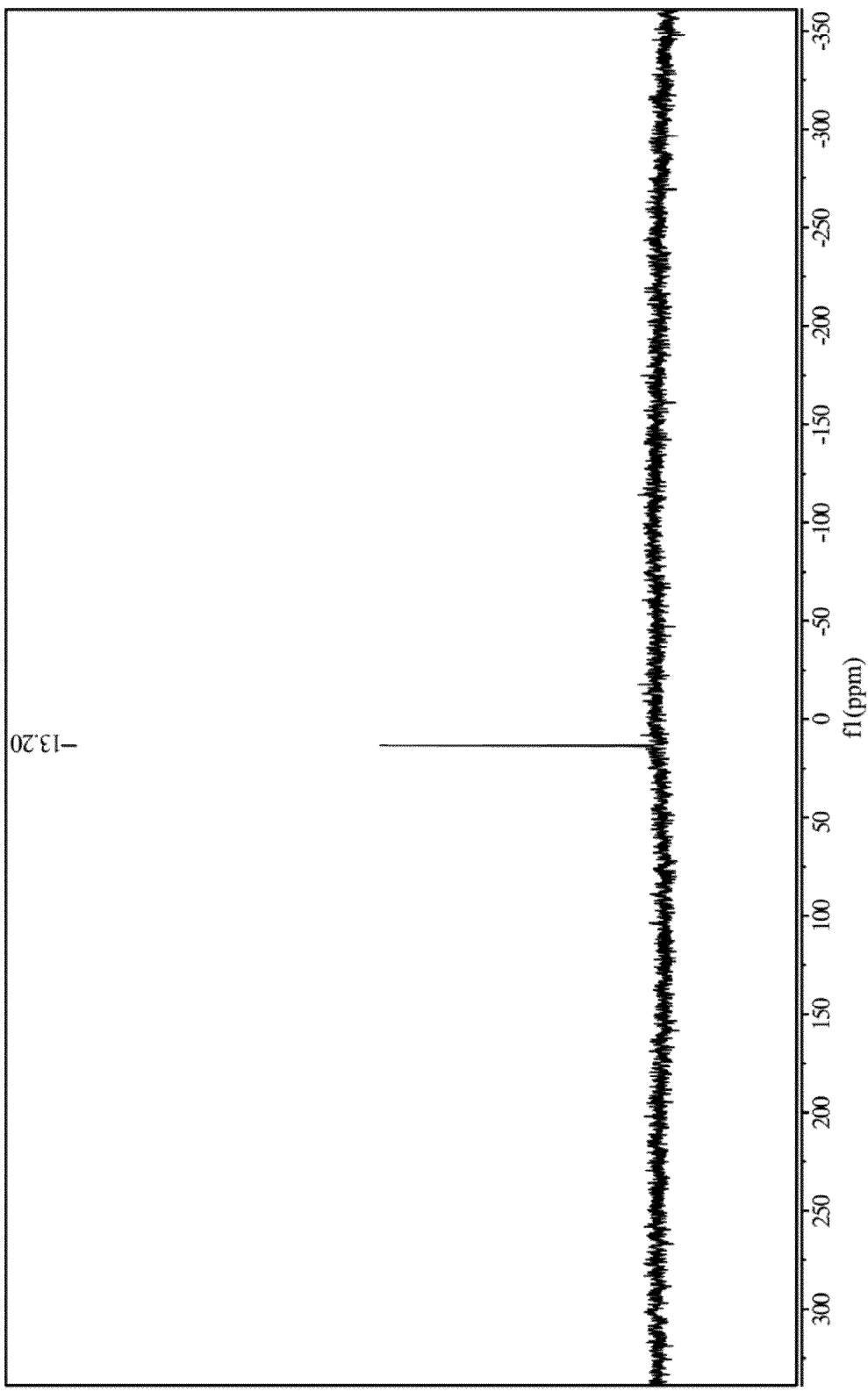
FIG. 5 is a $^{95}$Mo NMR spectrum of $[PPN]_2[MoO_4]$ in $CD_3CN$ at 25° C.
Figure 6:
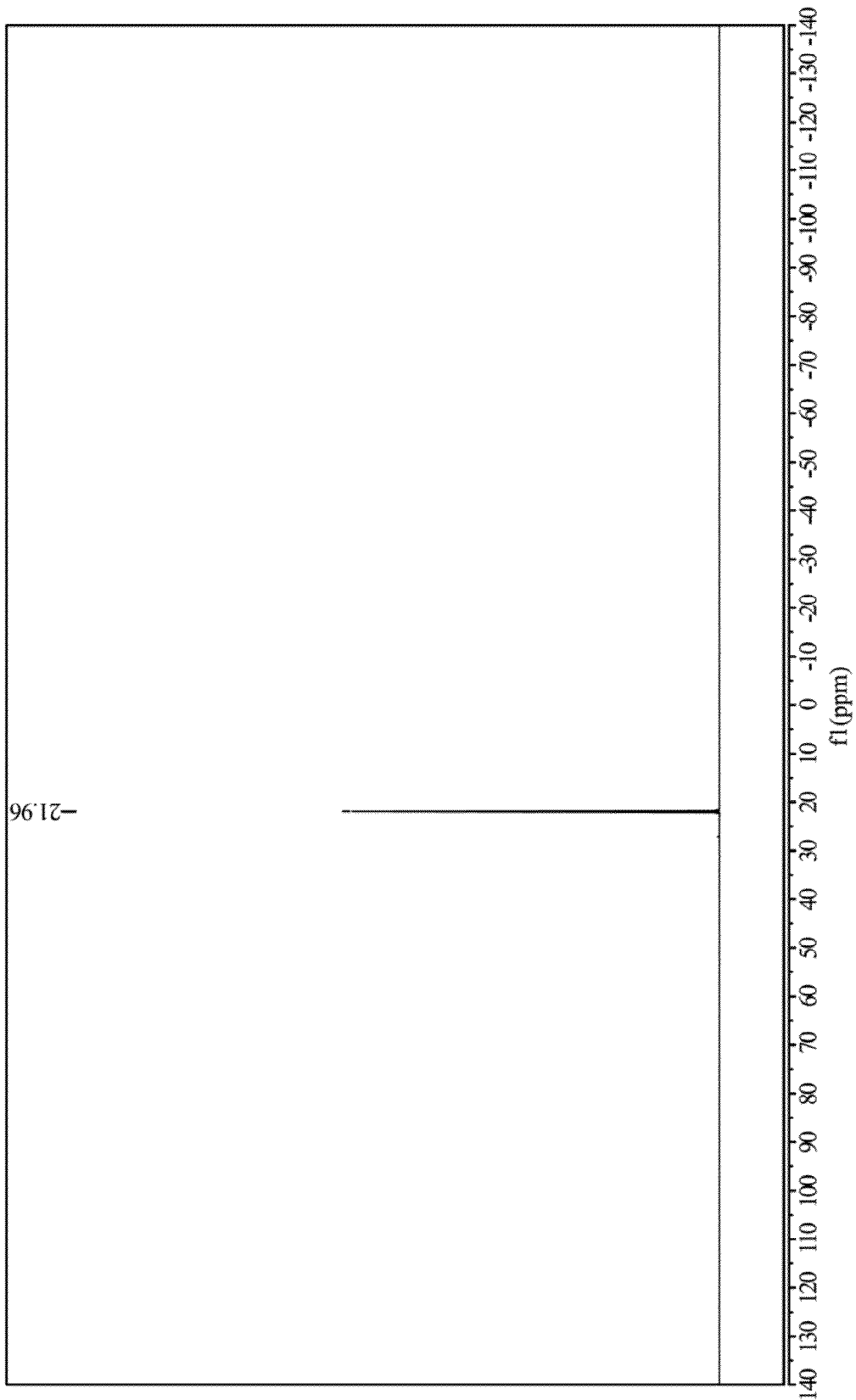
FIG. 6 is a $^{31}$P NMR spectrum of $[PPN]_2[MoO_4]$ in $CD_3CN$ at 25° C.
Figure 7:
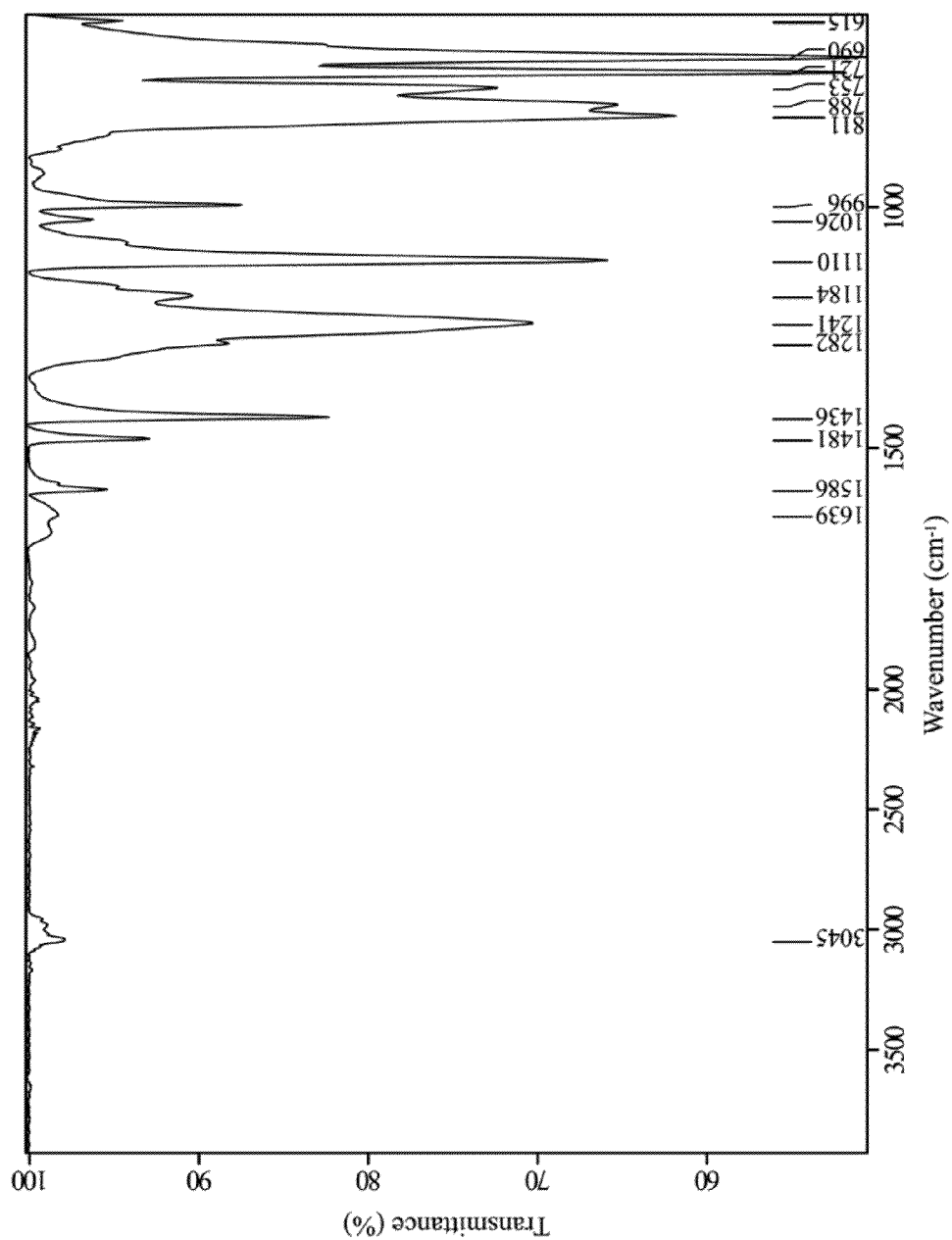
FIG. 7 is a ATR-IR spectrum of $[PPN]_2[MoO_4]$.
Figure 8:
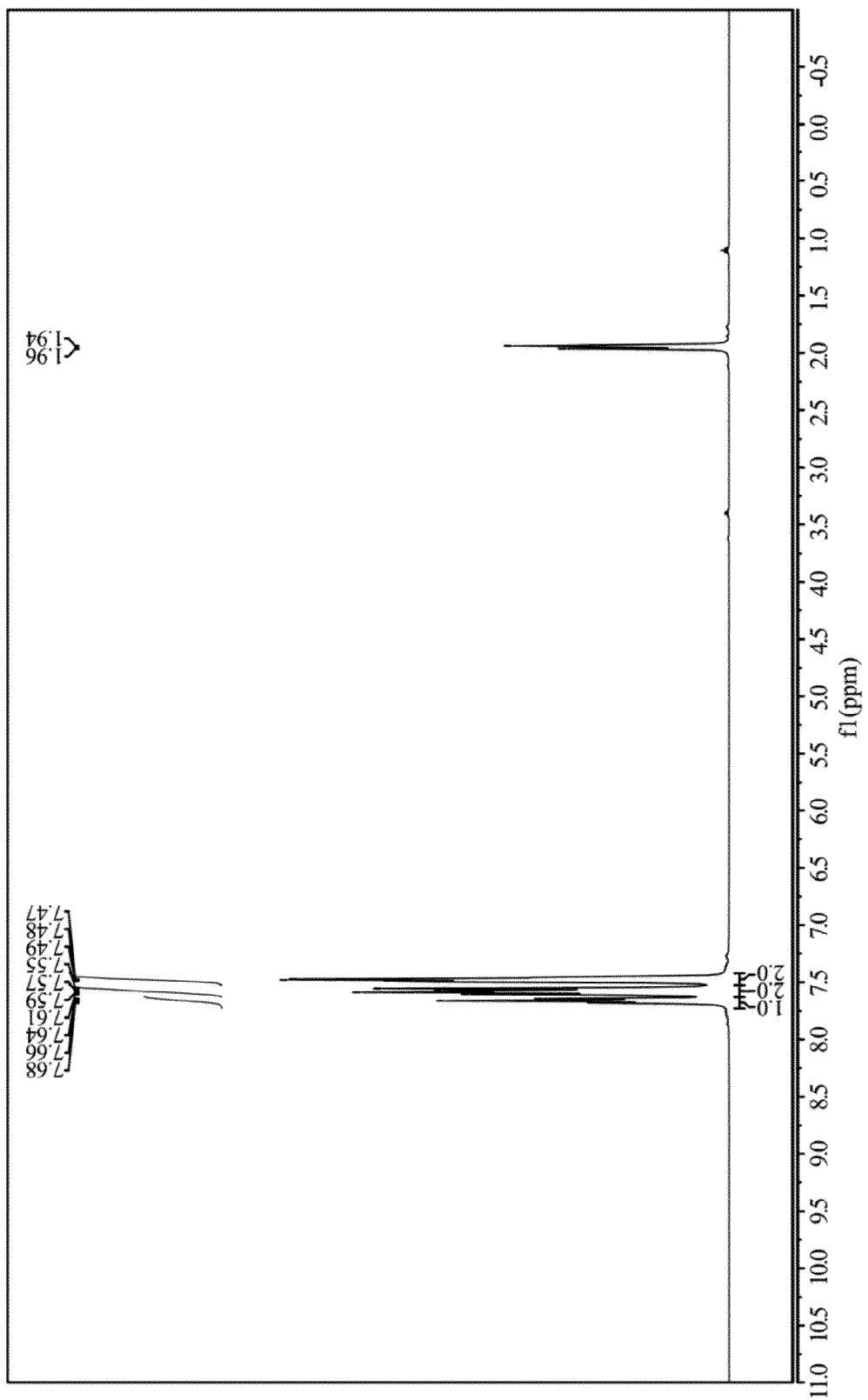
FIG. 8 is a $^1$H NMR spectrum of $[PPN]_2[MoO_3(k^2\text{-}CO_3)]$ in $CD_3CN$ at 25° C.
Figure 9:
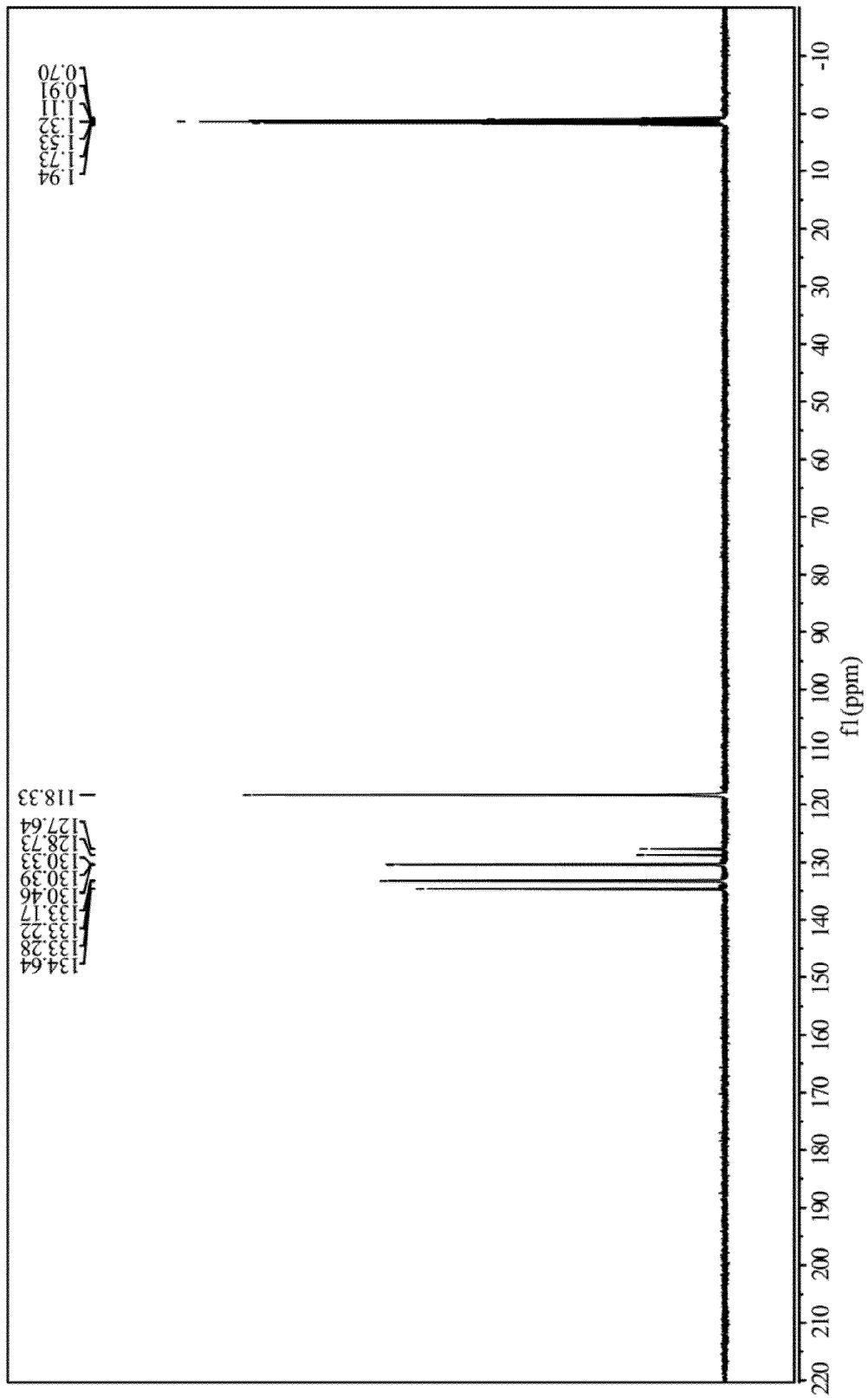
FIG. 9 is a $^{13}$C NMR spectrum of $[PPN]_2[MoO_3(k^2\text{-}CO_3)]$ in $CD_3CN$ at 25° C.
Figure 10:
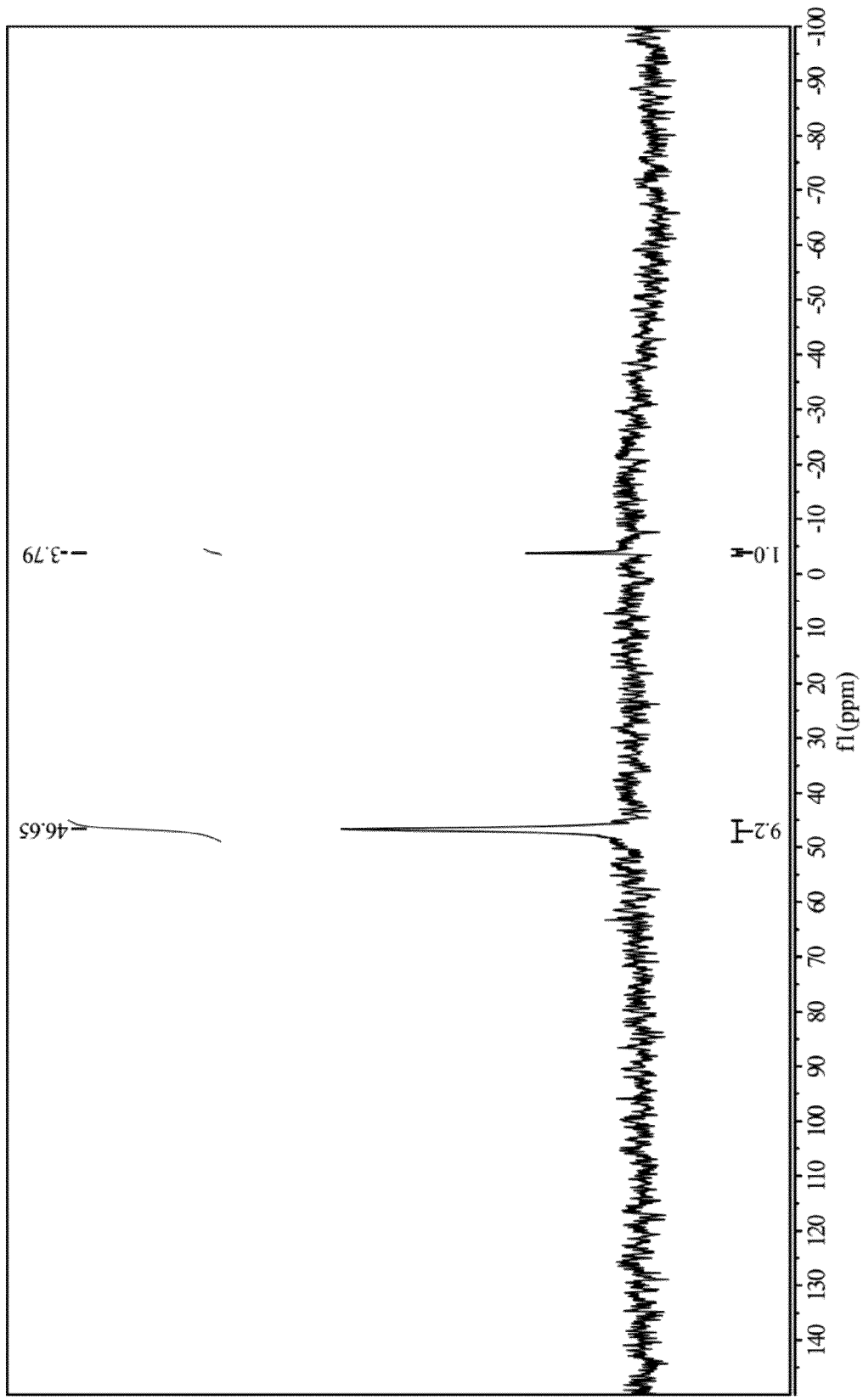
FIG. 10 is a $^{95}$Mo NMR spectrum of $[PPN]_2[MoO_3(k^2\text{-}CO_3)]$ in $CD_3CN$ at 25° C.
Figure 11:
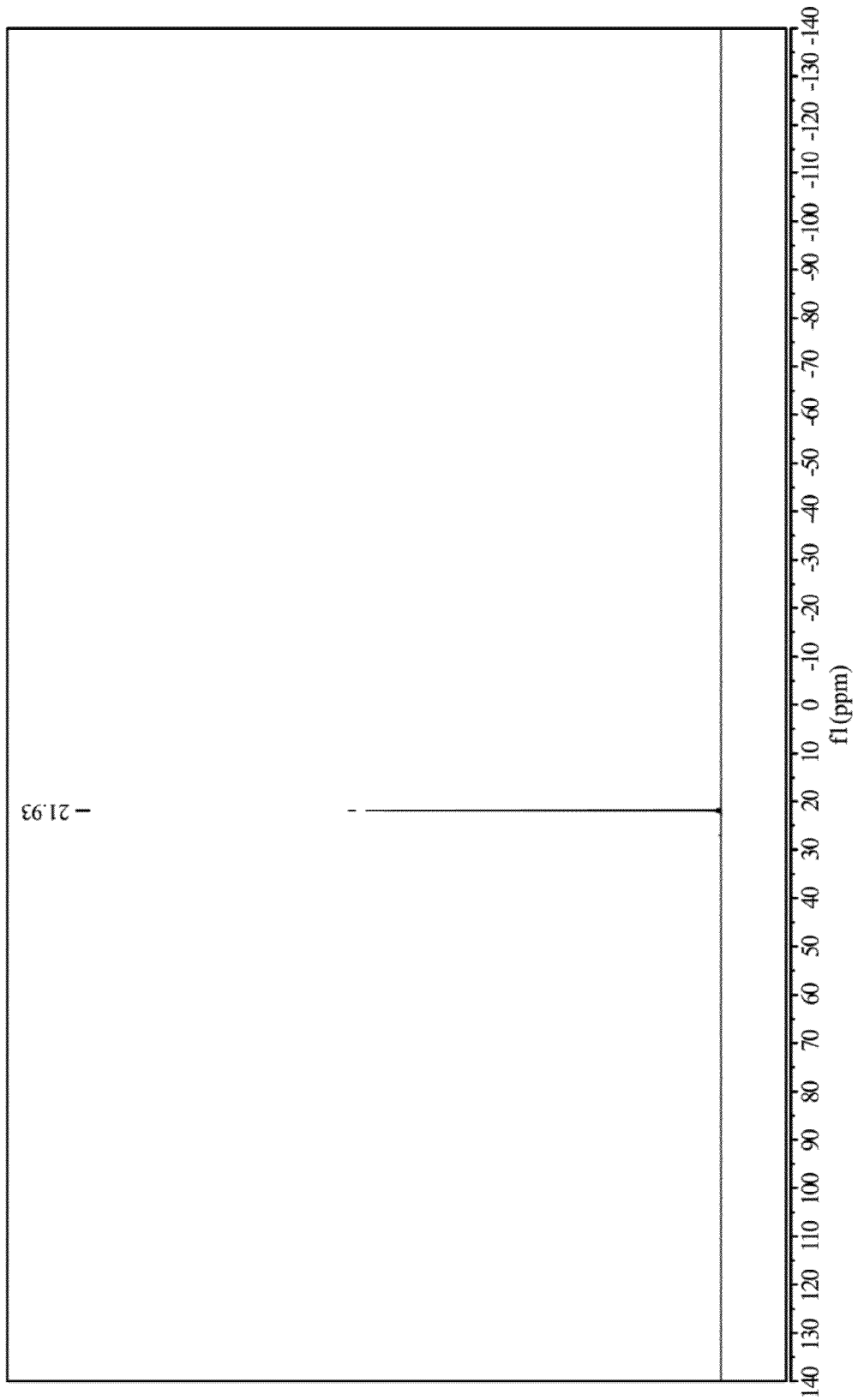
FIG. 11 is a $^{31}$P NMR spectrum of $[PPN]_2[MoO_3(k^2\text{-}CO_3)]$ in $CD_3CN$ at 25° C.
Figure 12:
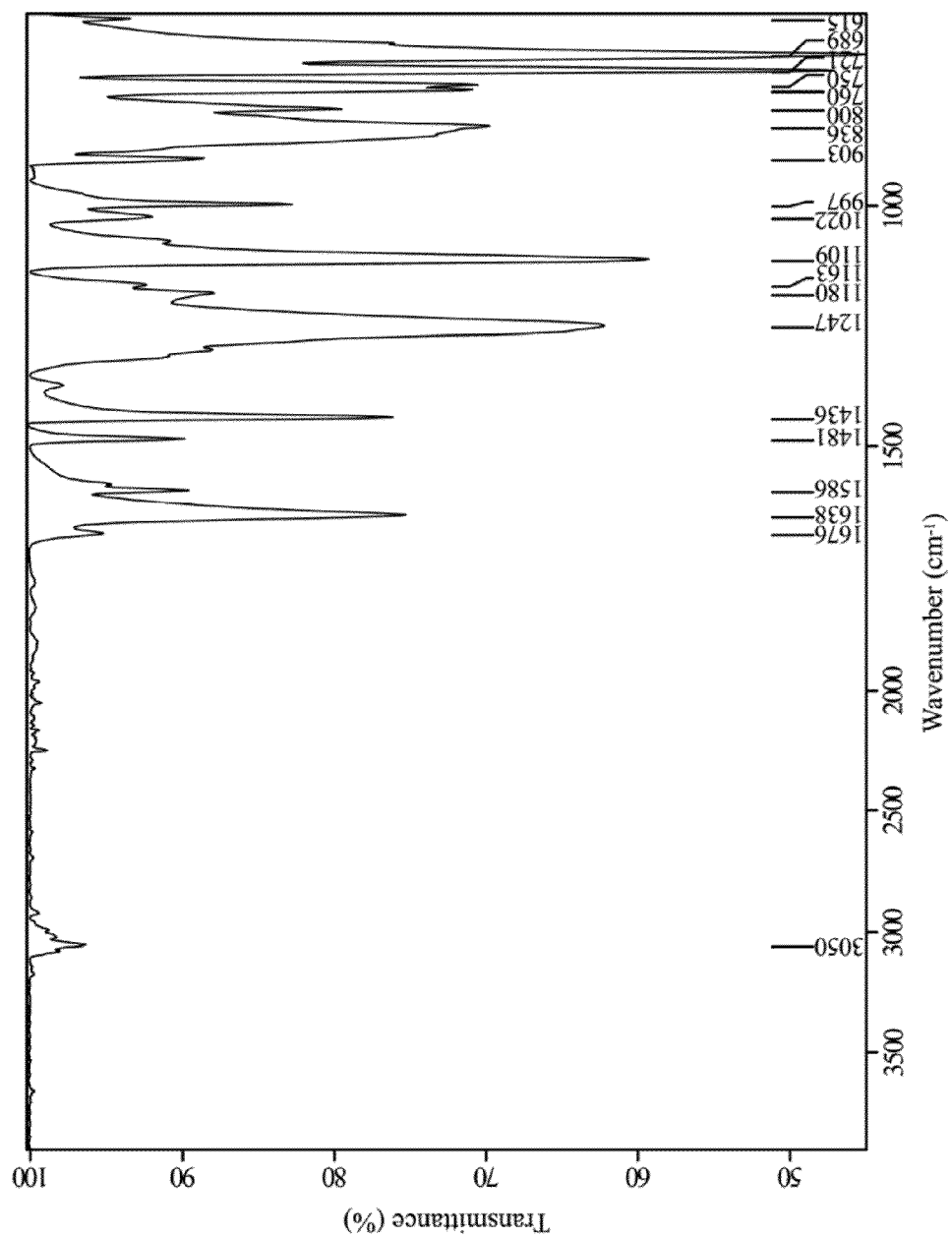
FIG. 12 is a ATR-IR spectrum of $[PPN]_2[MoO_3(k^2\text{-}CO_3)]$.
Figure 13:
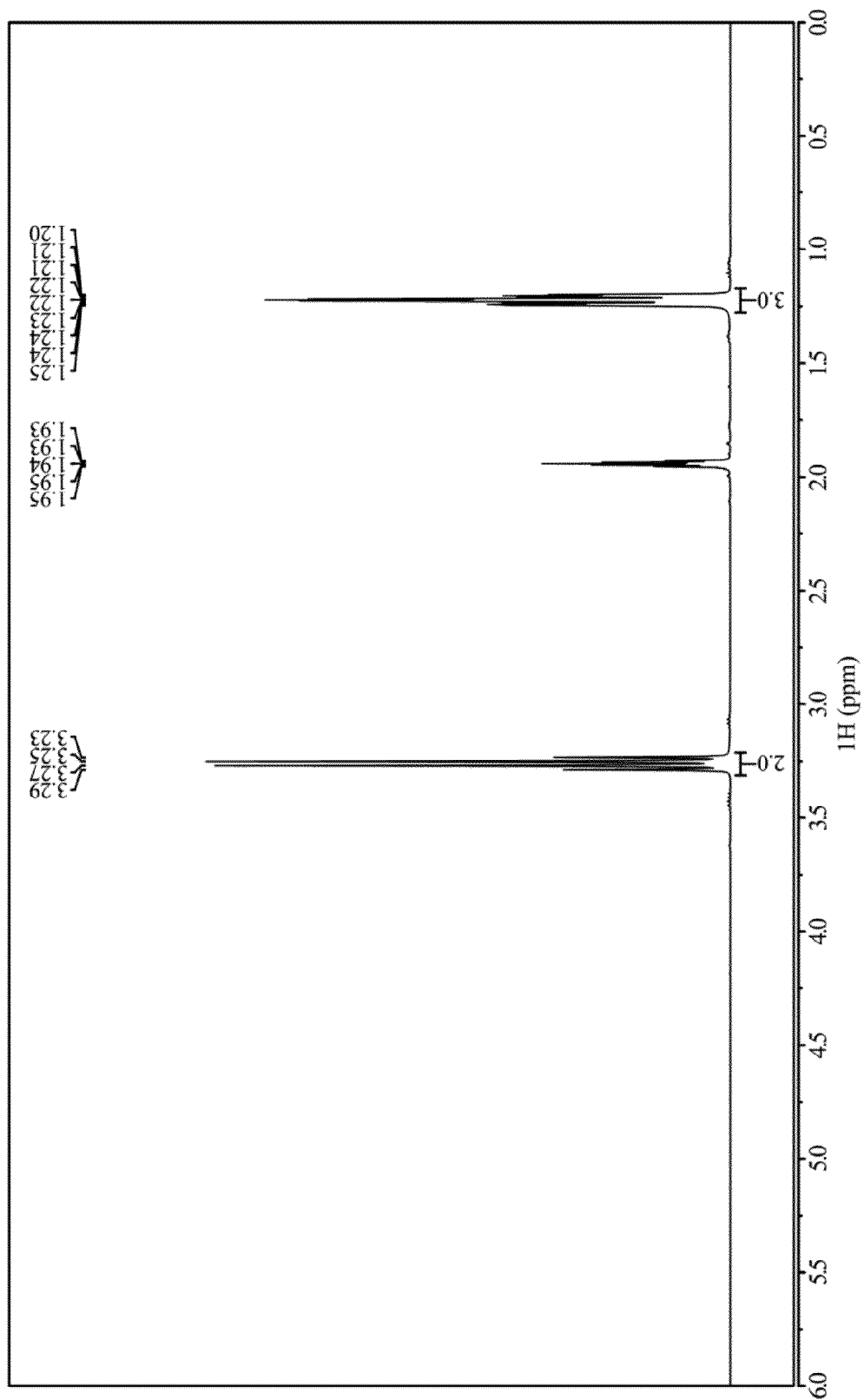
FIG. 13 is a $^1$H NMR spectrum of $[NEt_4]_2[MoO_3(k^2\text{-}CO_3)]$ in $CD_3CN$ at 25° C.
Figure 14:
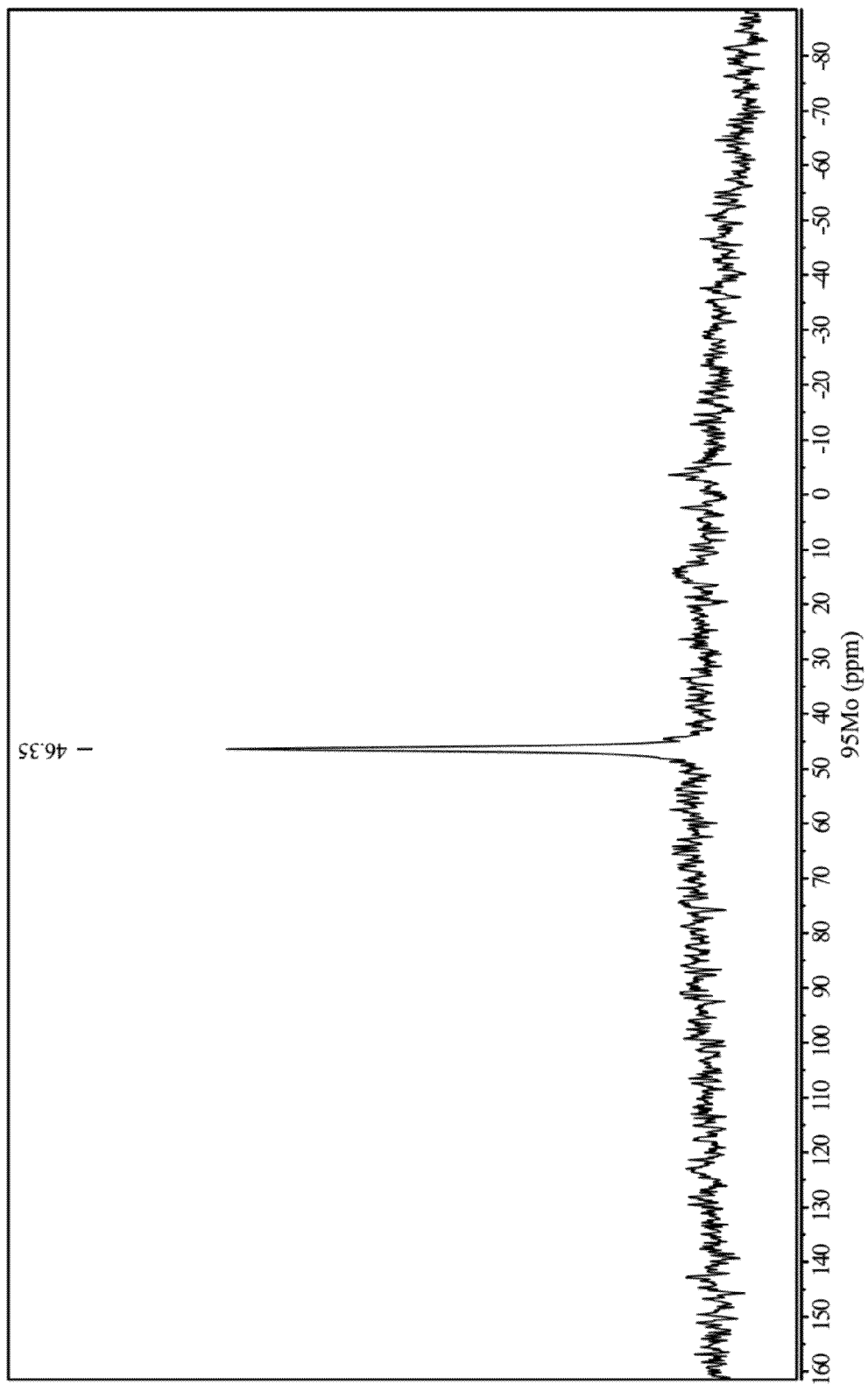
FIG. 14 is a $^{95}$Mo NMR spectrum of $[NEt_4]_2[MoO_3(k^2\text{-}CO_3)]$ in $CD_3CN$ at 25° C.
Figure 15:
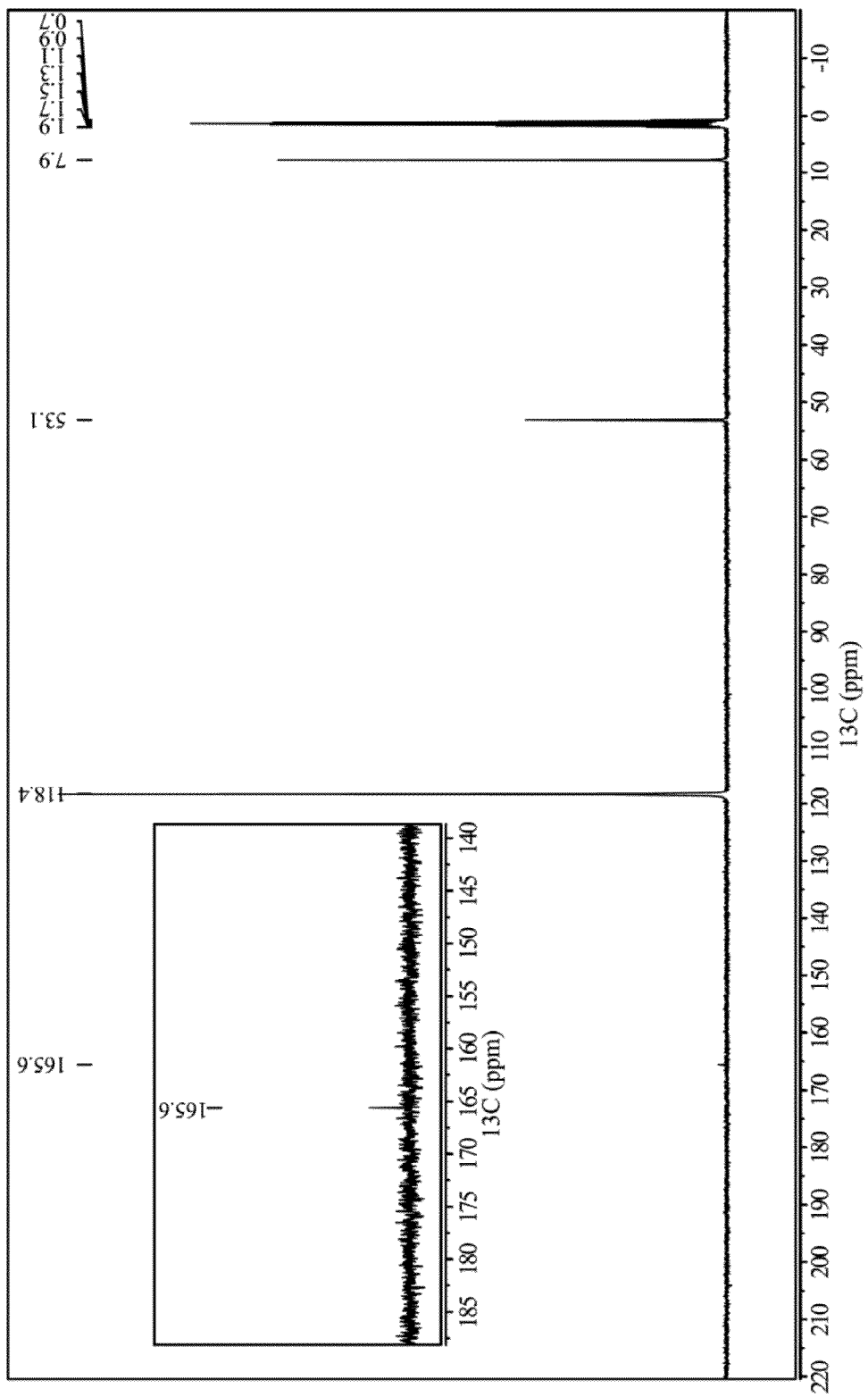
FIG. 15 is a $^{13}$C NMR spectrum of $[NEt_4]_2[MoO_3(k^2\text{-}CO_3)]$ in $CD_3CN$ at 25° C.

X-ray crystallographic data for the structures shown in FIGS. 1 and 2 are summarized in FIG. 38.

Computational Data

Computational Details

Electronic structure calculations were carried out using the M06 density functional with the Def2-QZVPP basis set for molybdenum, incorporating the SDD effective core potential, and 6-311+G(3df) for all other atoms as implemented in the Gaussian 09 suite of programs. Minimum energy and transition state structures were optimized in THF solution using the CPCM model to describe solvation effects. The obtained stationary points were characterized by performing energy second derivatives, confirming them as minima or transition states by the number of negative eigenvalues of the hessian matrix of the energy (zero and one negative eigenvalues respectively). Finally, single-point energies were calculated with the quadratic configuration interaction method with single and double excitation and perturbative corrections for triple excitations (QCISD(T)) at the optimized M06 geometries. See, for example, D. Andrae, U. Haeussermann, M. Dolg, H. Stoll and H. Preuss, *Theor Chim Acta*, 1990, 77, 123-141; M. J. Frisch et al, Gaussian 09, Revision C.01, Gaussian, Inc.: Wallingford, Conn., 2010; V. Barone and M. Cossi, *J. Phys. Chem. A*, 1998, 102, 1995-2001; A. Klamt and G. Schuurmann, *Perkin Trans.* 2, 1993, 799-805; J. A. Pople, M. Head-Gordon and K. Raghavachari, *J. Chem. Phys.*, 1987, 87, 5968-5975; and P. J. Knowles and H. -J. Werner, *Chem. Phys. Lett.*, 1985, 115, 259-267, each of which is incorporated by reference in its entirety,

| XYZ coordinates for all computed species | | |
|---|---|---|
| $CO_2$ | | |
| C | 0.00000000 | 0.00000000 | 0.00000000 |
| O | 0.00000000 | 0.00000000 | 1.15384300 |
| O | 0.00000000 | 0.00000000 | −1.15384300 |
| $[MoO_4]^{2-}$ | | |
| Mo | 0.00000000 | 0.00000000 | 0.00000000 |
| O | 1.01811200 | 1.01811200 | 1.01811200 |
| O | −1.01811200 | −1.01811200 | 1.0181.1200 |
| O | 1.01811200 | −1.01811200 | −1.01811200 |
| O | −1.01811200 | 1.01811200 | −1.01811200 |
| TS1 ($[MoO_4]_2^- + CO_2 \rightarrow [MoO_3(\kappa^2\text{-}CO_3)]^{2-}$) | | |
| C | −2.55986400 | 0.02439000 | −0.00006200 |
| O | −3.27956000 | −0.90856700 | −0.00011200 |

-continued

| \multicolumn{3}{c}{XYZ coordinates for all computed species} | | |
|---|---|---|
| O | −2.36024300 | 1.18712000 | 0.00020900 |
| O | −0.82667800 | −0.77271000 | −0.00097700 |
| Mo | 0.82267800 | −0.02825700 | −0.00003900 |
| O | 1.02641700 | 0.96430300 | 1.42417400 |
| O | 1.02747200 | 0.96632500 | −1.42274500 |
| O | 2.01343000 | −1.30641300 | −0.00029700 |
| \multicolumn{4}{c}{$[MoO_3(\kappa^2\text{-}CO_3)]^{2-}$} | | | |
| C | −1.97701500 | 0.02314300 | −0.00006400 |
| O | −3.19936200 | 0.12536000 | 0.00003500 |
| O | −1.30161800 | −1.08065000 | −0.00025200 |
| O | −1.16215000 | 1.07167300 | 0.00028700 |
| Mo | 0.63401800 | 0.00248800 | 0.00007500 |
| O | 1.17608100 | −0.83419200 | −1.40906100 |
| O | 1.17647200 | −0.83319500 | 1.40963700 |
| O | 1.46474200 | 1.52058500 | −0.00099300 |
| \multicolumn{4}{c}{TS2 ($[MoO_3(\kappa^2\text{-}CO_3)]^{2-} + CO_2 \rightarrow [MoO_2(\kappa^2\text{-}CO_3)_2]^{2-}$)} | | | |
| Mo | 0.34057700 | −0.71319200 | −0.03143300 |
| O | 0.96201000 | −1.96647100 | −1.02020200 |
| O | 0.32804900 | −1.26071100 | 1.58205900 |
| O | −2.96600900 | 1.17472800 | −1.00799000 |
| O | −1.36528300 | −0.55856200 | −0.54763200 |
| O | 0.32573100 | 1.41320100 | 0.07781900 |
| O | 2.16592700 | 0.31843400 | −0.11687200 |
| C | 1.63073000 | 1.51676600 | 0.01087700 |
| C | −2.62730000 | 0.61598200 | −0.01939800 |
| O | −2.75229700 | 0.46421700 | 1.14998900 |
| O | 2.26127300 | 2.55985900 | 0.05423900 |
| \multicolumn{4}{c}{$MoO_2(\kappa^2\text{-}CO_3)_2]^{2-}$} | | | |
| Mo | 0.00001700 | 0.65798100 | −0.00000800 |
| O | 0.37506200 | 1.68532700 | −1.29156000 |
| O | −0.37501000 | 1.68535000 | 1.29153300 |
| O | 1.06193300 | −1.04391100 | −0.94557000 |
| O | 1.71440300 | 0.02671700 | 0.81582700 |
| O | −1.06208800 | −1.04375800 | 0.94571600 |
| O | −1.71432300 | 0.02667400 | −0.81589600 |
| C | −1.98476900 | −0.97227800 | 0.05195100 |
| C | 1.98473200 | −0.97234400 | −0.05192800 |
| O | 2.98016000 | −1.66620200 | 0.05612300 |
| O | −2.98019900 | −1.66613200 | −0.05614600 |

Figure 39:
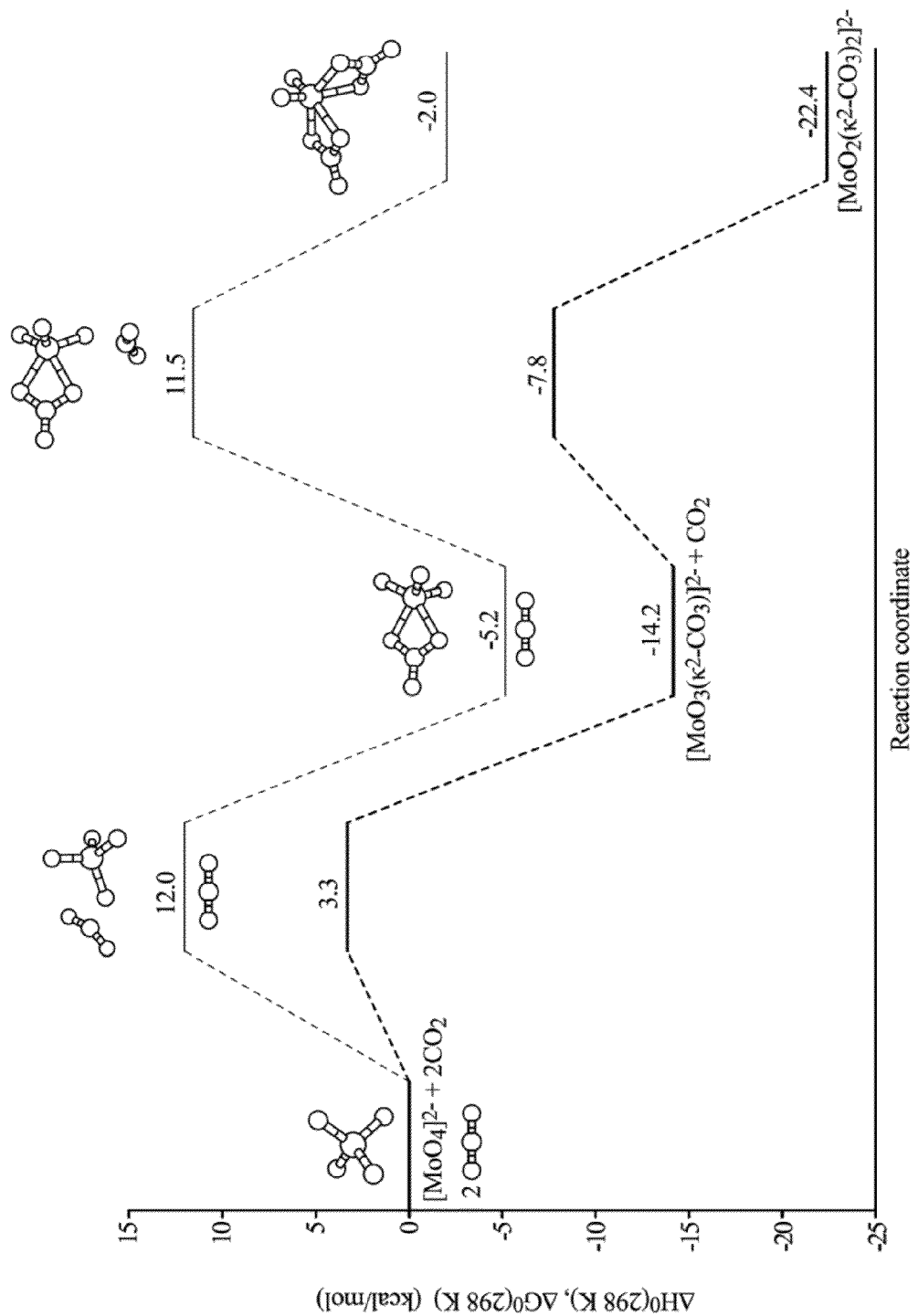
FIG. 39 is a combined calculated potential energy diagram for the first and second CO$_2$ binding events.

In order to gain insight into the energetics of this system, computational methods were used (FIG. 39). Binding of the first $CO_2$ molecule is exothermic and exergonic with a $\Delta H°$ (298 K)=−14.2 kcal/mol and $\Delta G°(298\text{ K})$=−5.2 kcal/mol. The stability of the $[MoO_3(\kappa^2\text{-}CO_3)]^{2-}$ species is explained by the considerable activation energy of $\Delta G^{\ddagger}(298\text{ K})$=17.2 kcal/mol for regenerating the molybdate with loss of $CO_2$. This is consistent with our inability to remove $CO_2$ under vacuum at room temperature from this material. As expected, binding of the second $CO_2$ is slightly endergonic ($\Delta G°(298\text{ K})$=3.2 kcal/mol), being favored at higher $CO_2$ pressures and lower temperatures as observed in $^{13}C$ labeling experiments. The possibility of binding a third $CO_2$ molecule was also investigated. However, producing such a species is endergonic with a $\Delta G°(298\text{ K})$=14.6 kcal/mol, as well as $\Delta H°>0$ and $\Delta S°<0$. In contrast to the findings of Mizuno et al. who reported a calculated $\kappa^1$ structure for the related tungstate-$CO_2$ adduct. (T. Kimura, K. Kamata and N. Mizuno, *Angew. Chem. Int. Ed.,* 2012, 51, 6700-6703 and T. Kimura, H. Sunaba, K. Kamata and N. Mizuno, *Inorg. Chem.,* 2012, 51, 13001-13008, each of which is incorporated by reference in its entirety) minima corresponding to $\kappa^1$ structures for any of the molybdenum carbonates studied herein could not be located.

Reactivity Studies

Catalytic Carboxylation of Epoxides

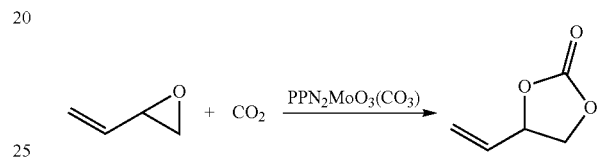

$PPN_2MoO_3CO_3$ (155 mg, 0.12 mmol, 1 equiv) was loaded in to a vial, followed by butadiene monoxide (890 mg, 12.7 mmol, 106 equiv). The vial was placed inside a Parr reactor, then pressurized with 20 bar of $CO_2$. The reactor was then placed in an oil bath and heated at 100° C. overnight (16 h). The reactor was then cooled to room temperature and then to 0° C. in an ice water bath. The pressure was vented carefully, the reactor was opened and the reaction mixture was analyzed by $^1H$ NMR. A 2:1 mixture of starting epoxide to carbonate was obtained, along with a small amount of unidentified byproduct. Turnover number under these conditions was estimated to be 30.

Carboxylation of Activated Olefins

Reaction of $PPN_2MoO_3CO_3$ with trans-1-Methoxy-3-trimethylsiloxy-1,3-butadiene (Danishefsky's diene)

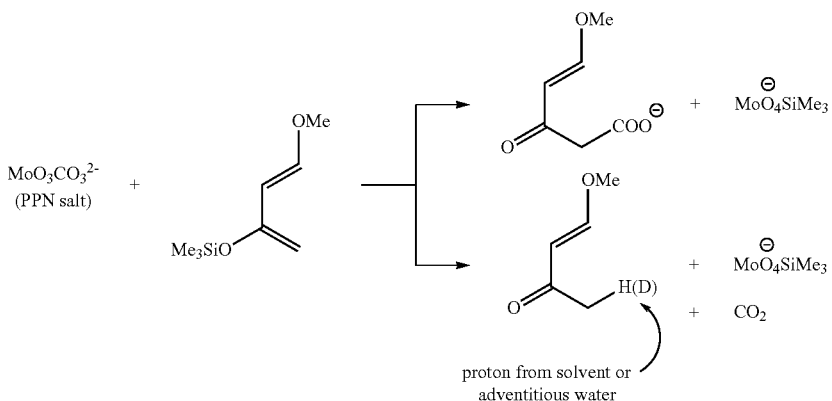

Inside the glovebox, the $PPN_2MoO_3CO_3$ (51 mg, 1 equiv) was dissolved in 0.7 mL of acetonitrile-$d_3$ and transferred to an NMR tube. The tube was capped with a septum and brought outside the glovebox, where it was subjected to 3 freeze pump thaw cycles and backfilled with 1 atm $CO_2$ by syringe. The diene (8 µL, 1 equiv) was then added using a microsyringe. ¹H NMR was taken after 20 min, showing a mixture of hydrolysis product (4-methoxybut-3-ene-2-one), as well as the two tautomers of the desired carboxylated product roughly in a 1:2 ratio (hydrolysis to sum of tautomers). ⁹⁵Mo NMR showed only [PPN][MoO₄SiMe₃] after 5 h.

Reaction of PPN₂MoO₃CO₃ with 4-Methoxyacetophenone triethyl-silylenol

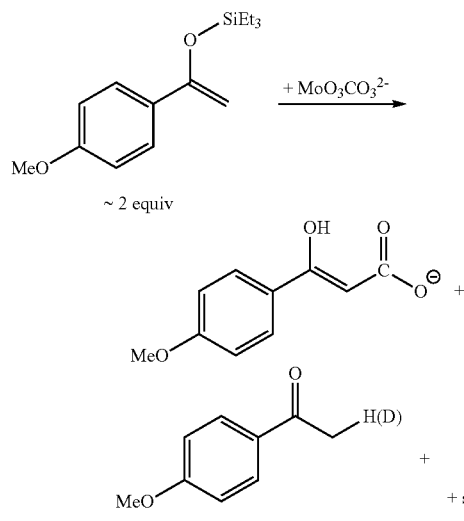

PPN₂MoO₃CO₃ (53 mg, 1 equiv) was dissolved in 0.7 mL of acetonitrile-d₃ and transferred to a vial with a stir bar. The 4-Methoxyacetophenone triethyl-silylenol (26 mg, ~2 equiv) was dissolved in 0.5 mL of acetonitrile-d₃ in a vial. Both vials were capped with septa and brought outside the glovebox. 20 mL or CO₂ were bubbled through the PPN₂MoO₃CO₃ solution, then the silylenol solution was added dropwise at room temperature under vigorous stirring. The solution was stirred for 5 min, then part of it was transferred to an NMR tube and analyzed by ¹H and ⁹⁵Mo NMR. The ration of starting triethylsilylenol to hydrolysis product (4-methoxyacetophenone) to carboxylated product (3-hydroxy-3-(4-methoxyphenyl) acrylate) by ¹H NMR was 1:2:1. The only species present by ⁹⁵Mo NMR was the triethylsilylmolybdate.

Formation of Ureas from Aromatic Diamines

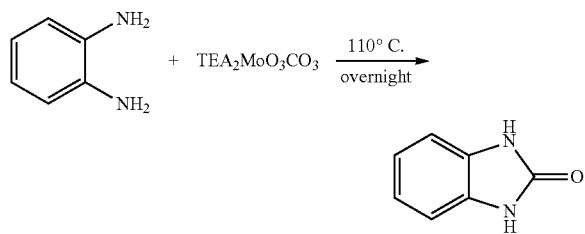

1,2-phenylenediamine (11 mg, 1 equiv) and [NEt₄]MoO₃CO₃ (46 mg, 1 equiv) were dssolved in 0.8 mL DMSO-d₆. The solution was transferred to an NMR tube and heated overnight at 110° C. A 1:1 mixture of diamine starting material and 2-benzimidazolone product could be seen by ¹H NMR. The only molybdenum species by ⁹⁵Mo NMR was dimolybdate TEA₂Mo₂O₇.

Reaction of [NEt₄]₂MoO₃CO₃ with a Ruthenium Complex

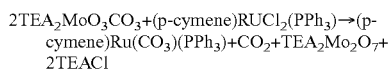

2TEA₂MoO₃CO₃+(p-cymene)RuCl₂(PPh₃)→(p-cymene)Ru(CO₃)(PPh₃)+CO₂+TEA₂Mo₂O₇+2TEACl

The molybdate monocarbonate TEA₂MoO₃CO₃ (9 mg, 1 equiv) was dissolved in 0.8 mL of acetonitrile-d₃ and this solution was used to dissolve the Ru complex (p-cymene)RuCl₂(PPh₃) (11 mg, 1 equiv). The resulting red-orange solution was transferred to an NMR tube and analyzed by ¹H and ³¹P NMR after 1 hour to confirm conversion of ½ the ruthenium complex to (p-cymene)Ru(CO₃)(PPh₃), and by ⁹⁵Mo NMR to confirm conversion of the molybdate monocarbonate to TEA₂Mo₂O₇.

Synthesis and Structural Characterization of [NEt₄]₂[WO₃(κ²-CO₃)]

Figure 40:
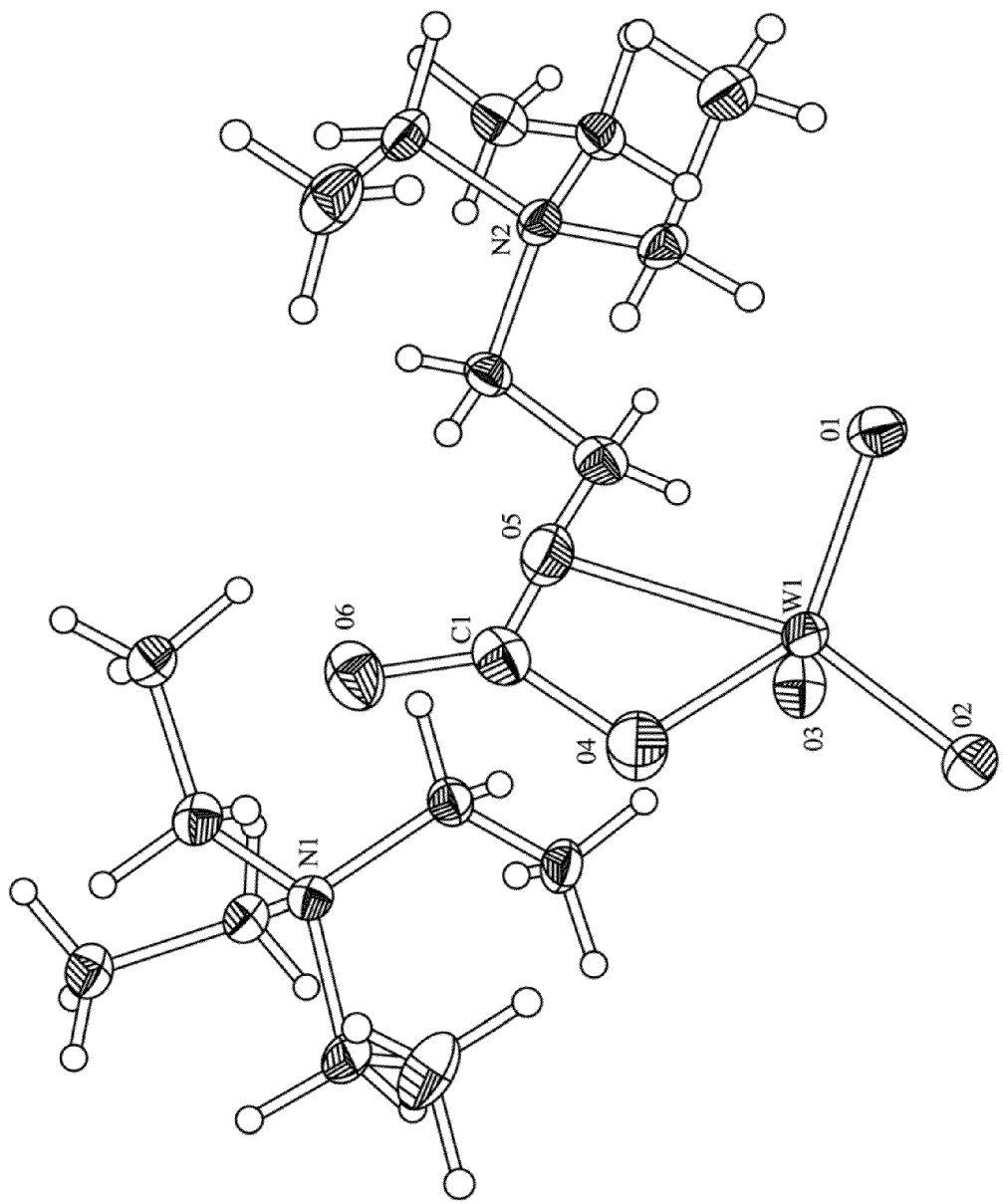
FIG. 40 is a solid-state structure of [NEt$_4$]$_2$[WO$_3$(κ$^2$-CO$_3$)] (ellipsoids at the 50% probability level, cations omitted for clarity).
Figure 41:
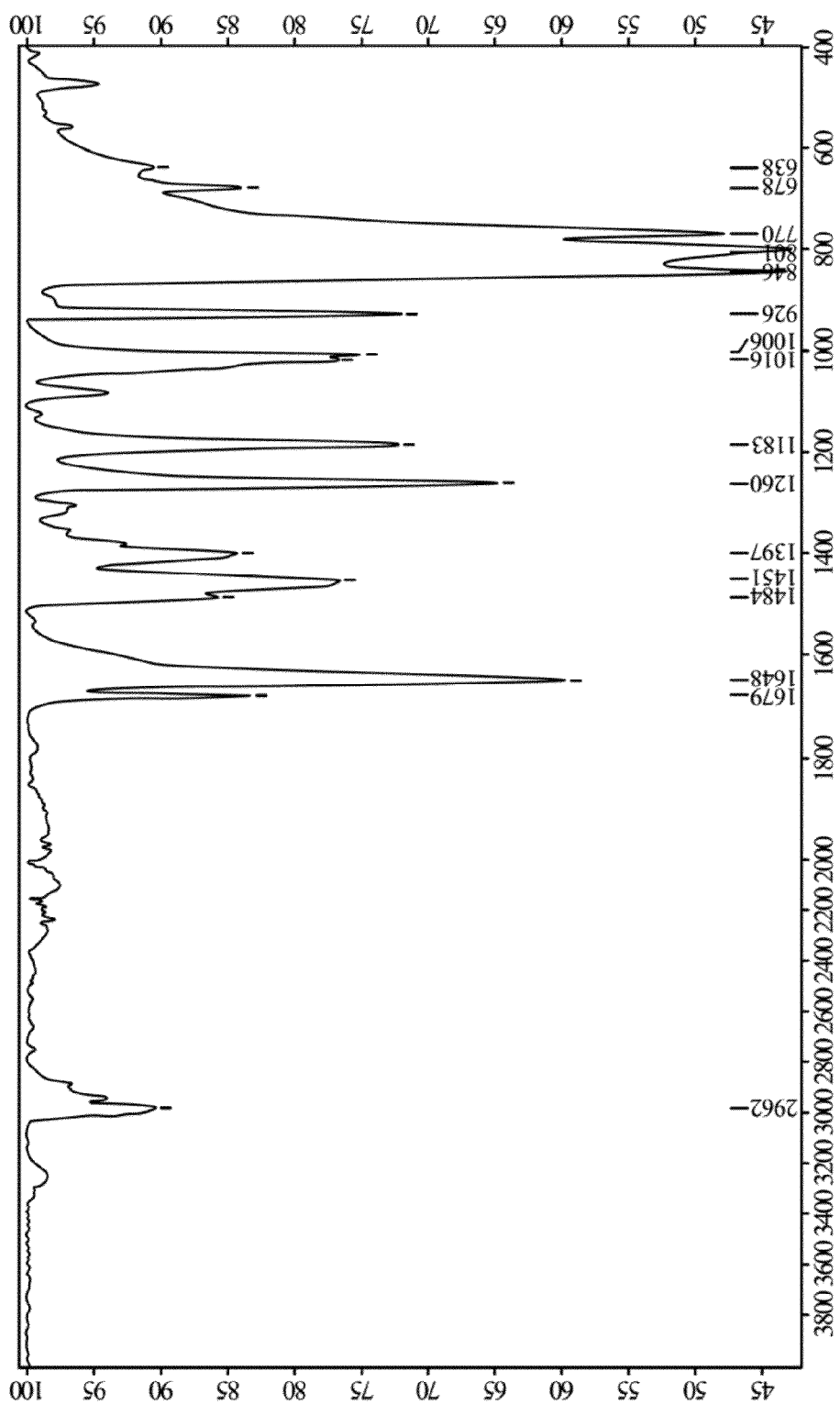
FIG. 41 is a ATR-IR spectrum of solid [NEt$_4$]$_2$[WO$_3$(κ$^2$-CO$_3$)].

[NEt₄]₂[WO₃(κ²-CO₃)] was prepared through a similar method as the Mo analogue. CO₂ was bubbled for 5-10 min through a 0.05M acetonitrile solution of [NEt₄][WO₄]. After stirring for an additional 20 min, all volatiles were removed in vacuo to yield the desired product. Single crystals were obtained via slow vapor diffusion of diethyl ether into an acetonitrile solution of the tungstate carbonate. See FIGS. 40-41 and Table 1.

TABLE 1

| Crystal data and structure refinement for X8_14157. | |
| --- | --- |
| Identification code | x8_14157 |
| Empirical formula | C₁₇H₄₀N₂O₆W |
| Formula weight | 552.36 |
| Temperature | 100(2) K |
| Wavelength | 0.71073 Å |
| Crystal system | Monoclinic |
| Space group | P2₁/n |
| Unit cell dimensions | a = 14.9615(11) Å  a = 90°. |
|  | b = 8.3504(6) Å   b = 100.0811(17)°. |
|  | c = 17.1925(13) Å  g = 90°. |
| Volume | 2114.8(3) Å³ |
| Z | 4 |
| Density (calculated) | 1.735 Mg/m³ |
| Absorption coefficient | 5.496 Mm⁻¹ |
| F(000) | 1112 |
| Crystal size | 0.430 × 0.308 × 0.085 mm³ |
| Theta range for data collection | 1.985 to 31.503°. |
| Index ranges | −21 <= h <= 21, −12 <= k <= 12, −25 <= l <= 25 |
| Reflections collected | 97602 |
| Independent reflections | 7036 [R$_{int}$ = 0.0396] |
| Completeness to theta = 25.242° | 100.0% |
| Absorption correction | Semi-empirical from equivalents |
| Refinement method | Full-matrix least-squares on F² |
| Data/restraints/parameters | 7036/0/243 |
| Goodness-of-fit on F² | 1.041 |
| Final R indices [I > 2σ(I)] | R₁ = 0.0194, wR₂ = 0.0524 |
| R indices (all data) | R₁ = 0.0216, wR₂ = 0.0538 |
| Extinction coefficient | n/a |
| Largest diff. peak and hole | 2.318 and −1.435 e Å⁻³ |

Other embodiments are within the scope of the following claims.

What is claimed is:

1. An isolated compound comprising a molybdate complex of carbon dioxide.

2. The compound of claim 1, wherein the molybdate complex includes a single molybdenum atom.

3. The compound of claim 1, wherein the molybdate complex includes a single carbonate group.

4. The compound of claim 3, wherein the molybdate complex includes [MoO₃(κ²-CO₃)]²⁻.

5. The compound of claim 1, wherein the molybdate complex includes two carbonate groups.

6. The compound of claim 5, wherein the molybdate complex includes $[MoO_2(\kappa^2\text{-}CO_3)_2]^{2-}$.

7. The compound of claim 1, further comprising a non-coordinating cation.

8. The compound of claim 7, wherein the non-coordinating cation is bis(triphenylphosphine)iminium, an ammonium or a phosphonium.

9. A method of making an isolated molybdate complex of carbon dioxide comprising:
   exposing a molybdate to carbon dioxide; and isolating the molybdate complex of carbon dioxide.

10. The method of claim 9, wherein the molybdate is exposed to greater than one atmosphere of carbon dioxide.

11. The method of claim 9, wherein the molybdate complex includes $[MoO_3(\kappa^2\text{-}CO_3)]^{2-}$.

12. A method for carbon dioxide fixation comprising:
    exposing carbon dioxide to a molybdate in the presence of a mild nucleophile to produce a carbon dioxide-transformed product.

13. The method of claim 12, wherein the mild nucleophile is a mild hydride source.

14. The method of claim 13, wherein the mild hydride source includes a silane or borane.

15. The method of claim 12, wherein the mild nucleophile is an electron-rich alkene or alkyne.

16. The method of claim 12, wherein the mild nucleophile is a metal hydride or metal alkyl.

17. The method of claim 12, wherein the mild nucleophile is an amine.

\* \* \* \* \*